(12) United States Patent
Jin

(10) Patent No.: US 8,715,691 B2
(45) Date of Patent: May 6, 2014

(54) SWINE INFLUENZA HEMAGGLUTININ VARIANTS

(75) Inventor: Hong Jin, Cupertino, CA (US)

(73) Assignee: MedImmune, LLC, Giathersburg, MD (US)

( * ) Notice: Subject to any disclaimer, the term of this patent is extended or adjusted under 35 U.S.C. 154(b) by 0 days.

(21) Appl. No.: 13/308,809

(22) Filed: Dec. 1, 2011

(65) Prior Publication Data

US 2012/0244600 A1 Sep. 27, 2012

Related U.S. Application Data

(63) Continuation of application No. 12/822,781, filed on Jun. 24, 2010, now Pat. No. 8,088,393.

(60) Provisional application No. 61/220,426, filed on Jun. 25, 2009, provisional application No. 61/227,986, filed on Jul. 23, 2009, provisional application No. 61/234,021, filed on Aug. 14, 2009, provisional application No. 61/258,890, filed on Nov. 6, 2009.

(51) Int. Cl.
*A61K 39/145* (2006.01)
*C12N 15/00* (2006.01)
*C07K 14/11* (2006.01)
*C12N 15/44* (2006.01)

(52) U.S. Cl.
USPC ............. 424/209.1; 424/210.1; 435/320.1; 435/325; 530/350; 536/23.72

(58) Field of Classification Search
None
See application file for complete search history.

(56) References Cited

U.S. PATENT DOCUMENTS

| 8,088,393 B2 | 1/2012 | Jin et al. |
| 2008/0069821 A1 | 3/2008 | Yang et al. |
| 2008/0299151 A1 | 12/2008 | Fomsgaard |

OTHER PUBLICATIONS

Luoh et al. (Journal of Virology. 1992; 66 (2): 1066-1073).*
sequence alignment of SEQ ID No: 6 with PIR 80 database Acc. No. HMIV17, 1992.*
UniProKB, C3w5x2_9INFA (Jun. 16, 2009).
Dugan et al., "The Evolutionary Genetics and Emergence of Avian Influenza in Wild Birds," FLoS Pathog. 4(5): e1000076 (2008).
Garten et al., Antigenic and genetic characteristics of swine-origin 2009 a(H1N1) influenza viruses circulating in humans, Science 325(5937):197-201 (2009).
GenBank ID FJ966974.1 (2009).

* cited by examiner

*Primary Examiner* — Shanon A Foley

(57) ABSTRACT

Polypeptides, polynucleotides, methods, compositions, and vaccines comprising influenza hemagglutinin and neuraminidase variants are provided.

11 Claims, 9 Drawing Sheets

```
                      1                                                        50
A/California/7/09     DTLCIGYHAN  NSTDTVDTVL  EKNVTVTHSV  NLLEDKHNGK  LCKLRGVAPL
A/swine/Iowa/1/76     DTLCIGYHAN  NSTDTVDTIL  EKNVTVTHSV  NLLEDRHNGK  LCKLGGIAPL
A/Swine/31            DTLCIGYHAN  NSTDTVDTVL  EKNVTVTHSV  NLLED SHNGK LCRLGGIAPL
A/South Dakota/6/07   DTICIGYHAN  NSTDTVDTVL  EKNVTVTHSV  NLLENSHNGR  LCLLKGIAPL 51                                                       100
A/California/7/09     HLGKCNIAGW  ILGNPECESL  STASSWSYIV  ETPSSDNGTC  YPGDFIDYEE
A/swine/Iowa/1/1976   HLGKCNIAGW  LLGNPECELL  FTVSSWSYIV  ETSNSDNGTC  YPGDFINYEE
A/Swine/31            QLGKCNIAGW  LLGNPECDLL  LTVSSWSYIV  ETSNSDNGTC  YPGDFIDYEE
A/South Dakota/6/07   QLGNCSVAGW  ILGNPECELL  ISKESWSYIV  EKPNPENGTC  YPGHFADYEE 101                       119                             150
A/California/7/09     LREQLSSVSS  FERFEIFPKT   SSWPNHDSNK  GVTAACPHAG  AKSFYKNLIW
A/swine/Iowa/1/76     LREQLSSVSS  FEKFEIFPKT   SSWPNHETNR  GVTAACPYAG  ANSFYRNLIW
A/Swine/31            LREQLSSVSS  FEKFEIFPKT   SSWPNHETTR  GVTAACPYAG  ASSFYRNLLW
A/South Dakota/6/07   LREQLSSVSS  LERFEIFPKE   SSWPNHTVT.  GVSASCSHNG  ESSFYRNLLW 153-155                              186
A/California/7/09     LVRKGNSYPK  LSKSYINDKG  KEVLVLWGIH  HPSTSADQQS  LYQNADAYVF
A/swine/Iowa/1/76     LVRKGNSYPK  LSKSYVNNKG  KEVLVLWGIH  HPPTSTDQQS  LYQNADAYVF
A/Swine/31            LVKKENSYPK  LSKSYVNNKG  KEVLVLWGVH  HPPTSTDQQS  LYQNADAYVS
A/South Dakota/6/07   LTGKNGLYPN  LSKSYANNKE  KEVLVLWGVH  HPPNIGNQKA  LYHTENAYVS 201                                 278                  250
A/California/7/09     VGSSRYSKKF  KPEIAIRPKV  RXKEGRMNYY  WTLVEPGDKI  TFEATGNLVV
A/swine/Iowa/1/76     VGTSKYNRKF  KPEIAARPKV  RQAGRMNYY   WTLIESGDTI  TFEATGNLVV
A/Swine/31            VGSSKYDRRF  TPEIAARPKV  RQAGRMNYY   WTLLEPGDTI  TFEATGNLVA
A/South Dakota/6/07   VVSSHYSRKF  TPEIAKRPKV  RDQEGRINYY  WTLLEPGDTI  IFEANGNLIA 251                                                      300
A/California/7/09     PRYAFAMERN  AGSGIIISDT  PVHDCNTTCQ  TPKGAINTSL  PFQNIHPITI
A/swine/Iowa/1/76     PRYAFAMNRG  FGSGIIISDA  PVHDCNTKCQ  TPKGAINTSL  PFQNIHPVTI
A/Swine/31            PRYAFALNRG  SESGIITSDA  PVHDCDTKCQ  TPHGAINSSL  PFQNIHPVTI
A/South Dakota/6/07   PRYAFALSRG  FGSGIINSNA  PMDKCDAKCQ  TPQGAINSSL  PFQNVHPVTI 301
A/California/7/09     GKCPKYVKST  KLRLATGLRN  IPSIQSR
A/swine/Iowa/1/76     GECPKYVKST  KLRMATGLRN  IPSIQSR
A/Swine/31            GECPKYVKST  KLRMVTGLRN  IPSIQSR
A/South Dakota/6/07   GECPKYVRSA  KLRMVTGLRN  IPSIQSR
```

Fig. 2

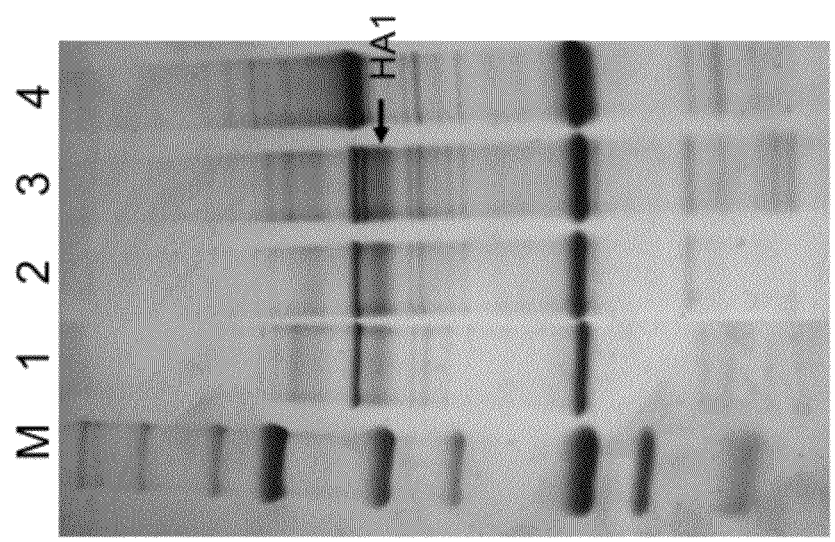

SWINE INFLUENZA HEMAGGLUTININ VARIANTS

CROSS-REFERENCE TO RELATED APPLICATIONS

This application is a Continuation Application of U.S. application Ser. No. 12/822,781, filed on Jun. 24, 2010, said application Ser. No. 12/822,781 claims the benefit under 35 U.S.C. §119(e) of U.S. Provisional Application Ser. Nos. 61/220,426, filed Jun. 25, 2009; 61/227,986, filed Jul. 23, 2009; 61/234,021, filed Aug. 14, 2009; and 61/258,890, filed Nov. 6, 2009. Each of these applications is expressly incorporated by reference in its entirety.

REFERENCE TO THE SEQUENCE LISTING

This application incorporates by reference a Sequence Listing submitted with this application as text file entitled seq list_FL265US_MED0459US created on Feb. 2, 2011 and having a size of 30 kilobytes.

BACKGROUND OF THE INVENTION

The global spread of swine-origin influenza A (H1N1) viruses in humans in April 2009 marked the first influenza pandemic in 41 years. Over 35,000 people were infected with this novel H1N1 virus as of Jun. 15, 2009. Last century, an H1N1 influenza virus also caused the devastating 1918-19 pandemic. In addition, an H1N1 virus derived from swine caused an abortive pandemic in 1976. The 1918 influenza virus caused a mild outbreak in the spring of 1918 and a lethal wave globally in the fall of that year, killing as many as 50 million people worldwide. Although the 2009 swine-origin H1N1 influenza virus was viewed as mild in early 2009, the possibility exists that this virus may mutate and become more virulent by the fall of 2009. Therefore there is an urgent need to develop an effective vaccine to prevent a severe pandemic caused by the 2009 H1N1 viruses.

6:2 reassortant influenza viruses (having the HA and NA segments of swine-origin influenza A (H1N1) viruses and the "backbone" segments of attenuated influenza viruses) useful for vaccine development, both live and killed vaccine have been isolated yet most strains isolated thus far display low titers in eggs. The same isolates infect MDCK cells poorly and form tiny plaques with poor CPE. Additionally, a severe loss of virus potency is observed after virus filtration. Accordingly, the initially isolated H1N1 reassortant influenza virus strains are poor candidates for the development of a vaccine strain.

The present invention provides new and/or newly isolated swine influenza H1 hemagglutinin variants that are capable of use for the production of numerous types of vaccines as well as in research, diagnostics, etc. The present invention further provides methods of improving the replication efficiency of H1 influenza viruses. Numerous other benefits will become apparent upon review of the following.

SUMMARY OF THE INVENTION

As described herein, 6:2 reassortant influenza strains suitable for use in the development of H1N1 vaccines were generated by reverse genetics. The initially isolated reassortant viruses comprising the wild type HA and NA genome segments, which grew poorly in eggs, were modified such that their growth in eggs is significantly improved. Sequence analysis of the modified reassortant viruses indicated that amino acid changes at positions 119, 153, 154 and 186 of the H1 swine hemagglutinin were responsible for the growth advantage in eggs and MDCK cells. Amino acid substitutions at HA residue 155, previously shown to increase swine 1976 virus replication, were also found to increase reassortant A/CA/7/09 virus replication in eggs. Viruses having amino acid changes at HA residues 119 and 186 increased egg growth without significantly altering virus antigenicity. The H1 HA variants described herein conferred increased growth phenotype on 6:2 reassortant viruses comprising the 6 internal genome segment of the PR8 or A/Ann Arbor/6/60 virus strains. Moreover, the variant viruses comprising the ca A/Ann Arbor/6/60 backbone and an H1 HA variant having an amino acid substitution at HA residue 119 or 186 were attenuated and very immunogenic in ferrets. These data indicates that the reassortant influenza virus variants comprising an amino acid substitution at HA residue 119 and/or 186 are suitable for development of an H1N1 swine influenza vaccine for human use.

DETAILED DESCRIPTION

The present invention includes polypeptide and polynucleotide sequences of influenza hemagglutinin as well as vectors, viruses, vaccines, compositions and the like comprising such sequences and methods of their use. Additional features of the invention are described in more detail herein.

In some aspects, the invention provides isolated or recombinant hemagglutinin polypeptides. In one embodiment, an isolated or recombinant HA polypeptide of the invention is an H1 HA polypeptide. In another embodiment, the isolated or recombinant HA polypeptide of the invention may be a swine influenza HA polypeptide.

In one embodiment, an isolated or recombinant HA polypeptide of the invention may comprise a non naturally occurring amino acid at the position corresponding to amino acid residue position 119 of SEQ ID NO: 1 or the position corresponding to amino acid residue position 186 of SEQ ID NO: 1. In another embodiment, an isolated or recombinant HA polypeptide of the invention may comprise a non naturally occurring amino acid at the position corresponding to amino acid residue position 119 of SEQ ID NO: 1 and the position corresponding to amino acid residue position 186 of SEQ ID NO: 1. In a further embodiment, an isolated or recombinant HA polypeptide of the invention comprises at least one amino acid substitution selected from the group consisting of K119E, K119N and A186D.

In a specific embodiment, an isolated or recombinant HA polypeptide of the invention comprises the amino acid sequence of SEQ NO:1 comprising at least one amino acid substitution selected from the group consisting of K119E, K119N and A186D. In another specific embodiment, an isolated or recombinant HA polypeptide of the invention may comprise a glutamic acid (E) at the amino acid residue corresponding to the amino acid residue of position 119 of SEQ ID NO: 1, and an aspartic acid (D) at the amino acid residue corresponding to the amino acid residue of position 186 of SEQ ID NO: 1. In a further specific embodiment, an isolated or recombinant HA polypeptide of the invention may comprise an asparagine (N) at the amino acid residue corresponding to the amino acid residue of position 119 of SEQ ID NO: 1, and an aspartic acid (D) at the amino acid residue corresponding to the amino acid residue of position 186 of SEQ ID NO: 1.

In a further embodiment, an isolated or recombinant HA polypeptide of the invention may further comprise the H273Y substitution.

In a further embodiment, an isolated or recombinant HA polypeptide of the invention may further comprise the D222G and/or Q223R substitution.

In a specific embodiment, an HA polypeptide of the invention comprises the acid sequence of SEQ ID NO:6 or 8. In another embodiment, an HA polypeptide of the invention comprises an amino acid sequence having at least 95%, at least 98%, at least 98.5%, at least 99%, at least 99.2%, at least 99.4%, at least 99.6%, at least 99.8% or at least 99.9% sequence identity to the amino acid sequence of SEQ NO:6 or 8. In a further embodiment, an HA polypeptide of the invention comprises the amino acid sequence of SEQ ID NO:6 or 8 comprising less than 3, less than 5, less then 10, less then 15, less than 20, less than 25, less than 30 amino acid substitutions, deletions or insertions.

In a specific embodiment, an HA polypeptide of the invention comprises the amino acid sequence of residues 1-327 of SEQ NO:6 or 8. In another embodiment, an HA polypeptide of the invention comprises an amino acid sequence having at least 95%, at least 98%, at least 98.5%, at least 99%, at least 99.2%, at least 99.4%, at least 99.6%, at least 99.8% or at least 99.9% sequence identity to the amino acid sequence of residues 1-327 of SEQ ID NO:6 or 8. In a further embodiment, an HA polypeptide of the invention comprises the amino acid sequence of residues 1-327 of SEQ ID NO:6 or 8 comprising less than 3, less than 5, less then 10, less then 15, less than 20, less than 25, less than 30 amino acid substitutions, deletions or insertions.

The invention also encompasses nucleic acids encoding polypeptides of the invention and reassortant or recombinant influenza viruses comprising such polypeptides and/or nucleic acids of the invention.

In a specific embodiment, a nucleic acid of the invention comprises the nucleotide sequence of SEQ ID NO:7. In another embodiment, a nucleic acid of the invention comprises a nucleotide sequence having at least 95%, at least 98%, at least 98.5%, at least 99%, at least 99.2%, at least 99.4%, at least 99.6%, at least 99.8% or at least 99.9% sequence identity to the nucleotide sequence of SEQ ID NO:7. In a further embodiment, a nucleic acid of the invention comprises the nucleotide sequence of SEQ ID NO:7 comprising less than 3, less than 5, less then 10, less then 15, less than 20, less than 25, less than 30 nucleotide substitutions, deletions or insertions.

In a specific embodiment, a nucleic acid of the invention comprises the nucleotide sequence of residues 84 to 1064 of SEQ ID NO:7. In another embodiment, a nucleic acid of the invention comprises a nucleotide sequence having at least 95%, at least 98%, at least 98.5%, at least 99%, at least 99.2%, at least 99.4%, at least 99.6%, at least 99.8% or at least 99.9% sequence identity to the nucleotide sequence of 84 to 1064 of SEQ ID NO:7. In a further embodiment, a nucleic acid of the invention comprises the nucleotide sequence of 84 to 1064 of SEQ ID NO:7 comprising less than 3, less than 5, less then 10, less then 15, less than 20, less than 25, less than 30 nucleotide substitutions, deletions or insertions.

In one embodiment, a reassortant or recombinant influenza virus of the invention comprises 6 internal genome segments from A/Ann Arbor/6/60, a first genome segment encoding an HA polypeptide comprising the amino acid sequence of SEQ NO:6 or 8, and a second genome segment encoding a neuramidinase polypeptide. In a specific embodiment, the first genome segment may encode an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of SEQ ID NO:6 or 8. In a specific embodiment, the first genome segment may encode an HA polypeptide comprising the amino acid sequence of SEQ ID NO:6 or 8 comprising less than 3, less than 5, less then 10, less then 15, less than 20, less than 25, less than 30 amino acid substitutions, deletions or insertions. In a specific embodiment, the second genome segment comprises the nucleotide sequence of SEQ ID NO:5. In a specific embodiment, the neuramidinase polypeptide comprises the amino acid sequence of SEQ ID NO:4. In a specific embodiment, a reassortant or recombinant influenza virus grows to a titer of at least about $7.5 \log_{10}$ PFU/ml, at least about $8 \log_{10}$ PFU/ml, at least about $8.5 \log_{10}$ PFU/ml, at least about $9 \log_{10}$ PFU/ml, at least about $9.5 \log_{10}$ PFU/ml, at least about $10 \log_{10}$ PFU/ml, at least about $10.5 \log_{10}$ PFU/ml or at least about $11 \log_{10}$ PFU/ml in embryonated eggs. In a specific embodiment, a reassortant or recombinant influenza virus grows to a titer of at least about $7.5 \log_{10}$ PFU/ml, at least about $8 \log_{10}$ PFU/ml, at least about $8.5 \log_{10}$ PFU/ml, at least about $9 \log_{10}$ PFU/ml, at least about $9.5 \log_{10}$ PFU/ml, at least about $10 \log_{10}$ PFU/ml, at least about $10.5 \log_{10}$ PFU/ml or at least about $11 \log_{10}$ PFU/ml in tissue cultures.

In another embodiment, a reassortant or recombinant influenza virus of the invention comprises 6 internal genome segments from A/Ann Arbor/6/60, a first genome segment encoding an HA polypeptide comprising the amino acid sequence of residues 1-327 SEQ ID NO:6 or 8, and a second genome segment encoding a neuramidinase polypeptide. In a specific embodiment, the first genome segment may encode an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of residues 1-327 SEQ ID NO:6. In a specific embodiment, the first genome segment may encode an HA polypeptide comprising the amino acid sequence of residues 1-327 SEQ ID NO:6 or 8 comprising less than 3, less than 5, less then 10, less then 15, less than 20, less than 25, less than 30 amino acid substitutions, deletions or insertions. In a specific embodiment, the second genome segment comprises the nucleotide sequence of SEQ ID NO:5. In a specific embodiment, the neuramidinase polypeptide comprises the amino acid sequence of SEQ NO:4. In a specific embodiment, a reassortant or recombinant influenza virus grows to a titer of at least about $7.5 \log_{10}$ PFU/ml, at least about $8 \log_{10}$ PFU/ml, at least about $8.5 \log_{10}$ PFU/ml, at least about $9 \log_{10}$ PFU/ml, at least about $9.5 \log_{10}$ PFU/ml, at least about $10 \log_{10}$ PFU/ml, at least about $10.5 \log_{10}$ PFU/ml or at least about $11 \log_{10}$ PFU/ml embryonated eggs. In a specific embodiment, a reassortant or recombinant influenza virus grows to a titer of at least about $7.5 \log_{10}$ PFU/ml, at least about $8 \log_{10}$ PFU/ml, at least about $8.5 \log_{10}$ PFU/ml, at least about $9 \log_{10}$ PFU/ml, at least about $9.5 \log_{10}$ PFU/ml, at least about $10 \log_{10}$ PFU/ml, at least about $10.5 \log_{10}$ PFU/ml or at least about $11 \log_{10}$ PFU/ml in tissue cultures.

In one embodiment, a reassortant or recombinant influenza virus of the invention comprises 6 internal genome segments from A/Puerto Rico/8/34, a first genome segment encoding an HA polypeptide comprising: the amino acid sequence of SEQ NO:6 or 8, and a second genome segment encoding a neuramidinase polypeptide. In a specific embodiment, the first genome segment may encode an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of SEQ ID NO:6 or 8. In a specific embodiment, the first genome segment may encode an HA polypeptide comprising the amino acid sequence of SEQ ID NO:6 or 8 comprising less than 3, less than 5, less then 10, less then 15, less than 0, less than 25, less than 30 amino acid substitutions, deletions or insertions. In a specific embodiment, the second genome segment comprises the nucleotide sequence of SEQ ID NO:5. In a specific embodiment, the neuramidinase polypeptide comprises the amino acid sequence of SEQ NO:4. In a specific embodiment, a reassortant or recombinant influenza virus grows to a titer of at least about 7.5 $\log_{10}$ PFU/ml, at least about 8 $\log_{10}$ PFU/ml, at least about 8.5 $\log_{10}$ PFU/ml, at least about 9 $\log_{10}$ PFU/ml, at least about 9.5 $\log_{10}$ PFU/ml, at least about 10 $\log_{10}$ PFU/ml, at least about 10.5 $\log_{10}$ PFU/ml, or at least about 11 $\log_{10}$ PFU/ml in embryonated eggs. In a specific embodiment, a reassortant or recombinant influenza virus grows to a titer of at least about 7.5 $\log_{10}$ PFU/ml, at least about 8 $\log_{10}$ PFU/ml, at least about 8.5 $\log_{10}$ PFU/ml, at least about 9 $\log_{10}$ PFU/ml, at least about 9.5 $\log_{10}$ PFU/ml, at least about 10 $\log_{10}$ PFU/ml, at least about 10.5 $\log_{10}$ PFU/ml or at least about 11 $\log_{10}$ PFU/ml in tissue cultures.

In another embodiment, a reassortant or recombinant influenza virus of the invention comprises 6 internal genome segments from A/Puerto Rico/8/34, a first genome segment encoding an HA polypeptide comprising the amino acid sequence of residues 1-327 SEQ ID NO:6 or 8, and a second genome segment encoding a neuramidinase polypeptide. In a specific embodiment, the first genome segment may encode an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of residues 1-327 SEQ ID NO:6 or 8. In a specific embodiment, the first genome segment may encode an HA polypeptide comprising the amino acid sequence of residues 1-327 SEQ NO:6 or 8 comprising less than 3, less than 5, less then 10, less then 15, less than 20, less than 25, less than 30 amino acid substitutions, deletions or insertions. In a specific embodiment, the second genome segment comprises the nucleotide sequence of SEQ ID NO:5. In a specific embodiment, the neuramidinase polypeptide comprises the amino acid sequence of SEQ ID NO:4. In a specific embodiment, a reassortant or recombinant influenza virus grows to a titer of at least about 7.5 $\log_{10}$ PFU/ml, at least about 8 $\log_{10}$ PFU/ml, at least about 8.5 $\log_{10}$ PFU/ml, at least about 9 $\log_{10}$ PFU/ml, at least about 9.5 $\log_{10}$ PFU/ml, at least about 10 $\log_{10}$ PFU/ml, at least about 10.5 $\log_{10}$ PFU/ml or at least about 11 $\log_{10}$ PFU/ml in embryonated eggs. In a specific embodiment, a reassortant or recombinant influenza virus grows to a titer of at least about 7.5 $\log_{10}$ PFU/ml, at least about 8 $\log_{10}$ PFU/ml, at least about 8.5 $\log_{10}$ PFU/ml, at least about 9 $\log_{10}$ PFU/ml, at least about 9.5 $\log_{10}$ PFU/ml, at least about 10 $\log_{10}$ PFU/ml, at least about 10.5 $\log_{10}$ PFU/ml or at least about 11 $\log_{10}$ PFU/ml in tissue cultures.

In one embodiment, a reassortant or recombinant influenza virus of the invention comprises 6 internal genome segments from A/Ann Arbor/6/60, a first genome segment comprising the nucleotide sequence of SEQ ID NO:7, and a second genome segment encoding a neuramidinase polypeptide. In another embodiment, a reassortant or recombinant influenza virus of the invention comprises 6 internal genome segments from A/Ann Arbor/6/60, a first genome segment comprising the nucleotide sequence of residues 84-1064 of SEQ ID NO:7, and a second genome segment encoding a neuramidinase polypeptide. In a further embodiment, a reassortant or recombinant influenza virus of the invention comprises 6 internal genome segments from A/Puerto Rico/8/34, a first genome segment comprising the nucleotide sequence of SEQ ID NO:7, and a second genome segment encoding a neura-midinase polypeptide. In another embodiment, a reassortant or recombinant influenza virus of the invention comprises 6 internal genome segments from A/Puerto Rico/8/34, a first genome segment comprising the nucleotide sequence of residues 84-1064 of SEQ ID NO:7, and a second gnome segment encoding a neuramidinase polypeptide. In a specific embodiment, the second genome segment comprises the nucleotide sequence of SEQ ID NO:5. In a specific embodiment, the neuramidinase polypeptide comprises the amino acid sequence of SEQ ID NO:4. In a specific embodiment, a reassortant or recombinant influenza virus grows to a titer of at least about 7.5 $\log_{10}$ PFU/ml, at least about 8 $\log_{10}$ PFU/ml, at least about 8.5 $\log_{10}$ PFU/ml, at least about 9 $\log_{10}$ PFU/ml, at least about 9.5 $\log_{10}$ PFU/ml, at least about 10 $\log_{10}$ PFU/ml, at least about 10.5 $\log_{10}$ PFU/ml or at least about 11 $\log_{10}$ PFU/ml embryonated eggs. In a specific embodiment, a reassortant or recombinant influenza virus grows to a titer of at least about 7.5 $\log_{10}$ PFU/ml, at least about 8 $\log_{10}$ PFU/ml, at least about 8.5 $\log_{10}$ PFU/ml, at least about 9 $\log_{10}$ PFU/ml, at least about 9.5 $\log_{10}$ PFU/ml, at least about 10 $\log_{10}$ PFU/ml, at least about 10.5 $\log_{10}$ PFU/ml or at least about 11 $\log_{10}$ PFU/ml in tissue cultures.

In other aspects, the invention comprises a sterile composition with one or more polypeptide listed above, or fragments thereof. The invention also encompasses immunogenic compositions comprising an immunologically effective amount of one or more of the polypeptides described above, as well as methods for stimulating the immune system of an individual to produce a protective immune response against an influenza virus comprising administering to the individual an immunologically effective amount of one or more of the polypeptides described above. In a specific embodiment, an immunogenic composition of the invention comprises a polypeptide comprising the amino acid sequence of SEQ NO:6 or 8. In another embodiment, an immunogenic composition of the invention comprises a polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of SEQ ID NO:6 or 8, in a further embodiment, an immunogenic composition of the invention comprises a polypeptide comprising the amino acid sequence of SEQ NO:6 or 8 comprising less than 3, less than 5, less then 10, less then 15, less than 20, less than 25, less than 30 amino acid substitutions, deletions or insertions. In a specific embodiment, an immunogenic composition of the invention comprises a polypeptide comprising the amino acid sequence of residues 1-327 of SEQ ID NO:6 or 8. In another embodiment, an immunogenic composition of the invention comprises a polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of residues 1-327 of SEQ ID NO:6 or 8. In a further embodiment, an immunogenic composition of the invention comprises a polypeptide comprising the amino acid sequence of residues 1-327 of SEQ NO:6 or 8 comprising less than 3, less than 5, less then 10, less then 15, less than 20, less than 25, less than 30 amino acid substitutions, deletions or insertions.

In one embodiment, an immunogenic composition of the invention is a monovalent immunogenic composition comprising a single reassortant influenza virus. In one embodiment, an immunogenic composition of the invention is a trivalent immunogenic composition comprising three reassortant influenza viruses. In one embodiment, an immunogenic composition of the invention is a trivalent immunogenic composition comprising two reassortant influenza A viruses and a reassortant influenza B virus. In one embodiment, an immunogenic composition of the invention is a trivalent immunogenic composition comprising a reassortant influenza A virus of the H1 type, a reassortant influenza A virus of the H3 type and a reassortant influenza B virus. In another embodiment, an immunogenic composition of the invention is a tetravalent immunogenic composition comprising four reassortant influenza viruses. In one embodiment, an immunogenic composition of the invention is a tetravalent immunogenic composition comprising two reassortant influenza A viruses and two reassortant influenza B viruses. In one embodiment, an immunogenic composition of the invention is a tetravalent immunogenic composition comprising a reassortant influenza A virus of the H1 type, a reassortant influenza A virus of the H3 type, a reassortant influenza B virus of the Victoria lineage and a reassortant influenza B virus of the Yamagata lineage. In a specific embodiment, an immunogenic composition of the invention comprises a reassortant or recombinant influenza virus comprising a genome segment encoding an HA polypeptide comprising the amino acid sequence of SEQ ID NO:6 or 8. In another embodiment, an immunogenic composition of the invention comprises a reassortant or recombinant influenza virus comprising a genome segment encoding an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of SEQ NO:6 or 8. In a further embodiment, an immunogenic composition of the invention comprises a reassortant or recombinant influenza virus comprising a genome segment encoding an HA polypeptide comprising the amino acid sequence of SEQ NO:6 or 8 comprising less than 3, less than 5, less then 10, less then 15, less than 20, less than 25, less than 30 amino acid substitutions, deletions or insertions. In a specific embodiment, an immunogenic composition of the invention comprises a reassortant or recombinant influenza virus comprising a genome segment encoding an HA polypeptide comprising the amino acid sequence of residues 1-327 of SEQ NO:6 or 8. In another embodiment, an immunogenic composition of the invention comprises a reassortant or recombinant influenza virus comprising a genome segment encoding an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of residues 1-327 SEQ NO:6 or 8. In a further embodiment, an immunogenic composition of the invention comprises a reassortant or recombinant influenza virus comprising a genome segment encoding an HA polypeptide comprising the amino acid sequence of residues 1-327 of SEQ ID NO:6 or 8 comprising less than 3, less than 5, less then 10, less then 15, less than 20, less than 25, less than 30 amino acid substitutions, deletions or insertions.

Additionally, the invention encompasses a reassortant influenza virus that comprises a genome segment encoding one or more of the polypeptides described above. Further, the invention encompasses immunogenic compositions comprising an immunologically effective amount of such reassortant influenza virus. Methods for stimulating the immune system of an individual to produce a protective immune response against influenza virus comprising administering an immunologically effective amount of such reassortant influenza virus in a physiologically acceptable carrier are also part of the invention. In one embodiment, a reassortant influenza virus of the invention is a 6:2 reassortant virus comprising 6 internal genome segments from one or more donor virus (e.g. A/AA/6/60 or A/Puerto Rico/8/34, which is more commonly known as PR8) and further comprising 2 genome segments (typically and preferably encoding HA and NA or fragments thereof). Immunogenic compositions comprising such reassortant (recombinant) virus are also features of the invention.

In one embodiment, a reassortant or recombinant influenza virus of the invention comprises 6 internal genome segments of A/Ann Arbor/6/60 and a genome segment encoding an HA polypeptide. The HA polypeptide may comprise the amino acid sequence of SEQ ID NO:1 having at least one substitution, deletion or insertion. The HA polypeptide may comprise the amino acid sequence of SEQ ID NO:1 having the H273Y substitution. The HA polypeptide may comprise the amino acid sequence of SEQ ID NO:1 having the D222G and/or Q223R substitution. The HA polypeptide may comprise the amino acid sequence of SEQ ID NO:1 having at least one amino acid substitution selected from the group consisting of K119E, K119N and A186D. In a specific embodiment, a reassortant or recombinant influenza virus of the invention comprises 6 internal genome segments of A/Ann Arbor/6/60 and a genome segment encoding an HA polypeptide comprising the amino acid sequence of SEQ ID NO:1 having the D222G, K119E and A186D substitutions. In a specific embodiment, a reassortant or recombinant influenza virus of the invention comprises 6 internal genome segments of A/Ann Arbor/6/60 and a genome segment encoding an HA polypeptide comprising the amino acid sequence of SEQ ID NO:1 having Q223R and A186D substitutions. In a specific embodiment, a reassortant or recombinant influenza virus of the invention comprises 6 internal genome segments of A/Ann Arbor/6/60 and a genome segment encoding an HA polypeptide comprising the amino acid sequence of SEQ ID NO:1 having Q223R, H273Y and A186D substitutions. In a specific embodiment, a reassortant or recombinant influenza virus of the invention comprises 6 internal genome segments of A/Ann Arbor/6/60 and an HA genome segment encoding an HA polypeptide comprising the amino acid sequence of SEQ NO:6 or 8. In a specific embodiment, the HA genome segment may encode an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of SEQ ID NO:6 or 8. In a specific embodiment, the HA genome segment may encode an HA polypeptide comprising the amino acid sequence of SEQ NO:6 or 8 comprising less than 3, less than 5, less then 10, less then 15, less than 20, less than 25, less than 30 amino acid substitutions, deletions or insertions. In a specific embodiment, the HA genome segment may encode an HA polypeptide comprising the amino acid sequence of residues 1-327 SEQ ID NO:6 or 8. In a specific embodiment, the HA genome segment may encode an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of residues 1-327 SEQ ID NO:6 or 8. In a specific embodiment, the HA genome segment may encode an HA polypeptide comprising the amino acid sequence of residues 1-327 SEQ ID NO:6 or 8 comprising less than 3, less than 5, less then 10, less then 15, less than 20, less than 25, less than 30 amino acid substitutions, deletions or insertions.

In one embodiment, a reassortant or recombinant influenza virus of the invention comprises 6 internal genome segments of A/Puerto Rico/8/34 (PR8) and a genome segment encoding an HA polypeptide. The HA polypeptide may comprise the amino acid sequence of SEQ ID NO:1 having at least one substitution, deletion or insertion. The HA polypeptide may comprise the amino acid sequence of SEQ ID NO:1 having the D222G and/or Q223R substitution. The HA polypeptide may comprise the amino acid sequence of SEQ ID NO:1 having at least one amino acid substitution selected from the group consisting of K119E, K119N and A186D. The HA polypeptide may comprise the amino acid sequence of SEQ ID NO:1 having the H273Y substitution. In a specific embodiment, a reassortant or recombinant influenza virus of the invention comprises 6 internal genome segments of A/Puerto Rico/8/34 (PR8) and a genome segment encoding an HA polypeptide comprising the amino acid sequence of SEQ NO:1 having the D2220, K119E and A186D substitutions. In a specific embodiment, a reassortant or recombinant influenza virus of the invention comprises 6 internal genome segments of A/Puerto Rico/8/34 (PR8) and a genome segment encoding an HA polypeptide comprising the amino acid sequence of SEQ ID NO:1 having the Q223R and A186D substitutions. In a specific embodiment, a reassortant or recombinant influenza virus of the invention comprises 6 internal genome segments of A/Puerto Rico/8/34 (PR8) and a genome segment encoding an HA polypeptide comprising the amino acid sequence of SEQ ID NO:1 having the Q223R, H273Y and A186D substitutions. In a specific embodiment, a reassortant or recombinant influenza virus of the invention comprises 6 internal genome segments of A/Puerto Rico/8/34 (PR8) and an HA genome segment encoding an HA polypeptide comprising the amino acid sequence of SEQ NO:6 or 8. In a specific embodiment, the HA genome segment may encode an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of SEQ ID NO:6 or 8. In a specific embodiment, the HA genome segment may encode an HA polypeptide comprising the amino acid sequence of SEQ ID NO:6 or 8 comprising less than 3, less than 5, less then 10, less then 15, less than 20, less than 25, less than 30 amino acid substitutions, deletions or insertions. In a specific embodiment, the HA genome segment may encode an HA polypeptide comprising the amino acid sequence of residues 1-327 SEQ ID NO:6 or 8. In a specific embodiment, the HA genome segment may encode an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of residues 1-327 SEQ NO:6 or 8. In a specific embodiment, the HA genome segment may encode an HA polypeptide comprising the amino acid sequence of residues 1-327 SEQ ID NO:6 or 8 comprising less than 3, less than 5, less then 10, less then 15, less than 20, less than 25, less than 30 amino acid substitutions, deletions or insertions.

Also within the invention are reassortant influenza viruses comprising a polynucleotide encoding a polypeptide of the invention. In one embodiment such reassortant viruses are 6:2 reassortant viruses comprising 6 internal genome segments from one or more donor virus (e.g., A/AA/6/60 or A/Puerto Rico/8/34), a first genome segment encoding a hemagglutinin polypeptide of the invention, and a second genome segment encoding a neuramidinase polypeptide. Immunogenic compositions comprising immunologically effective amounts of such a reassortant/recombinant influenza virus are also within purview of the current invention.

Reassortant or recombinant viruses of the invention display high rate of replication in tissue cultures or embryonated eggs. In one embodiment, a reassortant or recombinant influenza virus grows to a titer of at least about 7.5 $\log_{10}$ PFU/ml, at least about 8 $\log_{10}$ PFU/ml, at least about 8.5 $\log_{10}$ PFU/ml, at least about 9 $\log_{10}$ PFU/ml, at least about 9.5 $\log_{10}$ PFU/ml, at least about 10 $\log_{10}$ PFU/ml, at least about 10.5 $\log_{10}$ PFU/ml or at least about 11 $\log_{10}$ PFU/ml in embryonated eggs. In another embodiment, a reassortant or recombinant influenza virus grows to a titer of at least about 7.5 $\log_{10}$ PFU/ml, at least about 8 $\log_{10}$ PFU/ml, at least about 8.5 $\log_{10}$ PFU/ml, at least about 9 $\log_{10}$ PFU/ml, at least about 9.5 $\log_{10}$ PFU/ml, at least about 10 $\log_{10}$ PFU/ml, at least about 10.5 $\log_{10}$ PFU/ml or at least about 11 $\log_{10}$ PFU/ml in tissue cultures.

Methods of producing a reassortant/recombinant influenza virus through culturing a host cell harboring a polynucleotide of the invention are also contemplated.

In other embodiments herein, the invention comprises immunogenic compositions having an immunologically effective amount of one or more of the above described reassortant influenza viruses of the invention. In one embodiment, an immunogenic composition of the invention comprises a live virus of the invention. Other embodiments include methods for stimulating the immune system of an individual to produce a protective immune response against influenza virus comprising administering to the individual an immunologically effective amount of one or more of the reassortant influenza viruses described above (optionally in a physiologically effective carrier).

The invention also encompasses vaccines comprising a recombinant or reassortant influenza virus of the invention. In one embodiment, a vaccine of the invention is a split vaccine or killed vaccine. In another embodiment, a vaccine of the invention is a live attenuated influenza virus vaccine. In a further embodiment, a vaccine of the invention may be a monovalent, bivalent, trivalent or tetravalent vaccine.

Methods of producing an influenza virus vaccine are also included in the invention. In one embodiment, a vaccine of the invention may be a monovalent, bivalent, trivalent or tetravalent vaccine.

The present invention also relates to methods and compositions for increasing the replication capacity of influenza viruses in, for example, embryonated hens' eggs and/or cell culture. The invention is based, in part, on the identification of particular H1 protein amino acids associated with increased replication capacity. By using an H1 HA gene encoding an H1 HA protein that comprises one or more of these particular amino acids, improved influenza viral yields can be achieved. In one embodiment, a method is provided for increasing the replication capacity of a reassortant or recombinant influenza virus comprising altering an amino acid residue of the hemagglutinin polypeptide at a position corresponding to the amino acid residue of position 119 or 186 of SEQ ID NO: 1, thereby increasing the replication capacity of the reassortant or recombinant influenza virus. A recombinant influenza virus produced by the method is also provided.

The present invention also relates to methods and compositions for increasing the replication capacity of H1N1 reassortant influenza viruses in, for example, embryonated hens' eggs and/or cell culture. In one embodiment, a method is provided for increasing the replication capacity of a H1N1 reassortant or recombinant influenza virus comprising altering an amino acid residue of the hemagglutinin polypeptide at a position corresponding to the amino acid residue of position 119 or 186 of SEQ ID NO: 1, thereby increasing the replication capacity of the reassortant or recombinant influenza virus. A recombinant influenza virus produced by the method is also provided.

In one embodiment, the replication capacity of a reassortant or recombinant influenza virus of the invention, which comprises a hemagglutinin polypeptide of the invention having noon naturally occurring amino acid is increased at least 2-fold, at least 4-fold, at least 6-fold, at least 8-fold, at least 10-fold, at least 20-fold, at least 40-fold, at least 50-fold, or at least 100-fold relative to the same reassortant or recombinant influenza virus not comprising a non naturally occurring amino acid at the same position. In another embodiment, the replication capacity of a reassortant or recombinant influenza virus of the invention, which comprises a hemagglutinin polypeptide of the invention having a non naturally occurring amino acid is increased at between 2-fold and 10-fold, between 2-fold and 20-fold, between 2-fold and 40-fold, between 2-fold and 100-fold, between 5-fold and 10-fold, between 5-fold and 20-fold, between 5-fold and 40-fold, or between 5-fold and 100-fold relative to the same reassortant or recombinant influenza virus not comprising a non naturally occurring amino acid at the same position.

In one embodiment, the peak titer in embryonated eggs for a reassortant or recombinant influenza virus of the invention, which comprises a hemagglutinin polypeptide of the invention having anon naturally occurring amino acid is increased at least 2-fold, at least 4-fold, at least 6-fold, at least 8-fold, at least 10-fold, at least 20-fold, at least 40-fold, at least 50-fold, or at least 100-fold relative to the same reassortant or recombinant influenza virus not comprising a non naturally occurring amino acid at the same position. In another embodiment, the peak titer in embryonated eggs for a reassortant or recombinant influenza virus of the invention, which comprises a hemagglutinin polypeptide of the invention having a non naturally occurring amino acid is increased at between 2-fold and 10-fold, between 2-fold and 20-fold, between 2-fold and 40-fold, between 2-fold and 100-fold, between 5-fold and 10-fold, between 5-fold and 20-fold, between 5-fold and 40-fold, or between 5-fold and 100-fold relative to the same reassortant or recombinant influenza virus not comprising a non naturally occurring amino acid at the same position.

In a specific embodiment, a recombinant influenza virus is provided which comprises an HA polypeptide of an H1N1 virus which polypeptide comprises an amino acid selected from the group consisting of K119E, K119N and A186D. In a specific embodiment, a recombinant influenza virus is provided which comprises an HA polypeptide of an H1N1 virus which polypeptide comprises an amino acid selected from the group consisting of K119X and A186X, wherein X is any amino acid not naturally occurring in said H1N1 virus. In a specific embodiment, the recombinant influenza viruses of the invention are 6:2 reassortant viruses comprising at least 5 or 6 segments of (or derived from) an attenuated virus. In a specific embodiment, the recombinant influenza viruses of the invention are 6:2 reassortant viruses comprising at least 5 or 6 segments of (or derived from) an attenuated virus selected from the group consisting of Ann Arbor/6/60, A/Puerto Rico/8/34, A/Leningrad/134/17/57, and A/Leningrad/17. In a specific embodiment, the recombinant influenza viruses of the invention comprise an HA polypeptide comprising the amino acid sequence of SEQ ID NO:6 or 8. In another embodiment, the recombinant influenza viruses of the invention comprise an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of SEQ ID NO:6 or 8. In a further embodiment, the recombinant influenza viruses of the invention comprise an HA polypeptide comprising the amino acid sequence of SEQ ID NO:6 or 8 comprising less than 3, less than 5, less then 10, less then 15, less than 20, less than 25, less than 30 amino acid substitutions, deletions or insertions. In a specific embodiment, the recombinant influenza viruses of the invention comprise an HA polypeptide comprising the amino acid sequence of residues 1-327 of SEQ NO:6 or 8. In another embodiment, the recombinant influenza viruses of the invention comprise an HA polypeptide comprising: an amino acid sequence having at least 95%, at least 98%, at least 98.5%, at least 99%, at least 99.2%, at least 99.4%, at least 99.6%, at least 99.8% or at least 99.9% sequence identity to the amino acid sequence of residues 1-327 of SEQ ID NO:6 or 8. In a further embodiment, the recombinant influenza viruses of the invention comprise an HA polypeptide comprising the amino acid sequence of residues 1-327 of SEQ ID NO:6 or 8 comprising less than 3, less than 5, less then 10, less then 15, less than 20, less than 25, less than 30 amino acid substitutions, deletions or insertions.

In a specific embodiment, the recombinant influenza viruses of the invention are 6:2, or 7:1 reassortant viruses comprising an HA polypeptide of the invention. In a specific embodiment, the recombinant influenza viruses of the invention are 6:2, or 7:1 reassortant viruses comprising an HA polypeptide of the invention and at least 5 or 6 segments of (or derived from) an attenuated virus selected from the group consisting of: A/Ann Arbor/6/60, A/Puerto Rico/8/34, A/Leningrad/134/17/57, and A/Leningrad/17. In one embodiment, the recombinant influenza viruses of the invention comprise an HA polypeptide of (or derived from) A/CA/04/09 or A/CA/07/09 having 1, 2, or 3 substitutions at positions 119, 186). In one embodiment, the recombinant influenza viruses of the invention comprise an HA polypeptide of (or derived from) A/CA/04/09 or A/CA/07/09 having a glutamic acid or an asparagine at amino acid position 119 and an aspartic acid at position 186. In one embodiment, the recombinant influenza viruses of the invention comprise an HA polypeptide of (or derived from) A/CA/04/09 or A/CA/07/09 having an amino acid substitution at amino acid position 119 and position 186. In one embodiment, the recombinant influenza viruses of the invention comprise an HA polypeptide of (or derived from) an H1N1 swine flu virus having an amino acid substitution at amino acid position 119 and position 186. In a specific embodiment, the recombinant influenza viruses of the invention comprise an HA polypeptide comprising the amino acid sequence of SEQ ID NO:6 or 8. In another embodiment, the recombinant influenza viruses of the invention comprise an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of SEQ ID NO:6 or 8. In a further embodiment, the recombinant influenza viruses of the invention comprise an HA polypeptide comprising the amino acid sequence of SEQ ID NO:6 or 8 comprising less than 3, less than 5, less then 10, less then 15, less than 20, less than 25, less than 30 amino acid substitutions, deletions or insertions. In a specific embodiment, the recombinant influenza viruses of the invention comprise an HA polypeptide comprising the amino acid sequence of residues 1-327 of SEQ ID NO:6 or 8. In another embodiment, the recombinant influenza viruses of the invention comprise an HA polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of residues 1-327 SEQ ID NO:6 or 8. In a further embodiment, the recombinant influenza viruses of the invention comprise an HA polypeptide comprising the amino acid sequence of residues 1-327 of SEQ NO:6 or 8 comprising less than 3, less than 5, less then 10, less then 15, less than 20, less than 25, less than 30 amino acid substitutions, deletions or insertions.

One skilled in the art will recognize that the exact position of an amino acid can vary depending on the particular influenza strain used in the vectors, methods, and viruses of the invention. For example, the HA protein of a particular influenza strain may comprise an insertion or deletion in the HA gene encoding the HA protein such that the position corresponding to position 119 of SEQ NO:1 is found at, for example, residue 93 or 97 of the HA protein of that particular influenza strain. In particular, as shown in Table 3, position 119 and 186 of the A/CA/07/09 HA polypeptide (SEQ ID NO:1) corresponds to position 118 and 185, respectively of the A/South Dakota/6/07 H1 HA polypeptide. One skilled in the art can readily recognize whether a particular amino acid position corresponds to a position that, when altered, is associated with increased replication capacity using techniques conventional to the art. One such conventional technique is to align the amino acid sequence of SEQ ID NO:1 and the particular influenza strain HA polypeptide using algorithms available in the art.

These and other objects and features of the invention will become more fully apparent when the following detailed description is read in conjunction with the accompanying figures and claims.

BRIEF DESCRIPTION OF THE FIGURES

FIG. 2. HA1 protein sequence comparison of A/California/7/09. A/Swine/Iowa/1/1976 (nucleotide sequence accession code CY022069), A/Swine/1931 (nucleotide sequence accession code CY009628), and A/South Dakota/6/07. The amino acids at positions 119, 153, 154, 155, 186 and 278 are highlighted.

DEFINITIONS

Figure 1A:
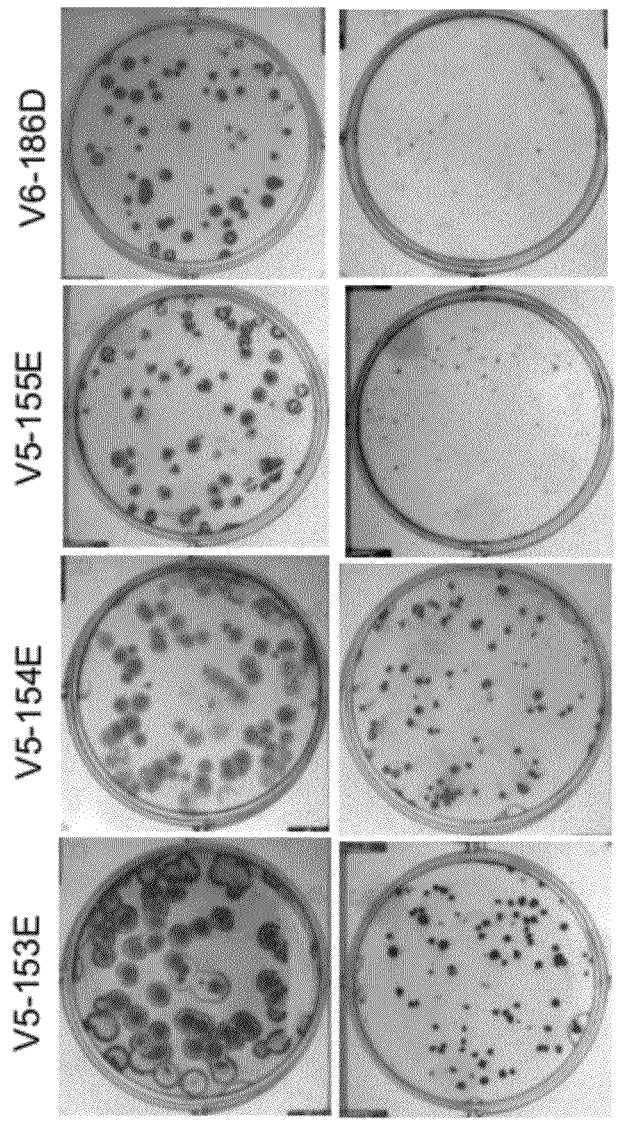
FIG. 1. Plaque morphology of variants selected from MDCK cells and the indicated variants containing introduced amino acid changes (A). Plaque assay was performed in MDCK cells, incubated at 33° C. for 4 days and immunostained with polyclonal antiserum against influenza A virus. The plaque morphology of double mutant V5-119E/186D is compared with single 119E and 186D mutant in panel B.

Unless defined otherwise, all technical and scientific terms used herein have the same meaning as commonly understood by one of ordinary skill in the art to which the invention pertains. The following definitions supplement those in the art and are directed to the current application and are not necessarily to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting. Additional terms are defined and described throughout.

The phrase "substantially identical," in the context of two nucleic acids or polypeptides (e.g., DNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection.

The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "non-conservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software. Examples of conservative substitutions are also described herein.

The "neuraminidase" polypeptides of the invention show immunological cross reactivity with one or more known neuraminidase molecule from an influenza virus. The literature is replete with examples of such known neuraminidases (e.g., GenBank, publications from the CDC, etc.). Similarly, the "hemagglutinin" polypeptides of the invention may show immunological cross-reactivity with one or more known hemagglutinin molecule from an influenza virus. Again, the literature is replete with examples of such known hemagglutinin molecules.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "tissue specific" promoter or enhancer is one that regulates transcription in a specific tissue type or cell type, or types.

Expression of a gene" or "expression of a nucleic acid" typically means transcription of DNA into RNA (optionally including modification of the RNA, e.g., splicing) or transcription of RNA into mRNA, translation of RNA into a polypeptide (possibly including subsequent modification of the polypeptide, e.g., post-translational modification), or both transcription and translation, as indicated by the context.

An "open reading frame" or "ORF" is a possible translational reading frame of DNA or RNA (e.g., of a gene), which is capable of being translated into a polypeptide. That is, the reading frame is not interrupted by stop codons. However, it should be noted that the term ORF does not necessarily indicate that the polynucleotide is, in fact, translated into a polypeptide.

The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids.

An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

A "bi-directional expression vector" is characterized by two alternative promoters oriented in the opposite direction relative to a nucleic acid situated between the two promoters, such that expression can be initiated in both orientations resulting in, e.g., transcription of both plus (+) or sense strand, and negative (−) or antisense strand RNAs.

In the context of the invention, the term "isolated" refers to a biological material, such as a virus, a nucleic acid or a protein, which is substantially free from components that normally accompany or interact with it in its naturally occurring environment. The isolated biological material optionally comprises additional material not found with the biological material in its natural environment, e.g., a cell or wild-type virus. For example, if the material is in its natural environment, such as a cell, the material can have been placed at a location in the cell (e.g., genome or genetic element) not native to such material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids. An isolated virus, for example, is in an environment (e.g., a cell culture system, or purified from cell culture) other than the native environment of wild-type virus (e.g., the nasopharynx of an infected individual).

The term "chimeric" or "chimera," when referring to a virus, indicates that the virus includes genetic and/or polypeptide components derived from more than one parental viral strain or source. Similarly, the term "chimeric" or "chimera," when referring to a viral protein, indicates that the protein includes polypeptide components (i.e., amino acid subsequences) derived from more than one parental viral strain or source. As will be apparent herein, such chimeric viruses are typically reassortant/recombinant viruses. Thus, in some embodiments, a chimera can optionally include, e.g., a sequence (e.g., of HA and/or NA) from an A influenza virus placed into a backbone comprised of, or constructed/derived from a B influenza virus (e.g., B/AA/1/66, etc) or a B influenza virus sequence placed into an A influenza virus backbone (i.e., donor virus) such as, e.g., A/AA/6/60, etc.

The term "recombinant" indicates that the material (e.g., a nucleic acid or protein) has been artificially or synthetically (non-naturally) altered by human intervention. The alteration can be performed on the material within, or removed from, its natural environment or state. Specifically. e.g., an influenza virus is recombinant when it is produced by the expression of a recombinant nucleic acid. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

The term "reassortant," when referring to a virus (typically herein, an influenza virus), indicates that the virus includes genetic and/or polypeptide components derived from more than one parental viral strain or source. For example, a 7:1 reassortant includes 7 viral genome segments (or gene segments) derived from a first parental virus, and a single complementary viral genome segment, e.g., encoding a hemagglutinin or neuraminidase described herein. A 6:2 reassortant includes 6 genome segments, most commonly the 6 internal genome segments from a first parental virus, and two complementary segments, e.g., hemagglutinin and neuraminidase genome segments, from one or more different parental virus. Reassortant viruses can also, depending upon context herein, be termed as "chimeric" and/or "recombinant."

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation," and "transduction." In the context of the invention a variety of methods can be employed to introduce nucleic acids into cells, including electroporation, calcium phosphate precipitation, lipid mediated transfection (lipofection), etc.

The term "host cell" means a cell that contains a heterologous nucleic acid, such as a vector or a virus, and supports the replication and/or expression of the nucleic acid. Host cells can be prokaryotic cells such as E. coli, or eukaryotic cells such as yeast, insect, amphibian, avian or mammalian cells, including human cells. Exemplary host cells can include, e.g., Vero (African green monkey kidney) cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), and COS cells (e.g., COS1, COS7 cells), etc. In other embodiments, host cells can optionally include eggs (e.g., hen eggs, embryonated hen eggs, etc.).

An "immunologically effective amount" of influenza virus is an amount sufficient to enhance an individual's (e.g., a human's) own immune response against a subsequent exposure to influenza virus. Levels of induced immunity can be monitored, e.g., by measuring amounts of neutralizing secretory and/or serum antibodies, e.g., by plaque neutralization, complement fixation, enzyme-linked immunosorbent, or microneutralization assay.

A "protective immune response" against influenza virus refers to an immune response exhibited by an individual (e.g., a human) that is protective against disease when the individual is subsequently exposed to and/or infected with wild-type influenza virus. In some instances, the wild-type (e.g., naturally circulating) influenza virus can still cause infection, but it cannot cause a serious or life-threatening infection. Typically, the protective immune response results in detectable levels of host engendered serum and secretory antibodies that are capable of neutralizing virus of the same strain and/or subgroup (and possibly also of a different, non-vaccine strain and/or subgroup) in vitro and in vivo.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes. IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see Fundamental Immunology, W. E. Paul, ed., Raven Press, N.Y. (1999) for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include, e.g., polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Influenza Virus

The polypeptides and polynucleotides of the invention are variants of influenza HA and/or NA sequences. See, e.g., the Sequence Listing in FIGS. 1 and 2 below. In general, influenza viruses are made up of an internal ribonucleoprotein core containing a segmented single-stranded RNA genome and an outer lipoprotein envelope lined by a matrix protein. The genome of influenza viruses is composed of eight segments of linear (−) strand ribonucleic acid (RNA), encoding the immunogenic hemagglutinin (HA) and neuraminidase (NA) proteins, and six internal core polypeptides: the nucleocapsid nucleoprotein (NP); matrix proteins (M); non-structural proteins (NS); and 3 RNA polymerase (PA, PB1, PB2) proteins. During replication, the genomic viral RNA is transcribed into (+) strand messenger RNA and (−) strand genomic cRNA in the nucleus of the host cell. Each of the eight genomic segments is packaged into ribonucleoprotein complexes that contain, in addition to the RNA, NP and a polymerase complex (PB1, PB2, and PA). The hemagglutinin molecule consists of a surface glycoprotein and acts to bind to N-AcetylNeuraminic acid (NeuNAc), also known as sialic acid, on host cell surface receptors. In some embodiments herein, the polypeptides of the invention (and polypeptides encoded by the polynucleotides of the invention) can act to bind NeuNAc whether in vitro or in vivo. Such action can in some embodiments also be done by fragments of hemagglutinin which retain hemagglutinin activity. Hemagglutinin is made up of two subunits, HA1 and HA2 and the entire structure is about 550 amino acids in length and about 220 kD. Neuraminidase molecules cleave terminal sialic acid residues from cell surface receptors of influenza virus, thereby releasing virions from infected cells. Neuraminidase also removes sialic acid from newly made hemagglutinin and neuraminidase molecules. In some embodiments herein, the polypeptides of the invention (and polypeptides encoded by the polynucleotides of the invention) can act to cleave sialic acid residues whether in vitro or in vivo. This action can also be done in some embodiments by fragments of neuraminidase which retain neuraminidase activity. The neuraminidase polypeptides of the invention show immunological cross reactivity with one or more known neuraminidase molecule from an influenza virus. The literature is replete with examples of such known neuraminidases (e.g., in GenBank, in publications from the CDC, etc.). Similarly, the hemagglutinin polypeptides of the invention show immunological cross-reactivity with one or more known hemagglutinin molecule from an influenza virus. Again, the literature is replete with examples of such known hemagglutinin molecules.

Influenza is commonly grouped into influenza A and influenza B categories, as well as a typically less important C category. Influenza A and influenza B viruses each contain eight segments of single stranded RNA with negative polarity. The influenza A genome encodes eleven polypeptides. Segments 1-3 encode three polypeptides, making up a RNA-dependent RNA polymerase. Segment 1 encodes the polymerase complex protein PB2. The remaining polymerase proteins PD1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants. The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a bicistronic mRNA. Segment 7 of influenza B also encodes two proteins: M1 and BM2. The smallest segment encodes two products: NS1 is translated from the full length RNA, while NS2 is translated from a spliced mRNA variant.

Influenza types A and B are typically associated with influenza outbreaks in human populations. However, type A influenza also infects other species as well, e.g., birds, pigs, and other animals. The type A viruses are categorized into subtypes based upon differences within their hemagglutinin and neuraminidase surface glycoprotein antigens. Hemagglutinin in type A viruses has 16 known subtypes and neuraminidase has 9 known subtypes. In humans, currently only about 4 different hemagglutinin and 2 different neuraminidase subtypes are known, e.g., H1, H2, H3, H5, N1, and N2. In particular, two major subtypes of influenza A have been active in humans, namely, H1N1 and H13N2. H1N2, however has recently been of concern. Influenza B viruses are not divided into subtypes based upon their hemagglutinin and neuraminidase proteins.

Different strains of influenza can be categorized based upon, e.g., the ability of influenza to agglutinate red blood cells (RBCs or erythrocytes). Antibodies specific for particular influenza strains can bind to the virus and, thus, prevent such agglutination. Assays determining strain types based on such inhibition are typically known as hemagglutinin inhibition assays (HI assays or HAI assays) and are standard and well known methods in the art to characterize influenza strains. Of course, those of skill in the art will be familiar with other assays, e.g., ELISA, indirect fluorescent antibody assays, immunohistochemistry, Western blot assays, etc. with which to characterize influenza strains and the use of and discussion herein of HI assays should not be necessarily construed as limiting.

Briefly, in typical HI assays, sera to be used for typing or categorization, which is often produced in ferrets, is added to erythrocyte samples in various dilutions, e.g., 2-fold, etc. Optical determination is then made whether the erythrocytes are clumped together (i.e., agglutinated) or are suspended (i.e., non-agglutinated). If the cells are not clumped, then agglutination did not occur due to the inhibition from antibodies in the sera that are specific for that influenza. Thus, the types of influenza are defined as being within the same strain. In some cases, one strain is described as being "like" the other, e.g., strain x is a "y-like" strain, etc. For example, if two samples are within four-fold titer of one another as measured by an HI assay, then they can be described as belonging to the same strain (e.g., both belonging to the "New Caledonia" strain or both being "Moscow-like" strains, etc.). In other words, strains are typically categorized based upon their immunologic or antigenic profile. An HAI titer is typically defined as the highest dilution of a serum that completely inhibits hemagglutination. See, e.g., Schild, et al., Bull. Wld Hlth Org., 1973, 48:269-278, etc. Again, those of skill in the art will be quite familiar with categorization and classification of influenza into strains and the methods to do so.

From the above it will be appreciated that the current invention not only comprises the specific sequences listed herein, but also such sequences within various vectors (e.g., ones used for plasmid reassortment and rescue, see below) as well as hemagglutinin and neuraminidase sequences within the same strains as the sequences listed herein. Also, such same strains that are within various vectors (e.g., typically ones used for plasmid reassortment and rescue such as A/Ann Arbor/6/60 or B/Ann Arbor/1/66, A/Puerto Rico/8/34, B/Leningrad/14/17/55, B/14/5/1, B/USSR/60/69, B/Leningrad/179/86, B/Leningrad/14/55, or B/England/2608/76, etc.) are also included.

As used herein, the term "similar strain" should be taken to indicate that a first influenza virus is of the same or related strain as a second influenza virus. In typical embodiments such relation is commonly determined through use of an HAI assay. Influenza viruses that fall within a four-fold titer of one another in an HAI assay are, thus, of a "similar strain." Those of skill in the art, however, will be familiar with other assays, etc. to determine similar strains, e.g., FRID, neutralization assays, etc. The current invention also comprises such similar strains (i.e., strains similar to the ones present in sequence listing herein) in the various plasmids, vectors, viruses, methods, etc. herein. Thus, unless the context clearly dictates otherwise, descriptions herein of particular sequences (e.g., those in the sequence listing) or fragments thereof also should be considered to include sequences from similar strains to those similar strains to those strains having the sequences in those plasmids, vectors, viruses, etc. herein). Also, it will be appreciated that the NA and HA polypeptides within such similar strains are, thus, "similar polypeptides" when compared between "similar strains."

Influenza Virus Vaccines

The sequences, compositions and methods herein are primarily, but not solely, concerned with production of influenza viruses for vaccines. Historically, influenza virus vaccines have primarily been produced in embryonated hen eggs using strains of virus selected or based on empirical predictions of relevant strains. More recently, reassortant viruses have been produced that incorporate selected hemagglutinin and/or neuraminidase antigens in the context of an approved attenuated, temperature sensitive master strain. Following culture of the virus through multiple passages in hen eggs, influenza viruses are recovered and, optionally, inactivated, e.g., using formaldehyde and/or β-propiolactone (or alternatively used in live attenuated vaccines). Thus, it will be appreciated that HA and NA sequences (as in the current invention) are quite useful in constructing influenza vaccines.

Attempts at producing recombinant and reassortant vaccines in cell culture have been hampered by the inability of some of the strains approved for vaccine production to grow efficiently under standard cell culture conditions. However, prior work by the inventors and their coworkers provided a vector system, and methods for producing recombinant and reassortant viruses in culture, thus, making it possible to rapidly produce vaccines corresponding to one or many selected antigenic strains of virus, e.g., either A or B strains, various subtypes or substrains, etc., e.g., comprising the HA and NA sequences herein. See, U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus." Typically, the cultures are maintained in a system, such as a cell culture incubator, under controlled humidity and $CO_2$, at constant temperature using a temperature regulator, such as a thermostat to insure that the temperature does not exceed 35° C. Reassortant influenza viruses can be readily obtained by introducing a subset of vectors corresponding to genomic segments of a master influenza virus, in combination with complementary segments derived from strains of interest (e.g., HA and NA antigenic variants herein). Typically, the master strains are selected on the basis of desirable properties relevant to vaccine administration. For example, for vaccine production, e.g., for production of a live attenuated vaccine, the master donor virus strain may be selected for an attenuated phenotype, cold adaptation and/or temperature sensitivity. As explained elsewhere herein and, e.g., in U.S. patent application Ser. No. 10/423,828, etc., various embodiments of the invention utilize A/Ann Arbor (AA)/6/60 or B/Ann Arbor/1/66 or A/Puerto Rico/8/34, or B/Leningrad/14/17/55, B/14/5/1, B/USSR/60/69, a/Leningrad/179/86, B/Leningrad/14/55, or B/England/2608/76 influenza strain as a "backbone" upon which to add HA and/or NA genes (e.g., such as those sequences listed herein, etc) to create desired reassortant viruses. Thus, for example, in a 6:2 reassortant, 2 genes (i.e., NA and HA) would be from the influenza strain(s) against which an immunogenic reaction is desired, while the other 6 genes would be from the Ann Arbor strain, or other backbone strain, etc. The Ann Arbor virus is useful for its cold adapted, attenuated, temperature sensitive attributes. Of course, it will be appreciated that the HA and NA sequences herein are capable of reassortment with a number of other virus genes or virus types (e.g., a number of different "backbones" such as A/Puerto Rico/8/34, etc., containing the other influenza genes present in a reassortant, namely, the non-HA and non-NA genes). Live, attenuated influenza A virus vaccines against human influenza viruses were recently licensed in the United States. See above. Such vaccines are reassortant H1N1 and H1N2 viruses in which the internal protein genes of A/Ann Arbor (AA)/6/60 (H2N2) cold adapted (ca) virus confer the cold adapted, attenuation and temperature sensitive phenotypes of the AA ca virus on the reassortant viruses (i.e., the ones having the hemagglutinin and neuraminidase genes from the non-Ann Arbor strain). In some embodiments herein, the reassortants can also comprise 7:1 reassortants. In other words, only the HA or the NA is not from the backbone or MDV strain. Previous work has been reported with suitable backbone donor virus strains that optionally are within various embodiments of the current invention. See, e.g., U.S. Application No. 60/420,708, filed Oct. 23, 2002, U.S. application Ser. No. 10/423,828, filed Apr. 25, 2003, and U.S. Application No. 60/574,117, filed May 25, 2004, all entitled "Multi-Plasmid System for the Production of Influenza Virus"; Maassab et al., J. of Inf. Dis., 1982, 146:780-790; Cox, et al., Virology, 1988, 167:554-567; Wareing et al., Vaccine, 2001, 19:3320-3330; Clements, et al., J Infect Dis., 1990, 161(5):869-77, etc.

In some embodiments, the sequences herein can optionally have specific regions removed (both or either in the nucleic acid sequence or the amino acid sequence). For example, for those molecules having polybasic cleavage site, such sites can optionally be removed. Such cleavage sites, in some embodiments herein, are, e.g., modified or altered in their sequences in comparison to the wild-type sequences from which such sequences are derived (e.g., to disable the cleavage or reduce the cleavage there, etc.). Such modifications/alterations can be different in different strains or sequences due to the various sequences of the cleavage sites in the starting sequences. For example, 4 polybasic residues (RRKK) are typically removed in some HA sequences. (as compared to wt). In various embodiments, such polybasic cleavage sites can be modified in a number of ways (all of which are contained within the invention). For example, the polybasic cleavage site can be removed one amino acid at a time (e.g., one R removed, two Rs removed, RRK removed, or RRKK removed). Additionally, an amino acid residue directly upstream of the cleavage site can also be removed or altered (e.g., from an R to a T, etc.); also, the nucleotides encoding the amino acid residue directly after the cleavage site can also be modified. Those of skill in the art will be familiar with various methods of removing such specific regions. The resulting shortened sequences are also contained within the current invention. See, e.g., Li et al., J. of Infectious Diseases, 179:1132-8, 1999

The terms "temperature sensitive," "cold adapted" and "attenuated" as applied to viruses (typically used as vaccines or for vaccine production) which optionally encompass the current sequences, are well known in the art. For example, the term "temperature sensitive" (ts) indicates, e.g., that the virus exhibits a 100 fold or greater reduction in titer at 39° C. relative to 33° C. for influenza A strains, or that the virus exhibits a 100 fold or greater reduction in titer at 37° C. relative to 33° C. for influenza B strains. The term "cold adapted" (ca) indicates that the virus exhibits growth at 25° C. within 100 fold of its growth at 33° C., while the term "attenuated" (att) indicates that the virus replicates in the upper airways of ferrets but is not detectable in their lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), or exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses and can be used in conjunction with the HA and NA sequences herein.

Thus, the present invention can utilize growth, e.g., in appropriate culture conditions, of virus strains (both A strain and B strain influenza viruses) with desirable properties relative to vaccine production (e.g., attenuated pathogenicity or phenotype, cold adaptation, temperature sensitivity, etc.) in vitro in cultured cells. Influenza viruses can be produced by introducing a plurality of vectors incorporating cloned viral genome segments into host cells, and culturing the cells at a temperature not exceeding 35° C. When vectors including an influenza virus genome are transfected, recombinant viruses suitable as vaccines can be recovered by standard purification procedures. Using the vector system and methods of the invention, reassortant viruses incorporating the six internal gene segments of a strain selected for its desirable properties with respect to vaccine production, and the immunogenic HA and NA segments from a selected, e.g., pathogenic strain such as those in the sequence listing herein, can be rapidly and efficiently produced in tissue culture. Thus, the system and methods described herein are useful for the rapid production in cell culture of recombinant and reassortant influenza A and B viruses, including viruses suitable for use as vaccines, including live attenuated vaccines, such as vaccines suitable for intranasal administration.

In such embodiments, typically, a single Master Donor Virus (MDV) strain is selected for each of the A and B subtypes. In the case of a live attenuated vaccine, the Master Donor Virus strain is typically chosen for its favorable properties, e.g., temperature sensitivity, cold adaptation and/or attenuation, relative to vaccine production. For example, exemplary Master Donor Strains include such temperature sensitive, attenuated and cold adapted strains of A/Ann Arbor/6/60 and B/Ann Arbor/1/66, respectively, as well as others mentioned throughout.

For example, a selected master donor type A virus (MDV-A), or master donor type B virus (MDV-B), is produced from a plurality of cloned viral cDNAs constituting the viral genome. Embodiments include those wherein recombinant viruses are produced from eight cloned viral cDNAs. Eight viral cDNAs representing either the selected MDV-A or MDV-B sequences of PB2, PB1, PA, NP, HA, NA, M and NS are optionally cloned into a bi-directional expression vector, such as a plasmid (e.g., pAD3000), such that the viral genomic RNA can be transcribed from an RNA polymerase I (pol I) promoter from one strand and the viral mRNAs can be synthesized from an RNA polymerase II (pol II) promoter from the other strand. Optionally, any gene segment can be modified, including the HA segment (e.g., to remove the multi-basic cleavage site (also known as a polybasic cleavage site)).

Infectious recombinant MDV-A MDV-B virus can be then recovered following transfection of plasmids bearing the eight viral cDNAs into appropriate host cells, e.g., Vero cells, co-cultured MDCK/293T or MDCK/COS7 cells. Using the plasmids and methods described herein and, e.g., in U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"; Hoffmann, E., 2000, PNAS, 97(11):6108-6113; U.S. Published Patent Application No. 20020164770 to Hoffmann; and U.S. Pat. No. 6,544,785 issued Apr. 8, 2003 to Palese, et al., the invention is useful, e.g., for generating 6:2 reassortant influenza vaccines by co-transfection of the 6 internal genes (PB1 PB2, PA, NP, M and NS) of the selected virus (e.g., MDV-A, MDV-B) together with the HA and NA derived from different corresponding type (A or B) influenza viruses e.g., as shown in the sequence listings herein. For example, the HA segment is favorably selected from a pathogenically relevant H1, H3 or B strain, as is routinely performed for vaccine production. Similarly, the HA segment can be selected from a strain with emerging relevance as a pathogenic strain such as those in the sequence listing herein. Reassortants incorporating seven genome segments of the MDV and either the HA or NA gene of a selected strain (7:1 reassortants) can also be produced. It will be appreciated, and as is detailed throughout, the molecules of the invention can optionally be combined in any desired combination. For example, the HA and/or NA sequences herein can be placed, e.g., into a reassortant backbone such as A/AA/6/60, B/AA/1/66, A/Puerto Rico/8/34 (i.e., PR8), etc., in 6:2 reassortants or 7:1 reassortants, etc. Thus, as explained more fully below, there would be 6 internal genome segments from the donor virus (again, e.g., A/AA/6/60, etc.) and 2 genome segments from a second strain (e.g., a wild-type strain, not the donor virus). Such 2 genome segments are preferably the HA and NA genes. A similar situation arises for 7:1 reassortants, in which however, there are 7 genome segments from the donor virus and 1 genome segment (either HA or NA) from a different virus (typically wild-type or one to which an immune response is desired). Also, it will be appreciated that the sequences herein (e.g., those in the sequence listing of FIG. 1, etc.) can be combined in a number of means in different embodiments herein. Thus, any of the sequences herein can be present singularly in a 7:1 reassortant (i.e., the sequence of the invention present with 7 donor virus genome segments) and/or can be present with another sequence of the invention in a 6:2 reassortant. Within such 6:2 reassortants, any of the sequences of the invention can optionally be present with any other sequence of the invention. Typical, and preferred, embodiments comprise HA and NA from the same original wild-type strains however (or modified wild-type strains such as those with modified polybasic cleavage sites). For example, typical embodiments can comprise a 6:2 reassortant having 6 internal genome segments from a donor virus such as A/AA/6/60 and the HA and NA genuine segments described, herein. Of course, it will again be appreciated that the invention also includes such reassortant viruses wherein the HA and NA genome segments are from similar strains. The above references are specifically incorporated herein in their entirety for all purposes, e.g., especially for their teachings regarding plasmids, plasmid rescue of virus (influenza virus), multi-plasmid systems for virus rescue/production, etc.

Again, the HA and NA sequences of the current invention are optionally utilized in such plasmid reassortment vaccines (and/or in other ts, cs, ca, and/or att viruses and vaccines). However, it should be noted that the HA and NA sequences, etc. of the invention are not limited to specific vaccine compositions or production methods, and can, thus, be utilized in substantially any vaccine type or vaccine production method which utilizes strain specific HA and NA antigens (e.g., the sequences of the invention).

FLUMIST®

As mentioned previously, numerous examples and types of influenza vaccine exist. An exemplary influenza vaccine is FluMist (MedImmune Vaccines Inc., Mt. View, Calif.) which is a live, attenuated vaccine that protects children and adults from influenza illness (Belshe et al. (1998) *The efficacy of live attenuated, cold-adapted, trivalent, intranasal influenza virus vaccine in children* N Engl J Med 338:1405-12; Nichol et al. (1999) *Effectiveness of live, attenuated intranasal influenza virus vaccine in healthy, working adults: a randomized controlled trial* JAMA 282:137-44). In typical, and preferred, embodiments, the methods and compositions of the current invention are preferably adapted to/used with production of FluMist vaccine. However, it will be appreciated by those skilled in the art that the sequences, methods, compositions, etc. herein are also adaptable to production of similar or even different viral vaccines.

FluMist vaccine strains contain, e.g., HA and NA gene segments derived from the wild-type strains to which the vaccine is addressed (or, in some instances, to related strains) along with six gene segments, PB1, PB2, PA, NP, M and NS, from a common master donor virus (MDV). The HA and NA sequences herein, thus, are optionally part of various FluMist formulations. The MDV for influenza A strains of FluMist (MDV-A), was created by serial passage of the wild-type A/Ann Arbor/6/60 (A/AA/6/60) strain in primary chicken kidney tissue culture at successively lower temperatures (Maassab (1967) *Adaptation and growth characteristics of influenza virus at 25 degrees C.* Nature 213:612-4). MDV-A replicates efficiently at 25° C. (ca, cold adapted), but its growth is restricted at 38 and 39° C. (ts, temperature sensitive). Additionally, this virus does not replicate in the lungs of infected ferrets (alt, attenuation). The ts phenotype is believed to contribute to the attenuation of the vaccine in humans by restricting its replication in all but the coolest regions of the respiratory tract. The stability of this property has been demonstrated in animal models and clinical studies. In contrast to the is phenotype of influenza strains created by chemical mutagenesis, the ts property of MDV-A does not revert following passage through infected hamsters or in shed isolates from children (for a recent review, see Murphy & Coelingh (2002) *Principles underlying the development and use of live attenuated cold-adapted influenza A and B virus vaccines* Viral Immunol 15:295-323).

Clinical studies in over 20,000 adults and children involving 12 separate 6:2 reassortant strains have shown that these vaccines are attenuated, safe and efficacious (Belshe et al. (1998) *The efficacy of live attenuated, cold-adapted, trivalent, intranasal influenza virus vaccine in children* N Engl J Med 338:1405-12; Boyce et al. (2000) *Safety and immunogenicity of adjuvanted and unadjuvanted subunit influenza vaccines administered intranasally to healthy adults* Vaccine 19:217-26; Edwards et al. (1994) *A randomized controlled trial of cold adapted and inactivated vaccines for the prevention of influenza A disease* J Infect Dis 169:68-76; Nichol et al. (1999) *Effectiveness of live, attenuated intranasal influenza virus vaccine in healthy, working adults: a randomized controlled trial* JAMA 282:137-44). Reassortants carrying the six internal genes of MDV-A and the two HA and NA gene segments of a wild-type virus (i.e., a 6:2 reassortant) consistently maintain ca, ts and att phenotypes (Maassab et al. (1982) *Evaluation of a cold-recombinant influenza virus vaccine in ferrets* J. Infect. Dis. 146:780-900).

Production of such reassorted virus using B strains of influenza is more difficult, however, recent work (see, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus") has shown an eight plasmid system for the generation of influenza B virus entirely from cloned cDNA. Methods for the production of attenuated live influenza A and B virus suitable for vaccine formulations, such as live virus vaccine formulations useful for intranasal administration were also shown.

The system and methods described previously are useful for the rapid production in cell culture of recombinant and reassortant influenza A and B viruses, including viruses suitable for use as vaccines, including live attenuated vaccines, such as vaccines suitable for intranasal administration. The sequences, methods, etc. of the current invention, are optionally used in conjunction with, or in combination with, such previous work involving, e.g., reassorted influenza viruses for vaccine production to produce viruses for vaccines.

Methods and Compositions for Prophylactic Administration of Vaccines

As stated above, alternatively, or in addition to, use in production of FluMist™ vaccine, the current invention can be used in other vaccine formulations. In general, recombinant and reassortant viruses of the invention can be administered prophylactically in an immunologically effective amount and in an appropriate carrier or excipient to stimulate an immune response specific for one or more strains of influenza virus as determined by the HA and/or NA sequence. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol, allantoic fluid from uninfected hen eggs (i.e., normal allantoic fluid or NAF), or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

A related aspect of the invention provides methods for stimulating the immune system of an individual to produce a protective immune response against influenza virus. In the methods, an immunologically effective amount of a recombinant influenza virus (e.g., an HA and/or an NA molecule of the invention), an immunologically effective amount of a polypeptide of the invention, and/or an immunologically effective amount of a nucleic acid of the invention is administered to the individual in a physiologically acceptable carrier.

Generally, the influenza viruses of the invention are administered in a quantity sufficient to stimulate an immune response specific for one or more strains of influenza virus (i.e., against the HA and/or NA strains of the invention). Preferably, administration of the influenza viruses elicits a protective immune response to such strains. Dosages and methods for eliciting a protective immune response against one or more influenza strains are known to those of skill in the art. See, U.S. Pat. No. 5,922,326; Wright et al., Infect. Immun. 37:397-400 (1982); Kim et al., Pediatrics 52:56-63 (1973); and Wright et al., J. Pediatr. 88:931-936 (1976). For example, influenza viruses are provided in the range of about 1-1000 $HID_{50}$ (human infectious dose), i.e., about $10^5$-$10^8$ pfu (plaque forming units) per dose administered. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. See above. While stimulation of a protective immune response with a single dose is preferred, additional dosages can be administered, by the same or different route, to achieve the desired prophylactic effect.

Typically, the attenuated recombinant influenza of this invention as used in a vaccine is sufficiently attenuated such that symptoms of infection, or at least symptoms of serious infection, will not occur in most individuals immunized (or otherwise infected) with the attenuated influenza virus. In some instances, the attenuated influenza virus can still be capable of producing symptoms of mild illness (e.g., mild upper respiratory illness) and/or of dissemination to unvaccinated individuals. However, its virulence is sufficiently abrogated such that severe lower respiratory tract infections do not occur in the vaccinated or incidental host.

Alternatively, an immune response can be stimulated by ex vivo or in vivo targeting of dendritic cells with influenza viruses comprising the sequences herein. For example, proliferating dendritic cells are exposed to viruses in a sufficient amount and for a sufficient period of time to permit capture of the influenza antigens by the dendritic cells. The cells are then transferred into a subject to be vaccinated by standard intravenous transplantation methods.

While stimulation of a protective immune response with a single dose is preferred, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against wild-type influenza infection. Similarly, adults who are particularly susceptible to repeated or serious influenza infection, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Optionally, the formulation for prophylactic administration of the influenza viruses also contains one or more adjuvants for enhancing the immune response to the influenza antigens. Suitable adjuvants include: complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, bacille Calmette-Guerin (BCG), *Cornyebacterium parvum*, and the synthetic adjuvants QS-21 and MF59.

If desired, prophylactic vaccine administration of influenza viruses can be performed in conjunction with administration of one or more immunostimulatory molecules. Immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the influenza viruses, or can be administered separately. Either the protein (e.g., an HA and/or NA polypeptide of the invention) or an expression vector encoding the protein can be administered to produce an immunostimulatory effect.

The above described methods are useful for therapeutically and/or prophylactically treating a disease or disorder, typically influenza, by introducing a vector of the invention comprising a heterologous polynucleotide encoding a therapeutically or prophylactically effective HA and/or NA polypeptide (or peptide) or HA and/or NA RNA (e.g., an antisense RNA or ribozyme) into a population of target cells in vitro, ex vivo or in vivo. Typically, the polynucleotide encoding the polypeptide (or peptide), or RNA, of interest is operably linked to appropriate regulatory sequences, e.g., as described herein. Optionally, more than one heterologous coding sequence is incorporated into a single vector or virus. For example, in addition to a polynucleotide encoding a therapeutically or prophylactically active HA and/or NA polypeptide or RNA, the vector can also include additional therapeutic or prophylactic polypeptides, e.g., antigens, co-stimulatory molecules, cytokines, antibodies, etc., and/or markers, and the like.

Although vaccination of an individual with an attenuated influenza virus of a particular strain of a particular subgroup can induce cross-protection against influenza virus of different strains and/or subgroups, cross-protection can be enhanced, if desired, by vaccinating the individual with attenuated influenza virus from at least two, at least three, or at least four influenza virus strains or substrains, e.g., at least two of which may represent a different subgroup. For example, vaccinating an individual with at least four strains or substrains of attenuated influenza virus may include vaccinating the individual with at least two strains or substrains of influenza A virus and at least two strains or substrains of influenza B virus. Vaccinating the individual with the at least four strains or substrains of attenuated influenza virus may include vaccinating the individual with at least three strains or substrains of influenza A virus and at least one strain or substrain of influenza B virus. The vaccination of the individual with at least four influenza virus strains or substrains may require administration of a single tetravalent vaccine which comprises all of the at least four attenuated influenza virus strains or substrains. The vaccination may alternatively require administration of multiple vaccines, each of which comprises one, two, or three of the attenuated influenza virus strains or substrains. Additionally, vaccine combinations can optionally include mixes of pandemic vaccines and non-pandemic strains. Vaccine mixtures (or multiple vaccinations) can comprise components from human strains and/or non-human influenza strains (e.g., avian and human, etc.). Similarly, the attenuated influenza virus vaccines of this invention can optionally be combined with vaccines that induce protective immune responses against other infectious agents. In one embodiment, a vaccine of the invention is a trivalent vaccine comprising three reassortant influenza viruses. In one embodiment, a vaccine of the invention is a trivalent vaccine comprising two reassortant influenza A viruses and a reassortant influenza B virus. In one embodiment, a vaccine of the invention is a trivalent vaccine comprising a reassortant influenza A virus of the H1 type, a reassortant influenza A virus of the H3 type and a reassortant influenza B virus. In another embodiment, a vaccine of the invention is a tetravalent vaccine comprising four reassortant influenza viruses. In one embodiment, a vaccine of the invention is a tetravalent vaccine comprising two reassortant influenza A viruses and two reassortant influenza B viruses. In one embodiment, a vaccine of the invention is a tetravalent vaccine comprising a reassortant influenza A virus of the type, a reassortant influenza A virus of the H3 type, a reassortant influenza B virus of the Victoria lineage and a reassortant influenza B virus of the Yamagata lineage.

Production of Recombinant Virus

Negative strand RNA viruses can be genetically engineered and recovered using a recombinant reverse genetics approach (U.S. Pat. No. 5,166,057 to Palese et al.). Such method was originally applied to engineer influenza viral genomes (Luytjes et al. (1989) Cell 59:1107-1113; Enami et al. (1990) Proc. Natl. Acad. Sci. USA 92:11563-11567), and has been successfully applied to a wide variety of segmented and nonsegmented negative strand RNA viruses, e.g., rabies (Schnell et al. (1994) EMBO J. 13: 4195-4203); VSV (Lawson et al. (1995) Proc. Natl. Acad. Sci. USA 92: 4477-4481); measles virus (Radecke et al. (1995) EMBO J. 14:5773-5784); rinderpest virus (Baron & Barrett (1997) J. Virol. 71: 1265-1271); human parainfluenza virus (Hoffman & Banerjee (1997) J. Virol. 71; 3272-3277; Dubin et al. (1997) Virology 235:323-332); SV5 (He et al. (1997) Virology 237:249-260); canine distemper virus (Gassen et al. (2000) J. Virol. 74:10737-44); and Sendai virus (Park et al. (1991) Proc. Natl. Acad. Sci. USA 88: 5537-5541; Kato et al. (1996) Genes to Cells 1:569-579). Those of skill in the art will be familiar with these and similar techniques to produce influenza virus comprising the HA and NA sequences of the invention. Recombinant influenza viruses produced according to such methods are also a feature of the invention, as are recombinant influenza virus comprising one or more nucleic acids and/or polypeptides of the invention. Of course, as will be appreciated by those of skill in the art, influenza viruses in general (and those of the invention as well) are negative stranded RNA viruses. Thus, when the present invention describes influenza viruses as comprising, e.g., the sequences of FIG. 1, etc., it is to be understood to typically mean the corresponding negative stranded RNA version of the sequences. The nucleotide sequences in FIG. 1 comprise DNA versions (e.g., coding plus sense, etc.) of the genes (along with some untranslated regions in the nucleotide sequences). Those of skill in the art can easily convert between RNA and DNA sequences (e.g., changing U to T, etc.), and between complementary nucleotide sequences (whether RNA or DNA), etc. Thus, for example, those of skill in the art can easily convert from a nucleotide sequence to the corresponding amino acid sequence or to a corresponding complementary sequence (whether DNA or RNA), etc. Also, as will be evident, when such HA and/or NA sequences are described within DNA vectors, e.g., plasmids, etc., then the corresponding DNA version of the sequences are typically to be understood. Again, nucleic acids of the invention include the explicit sequences in the sequence listings herein, as well as the complements of such sequences (both RNA and DNA), the double stranded form of the sequences in the sequence listings, the corresponding RNA forms of the sequences in the sequence listings (either as the RNA complement to the explicit sequence in the sequence listing or as the RNA version of the sequence in the sequence listing, e.g., of the same sense, but comprised of RNA, with U place of T, etc).

Cell Culture and Expression Hosts

The present invention also relates to host cells that are introduced (transduced, transformed or transfected) with vectors of the invention, and the production of polypeptides of the invention by recombinant techniques. Host cells are genetically engineered (i.e., transduced, transformed or transfected) with a vector, such as an expression vector, of this invention. As described above, the vector can be in the form of a plasmid, a viral particle, a phage, etc. Examples of appropriate expression hosts include: bacterial cells, such as E. coli,

*Streptomyces*, and *Salmonella typhimurium*; fungal cells, such as *Saccharomyces cerevisiae, Pichia pastoris*, and *Neurospora crassa*; or insect cells such as *Drosophila* and *Spodoptera frugiperda*.

Most commonly, mammalian cells are used to culture the HA and NA molecules of the invention. Suitable host cells for the replication of influenza virus (e.g., with the HA and/or NA sequences herein) include, e.g., Vero cells, BHK cells, MDCK cells, 293 cells and COS cells, including 293T cells, COS7 cells or the like. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

The engineered host cells can be cultured in conventional nutrient media modified as appropriate for activating promoters, selecting transformants, or amplifying the inserted polynucleotide sequences, e.g., through production of viruses. The culture conditions, such as temperature, pH and the like, are typically those previously used with the particular host cell selected for expression, and will be apparent to those skilled in the art and in the references cited herein, including, e.g., Freshney (1994) Culture of Animal Cells, a Manual of Basic Technique, 3$^{rd}$ edition, Wiley-Liss, New York and the references cited therein. Other helpful references include, e.g., Paul (1975) Cell and Tissue Culture, 5$^{th}$ ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) *Production of influenza virus in cell cultures for vaccine preparation*. in Cohen and Shafferman (eds.) Novel Strategies in Design and Production of Vaccines, which is incorporated herein in its entirety for all purposes. Additionally, variations in such procedures adapted to the present invention are readily determined through routine experimentation and will be familiar to those skilled in the art.

Cells for production of influenza virus (e.g., having the HA and/or NA sequences of the invention) can be cultured in serum-containing or serum free medium. In some cases, e.g., for the preparation of purified viruses, it is typically desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech international (B. Braun Biotech, Melsungen, Germany).

Regardless of the culture volume, in many desired aspects of the current invention, it is important that the cultures be maintained at an appropriate temperature, to insure efficient recovery of recombinant and/or reassortant influenza virus using temperature dependent plasmid systems (see, e.g., U.S. Application No. 60/420,708, filed Oct. 23, 2002, U.S. application Ser. No. 10/423,828, filed Apr. 25, 2003, and U.S. Application No. 60/574,117, filed May 24, 2004, all entitled "Multi-Plasmid System for the Production of Influenza Virus"), heating of virus solutions for filtration, etc. Typically, a regulator, e.g., a thermostat, or other device for sensing and maintaining the temperature of the cell culture system and/or other solution, is employed to insure that the temperature is at the correct level during the appropriate period (e.g., virus replication, etc.).

In some embodiments herein (e.g., wherein reassorted viruses are to be produced from segments on vectors) vectors comprising influenza genome segments are introduced (e.g., transfected) into host cells according to methods well known in the art for introducing heterologous nucleic acids into eukaryotic cells, including, e.g., calcium phosphate co-precipitation, electroporation, microinjection, lipofection, and transfection employing polyamine transfection reagents. For example, vectors, e.g., plasmids, can be transfected into host cells, such as COS cells, 293T cells or combinations of COS or 293T cells and MDCK cells, using the polyamine transfection reagent TransIT-LT1 (Mirus) according to the manufacturer's instructions in order to produce reassorted viruses, etc. Thus, in one example, approximately 1 μg of each vector is introduced into a population of host cells with approximately 2 μl of TransIT-LT1 diluted in 160 μl medium, preferably serum-free medium, in a total volume of 200 μl. The DNA:transfection reagent mixtures are incubated at room temperature for 45 minutes followed by addition of 800 μl of medium. The transfection mixture is added to the host cells, and the cells are cultured as described via other methods well known to those skilled in the art. Accordingly, for the production of recombinant or reassortant viruses in cell culture, vectors incorporating each of the 8 genome segments, (PB2, PB1, PA, NP, M, NS, HA and NA, of the invention) are mixed with approximately 20 μl TransIT-LT1 and transfected into host cells. Optionally, serum-containing medium is replaced prior to transfection with serum-free medium, e.g., Opti-MEM I, and incubated for 4-6 hours.

Alternatively, electroporation can be employed to introduce such vectors incorporating influenza gnome segments into host cells. For example, plasmid vectors incorporating an influenza A or influenza B virus are favorably introduced into Vero cells using electroporation according to the following procedure. In brief, approximately $5 \times 10^6$ Vero cells, e.g., grown in Modified Eagle's Medium (MEM) supplemented with 10% Fetal Bovine Serum (FBS) are resuspended in 0.4 ml OptiMEM and placed in an electroporation cuvette. Twenty micrograms of DNA in a volume of up to 25 μl is added to the cells in the cuvette, which is then mixed gently by tapping. Electroporation is performed according to the manufacturer's instructions BioRad Gene Pulser II with Capacitance Extender Plus connected) at 300 volts, 950 microFarads with a time constant of between 28-33 msec. The cells are remixed by gently tapping and approximately 1-2 minutes following electroporation 0.7 ml MEM with 10% FBS is added directly to the cuvette. The cells are then transferred to two wells of a standard 6 well tissue culture dish containing 2 ml MEM, 10% FBS. The cuvette is washed to recover any remaining cells and the wash suspension is divided between the two wells. Final volume is approximately 3.5 mL. The cells are then incubated under conditions permissive for viral growth, e.g., at approximately 33° C. for cold adapted strains.

In mammalian host cells, a number of expression systems, such as viral-based systems, can be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing the polypeptides of interest in infected host cells (Logan and Shenk (1984) Proc Natl Acad Sci 81:3655-3659). In addition, transcription enhancers, such as the rous sarcoma virus (RSV) enhancer, can be used to increase expression in mammalian host cells.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing, which cleaves a precursor form into a mature form, of the protein is sometimes important for correct insertion, folding and/or function. Additionally proper location within a host cell (e.g., on the cell surface) is also important. Different host cells such as COS, CHO, BHK, MDCK, 293, 293T, COS7, etc. have specific cellular machinery and characteristic mechanisms for such post-translational activities and can be chosen to ensure the correct modification and processing of the current introduced, foreign protein.

For long-term, high-yield production of recombinant proteins encoded by, or having subsequences encoded by, the polynucleotides of the invention, stable expression systems are optionally used. For example, cell lines, stably expressing a polypeptide of the invention, are transfected using expression vectors that contain viral origins of replication or endogenous expression elements and a selectable marker gene. For example, following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Thus, resistant clumps of stably transformed cells, e.g., derived from single cell type, can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The cells expressing said protein can be sorted, isolated and/or purified. The protein or fragment thereof produced by a recombinant cell can be secreted, membrane-bound, or retained intracellularly, depending on the sequence (e.g., depending upon fusion proteins encoding a membrane retention signal or the like) and/or the vector used.

Expression products corresponding to the nucleic acids of the invention can also be produced in non-animal cells such as plants, yeast, fungi, bacteria and the like. In addition to Sambrook, Berger and Ausubel, all infra, details regarding cell culture can be found in Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Atlas and Parks (eds.) The Handbook of Microbiological Media (1993) CRC Press, Boca Raton, Fla.

In bacterial systems, a number of expression vectors can be selected depending upon the use intended for the expressed product. For example, when large quantities of a polypeptide or fragments thereof are needed for the production of antibodies, vectors that direct high-level expression of fusion proteins that are readily purified are favorably employed. Such vectors include, but are not limited to, multifunctional *E. coli* cloning and expression vectors such as BLUESCRIPT (Stratagene), in which the coding sequence of interest, sequences comprising those found herein, etc., can be ligated into the vector in-frame with sequences for the amino-terminal translation initiating methionine and the subsequent 7 residues of beta-galactosidase producing a catalytically active beta galactosidase fusion protein; pIN vectors (Van Heeke & Schuster (1989) J Biol Chem 264:5503-5509); pET vectors (Novagen, Madison Wis.); and the like. Similarly, in the yeast *Saccharomyces cerevisiae* a number of vectors containing constitutive or inducible promoters such as alpha factor, alcohol oxidase and PGH can be used for production of the desired expression products. For reviews, see Ausubel, infra, and Grant et al., (1987); Methods in Enzymology 153: 516-544.

Cloning, Mutagenesis and Expression of Biomolecules of Interest

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 2002) ("Ausubel")). These texts describe mutagenesis, the use of vectors, promoters and many other relevant topics related, to, e.g., the generation of HA and/or NA molecules, etc.

Various types of mutagenesis are optionally used in the present invention, e.g., to produce and/or isolate, e.g., novel or newly isolated HA and/or NA molecules and/or to further modify/mutate the polypeptides (e.g., HA and NA molecules) of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures as well as the following publications (and references cited within): Sieber, et al., Nature Biotechnology, 19:456-460 (2001); Ling et al., *Approaches to DNA mutagen-* esis: an overview, Anal Bioehem 254(2): 157-178 (1997); Dale et al., Oligonucleotide-directed random mutagenesis using the phosphorothioate method, Methods Mol Biol 57:369-374 (1996); I. A. Lorimer, I. Pastan, Nucleic Acids Res 23, 3067-8 (1995); W. P. C. Stemmer, Nature 370, 389-91 (1994); Arnold, Protein engineering for unusual environments, Current Opinion in Biotechnology 4:450-455 (1993); Bass et al., Mutant Trp repressors with new DNA-binding specificities, Science 242:240-245 (1988); Fritz et al., Oligonucleotide-directed construction of mutations: a gapped duplex DNA procedure without enzymatic reactions in vitro, Nucl Acids Res 16: 6987-6999 (1988); Kramer et al., Improved enzymatic in vitro reactions in the gapped duplex DNA approach to oligonucleotide-directed construction of mutations, Nucl Acids Res 16: 7207 (1988); Sakamar and Khorana, Total synthesis and expression of a gene for the α-subunit of bovine rod outer segment guanine nucleotide-binding protein (transducin), Nucl Acids Res 14: 6361-6372 (1988); Sayers et al., Y-T Exonucleases phosphorothioate-based oligonucleotide-directed mutagenesis, Nucl Acids Res 16:791-802 (1988); Sayers et al., Strand specific cleavage of phosphorothioate-containing DNA by reaction with restriction endonucleases the presence of ethidium bromide, (1988) Nucl Acids Res 16: 803-814; Carter, Improved oligonucleotide-directed mutagenesis using M13 vectors, Methods in Enzymol 154: 382-403 (1987); Kramer & Fritz Oligonucleotide-directed construction of mutations via gapped duplex DNA, Methods in Enzymol 154:350-367 (1987); Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel et al., Rapid and efficient site-specific mutagenesis without phenotypic selection, Methods in Enzymol 154, 367-382 (1987); Zoller & Smith, Oligonucleotide-directed mutagenesis: a simple method using two oligonucleotide primers and a single-stranded DNA template, Methods in Enzymol 154: 329-350 (1987); Carter, Site-directed mutagenesis, Biochem J 237:1-7 (1986); Eghtedarzadeh & Henikoff, Use of oligonucleotides to generate large deletions, Nucl Acids Res 14: 5115 (1986); Mandecki, Oligonucleotide-directed double-strand break repair in plasmids of Escherichia coli: a method for site-specific mutagenesis, Proc Natl Acad Sci USA, 83:7177-7181 (1986); Nakamaye & Eckstein, Inhibition of restriction endonuclease Nci I cleavage by phosphorothioate groups and its application to oligonucleotide-directed mutagenesis, Nucl Acids Res 14; 9679-9698 (1986); Wells et al., Importance of hydrogen-bond formation in stabilizing the transition state of subtilisin, Phil Trans R Soc Lond A 317: 415-423 (1986); Botstein & Shortle, Strategies and applications of in vitro mutagenesis, Science 229:1193-1201 (1985); Carter et al., Improved oligonucleotide site-directed mutagenesis using M13 vectors, Nucl Acids Res 13: 4431-4443 (1985); Grundström et al., Oligonucleotide-directed mutagenesis by microscale 'shot-gun' gene synthesis, Nucl Acids Res 13: 3305-3316 (1985); Kunkel, Rapid and efficient site-specific mutagenesis without phenotypic selection, Proc Natl Acad Sci USA 82:488-492 (1985); Smith, In vitro mutagenesis, Ann Rev Genet 19:423-462 (1985); Taylor et al., The use of phosphorothioate-modified DNA in restriction enzyme reactions to prepare nicked DNA, Nucl Acids Res 13: 8749-8764 (1985); Taylor et al., The rapid generation of oligonucleotide-directed mutations at high frequency using phosphorothioate-modified DNA, Nucl Acids Res 13: 8765-8787 (1985); Wells et al., Cassette mutagenesis: efficient method for generation of multiple mutations at defined sites, Gene 34:315-323 (1985); Kramer et al., The gapped duplex DNA approach to oligonucleotide-directed mutation construction, Nucl Acids Res 12: 9441-9456 (1984); Kramer et al., Point Mismatch Repair, Cell 38:879-887 (1984); Nambiar et al., Total synthesis and cloning of a gene coding for the ribonuclease S protein, Science 223: 1299-1301 (1984); Zoller & Smith, Oligonucleotide-directed mutagenesis of DNA fragments cloned into M13 vectors, Methods in Enzymol 100:468-500 (1983); and Zoller & Smith, Oligonucleotide-directed mutagenesis using M13-derived vectors: an Efficient and general procedure for the production of point mutations in any DNA fragment, Nucl Acids Res 10:6487-6500 (1982). Additional details on many of the above methods can be found in Methods in Enzymol Volume 154, which also describes useful controls for trouble-shooting problems with various mutagenesis, gene isolation, expression, and other methods.

Oligonucleotides, e.g., for use in mutagenesis of the present invention, e.g., mutating libraries of the HA and/or NA molecules of the invention, or altering such, are typically synthesized chemically according to the solid phase phosphoramidite triester method described by Beaucage and Caruthers, Tetrahedron Letts 22(20):1859-1862, (1981) e.g., using an automated synthesizer, as described in Needham-VanDevanter et al., Nucleic Acids Res, 12:6159-6168 (1984).

In addition, essentially any nucleic acid can be custom or standard ordered from any of a variety of commercial sources Similarly, peptides and antibodies can be custom ordered from any of a variety of sources.

The present invention also relates to host cells and organisms comprising a HA and/or NA molecule or other polypeptide and/or nucleic acid of the invention or such HA and/or NA or other sequences within various vectors such as 6:2 reassortant influenza viruses, plasmids in plasmid rescue systems, etc. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (see, From et al., Proc Natl Acad Sci USA 82, 5824 (1985), infection by viral vectors, high velocity ballistic penetration by small particles with the nucleic acid either within the matrix of small beads or particles, or on the surface (Klein et al., Nature 327, 70-73 (1987)). Berger, Sambrook, and Ausubel provide a variety of appropriate transformation methods. See, above.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors, etc. Bacterial cells can be used to amplify the number of plasmids containing DNA constructs of this invention. The bacteria are grown to log phase and the plasmids within the bacteria can be isolated by a variety of methods known M the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Gillman & Smith, Gene 8:81 (1979); Roberts, et al., Nature, 328:731 (1987); Schneider, B., et al., Protein Expr Purif 6435:10 (1995); Ausubel, Sambrook, Berger (all supra), A catalogue of Bacteria and Bacteriophages useful for cloning is provided, by the ATCC, e.g., The ATCC Catalogue of Bacteria and Bacteriophage (1992) Gherna et al. (eds.) published by the ATCC. Additional basic procedures for sequencing, cloning and other aspects of molecular biology and underlying theoretical considerations are also found in Watson et al. (1992) Recombinant DNA Second Edition Scientific American Books, NY. See, above, Polypeptide Production and Recovery In some embodiments, following transduction of a suitable host cell line or strain and growth of the host cells to an appropriate cell density, a selected promoter is induced by appropriate means temperature shift or chemical induction) and cells are cultured for an additional period. In some embodiments, a secreted polypeptide product, e.g., a HA and/or NA polypeptide in a secreted fusion protein form, etc., is then recovered from the culture medium, other embodiments, a virus particle containing one or more HA and/or NA polypeptide of the invention is produced from the cell. Alternatively, cells can be harvested by centrifugation, disrupted by physical or chemical means, and the resulting crude extract retained for further purification. Eukaryotic or microbial cells employed in expression of proteins can be disrupted by any convenient method, including freeze-thaw cycling, sonication, mechanical disruption, or use of cell lysing agents, or other methods, which are well know to those skilled in the art. Additionally, cells expressing a HA and/or a NA polypeptide product of the invention can be utilized without separating the polypeptide from the cell. In such situations, the polypeptide of the invention is optionally expressed on the cell surface and is examined thus by having HA and/or NA molecules, or fragments thereof, e.g., comprising fusion proteins or the like) on the cell surface bind antibodies, etc. Such cells are also features of the invention.

Expressed polypeptides can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems known to those skilled in the art), hydroxylapatite chromatography, and lectin chromatography. Protein refolding steps can be used, as desired, in completing configuration of the mature protein. Also, high performance liquid chromatography (HPLC) can be employed in the final purification steps. In addition to the references noted herein, a variety of purification methods are well known in the art, including, e.g., those set forth in Sandana (1997) Bioseparation of Proteins, Academic Press, Inc.; and Bollag et al. (1996) Protein Methods, $2^{nd}$ Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice $3^{rd}$ Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ.

When the expressed polypeptides of the invention are produced in viruses, the viruses are typically recovered from the culture medium, in which infected (transfected) cells have been grown. Typically, crude medium is clarified prior to concentration of influenza viruses. Common methods include ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01M Tris-HCl; 0.15 M NaCl; 0.0001M EDTA) or phosphate buffered saline (PBS) at pH 7.4, the virus is concentrated by density gradient centrifugation on sucrose (60%-42%) or potassium tartrate (50%-40%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and thr most large-scale commercial applications, virus is elutriated from density gradients using a zonal-centrifuge rotor operating in continuous mode. Additional details sufficient to guide one of skill through the preparation of influenza viruses from tissue culture are provided, e.g., in Furminger, *Vaccine Production*, in Nicholson et al. (eds.) Textbook of Influenza pp. 324-332; Merten et al. (1996) *Production of influenza virus in cell cultures for vaccine preparation*, in Cohen & Shafferman (eds.) Novel Strategies in Design and Production of Vaccines pp. 141-151, and U.S. Pat. No. 5,690,937. If desired, the recovered viruses can be stored at −80° C. in the presence of sucrose-phosphate-glutamate (SPG) as a stabilizer Modified Amino Acids Expressed polypeptides of the invention can contain one or more modified amino acids. The presence of modified amino acids can be advantageous in, for example, (a) increasing polypeptide serum half-life, (b) reducing/increasing polypeptide antigenicity, (c) increasing polypeptide storage stability, etc. Amino acid(s) are modified, for example, co-translationally or post-translationally during recombinant production (e.g., N-linked glycosylation N—X—S/T motifs during expression in mammalian cells) or modified by synthetic means (e.g., via PEGylation).

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like, as well as amino acids modified by conjugation to, e.g., lipid moieties or other organic derivatizing agents. References adequate to guide one of skill in the modification of amino acids are replete throughout the literature. Example protocols are found in Walker (1998) Protein Protocols on CD-ROM Human Press, Towata, N.J.

Fusion Proteins

The present invention also provides fusion proteins comprising fusions of the sequences of the invention (e.g., encoding HA and/or NA polypeptides) or fragments thereof with, e.g., immunoglobulins (or portions thereof), sequences encoding, e.g., GFP (green fluorescent protein), or other similar markers, etc. Nucleotide sequences encoding such fusion proteins are another aspect of the invention. Fusion proteins of the invention are optionally used for, similar applications (including, e.g., therapeutic, prophylactic, diagnostic, experimental, etc. applications as described herein) as the non-fusion proteins of the invention. In addition to fusion with immunoglobulin sequences and marker sequences, the proteins of the invention are also optionally fused with, e.g., sequences which allow sorting of the fusion proteins and/or targeting of the fusion proteins to specific cell types, regions, etc.

Antibodies

The polypeptides of the invention can be used to produce antibodies specific for the polypeptides given herein and/or polypeptides encoded by the polynucleotides of the invention, e.g., those shown herein, and conservative variants thereof. Antibodies specific for the above mentioned polypeptides are useful, e.g., for diagnostic and therapeutic purposes, e.g., related to the activity, distribution, and expression of tartlet polypeptides. For example, such antibodies can optionally be utilized to define other viruses within the same strain(s) as the HA/NA sequences herein.

Antibodies specific for the polypeptides of the invention can be generated by methods well known in the art. Such antibodies can include, but are not limited to, polyclonal, monoclonal, chimeric, humanized, single chain, Fab fragments and fragments produced by an Fab expression library.

Polypeptides do not require biological activity for antibody production (e.g., full length functional hemagglutinin or neuraminidase is not required). However, the polypeptide or oligopeptide must be antigenic. Peptides used to induce specific antibodies typically have an amino acid sequence of at least about 4 amino acids, and often at least 5 or 10 amino acids. Short stretches of a polypeptide can be fused with another protein, such as keyhole limpet hemocyanin, and antibody produced against the chimeric molecule.

Numerous methods for producing polyclonal and monoclonal antibodies are known to those of skill in the art, and can be adapted to produce antibodies specific for the polypeptides of the invention, and/or encoded by the polynucleotide sequences of the invention, etc. See, e.g., Coligan (1991) Current Protocols in Immunology Wiley/Greene, N.Y.; Paul (ed.) (1998) Fundamental Immunology, Fourth Edition, Lippincott-Raven, Lippincott Williams & Wilkins; Harlow and Lane (1989) Antibodies: A Laboratory Manual Cold Spring Harbor Press, NY; Stites et al. (eds.) Basic and Clinical Immunology (4th ed.) Lange Medical Publications; Los Altos, Calif.; and references cited therein; Goding (1986) Monoclonal Antibodies: Principles and Practice (2d ed.) Academic Press, New York, N.Y.; and Kohler and Milstein (1975) Nature 256: 495-497. Other suitable techniques for antibody preparation include selection of libraries of recombinant antibodies in phage or similar vectors. See, Huse et al. (1989) Science 246: 1275-1281; and Ward, et al. (1989) Nature 341: 544-546. Specific monoclonal and polyclonal antibodies and antisera will usually bind with a $K_D$ of, e.g., at least about 0.1 µM, at least about 0.01 µM or better, and, typically and at least about 0.001 µM or better.

For certain therapeutic applications, humanized antibodies are desirable. Detailed methods for preparation of chimeric (humanized) antibodies can be found in U.S. Pat. No. 5,482,856. Additional details on humanization and other antibody production and engineering techniques can be found in Borrehaeck (ed.) (1995) Antibody Engineering, 2$^{nd}$ Edition Freeman and Company, NY (Borrebaeck); McCafferty et al. (1996) Antibody Engineering, A Practical Approach IRL at Oxford Press, Oxford, England (McCafferty), and Paul (1995) Antibody Engineering Protocols Humana Press. Towata, N.J. (Paul). Additional details regarding specific procedures can be found, e.g., in Ostberg et al. (1983), Hybridoma 2: 361-367, Ostberg, U.S. Pat. No. 4,634,664; and Engelman et al., U.S. Pat. No. 4,634,666.

Nucleic Acid and Polypeptide Sequence Variants

As described herein, the invention provides for nucleic acid polynucleotide sequences and polypeptide amino acid sequences, e.g., hemagglutinin and neuraminidase sequences, and, e.g., compositions and methods comprising said sequences. Examples of said sequences are disclosed herein. However, one of skill in the art will appreciate that the invention is not necessarily limited to those sequences disclosed herein and that the present invention also provides many related and unrelated sequences with the functions described herein, e.g., encoding a HA and/or a NA molecule.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Silent Variations

Due to the degeneracy of the genetic code, any of a variety of nucleic acid sequences encoding polypeptides and/or viruses of the invention are optionally produced, some which can bear lower levels of sequence identity to the HA and NA nucleic acid and polypeptide sequences herein. The following provides a typical codon table specifying the genetic code, found in many biology and biochemistry texts.

TABLE 1

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |

TABLE 1-continued

Codon Table

| Amino acids | | | Codon |
|---|---|---|---|
| Valine | Val | V | GUA GUC GUG GUU |
| Tryptophan | Trp | W | UGG |
| Tyrosine | Tyr | Y | UAC UAU |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations," discussed below. One of skill will recognize that each codon in a nucleic acid (except ATG, which is ordinarily the only codon for methionine, and TTG, which is ordinarily the only codon for tryptophan) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a hemagglutinin or a neuraminidase polypeptide of the invention. All such variations of every nucleic acid herein are specifically provided and described by consideration of the sequence in combination with the genetic code. One of skill is fully able to make these silent substitutions using the methods herein.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence of the invention which encodes an amino acid. Similarly, "conservative amino acid substitutions," in one or a few amino acids in an amino acid sequence are substituted with different amino acids with highly similar properties, are also readily identified as being highly similar to a disclosed construct such as those herein. Such conservative variations of each disclosed sequence are a feature of the present invention.

"Conservative variation" of a particular nucleic acid sequence refers to those nucleic acids which encode identical or essentially identical amino acid sequences, or, where the nucleic acid does not encode an amino acid sequence, to essentially identical sequences, see, Table 2 below. One of skill will recognize that individual substitutions, deletions or additions which alter, add or delete a single amino acid or a small percentage of amino acids (typically less than 5%, more typically less than 4%, 3%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 4%, 3%, 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

TABLE 2

| Conservative Substitution Groups | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs and/or RNAs encoding a HA or NA molecule, or the amino acid sequence of a HA or NA molecule) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, "substantial identity" exists over a region of the amino acid sequences that is at least about 200 residues in length, more preferably over a region of at least about 250 residues, and most preferably the sequences are substantially identical over at least about 300 residues, 350 residues, 400 residues, 425 residues, 450 residues, 475 residues, 480 residues, 490 residues, 495 residues, 499 residues, 500 residues, 502 residues, 559 residues, 565 residues, or 566 residues, or over the full length of the two sequences to be compared when the amino acids are hemagglutinin or hemagglutinin fragments or which is substantially identical over at least about 350 amino acids; over at least about 400 amino acids; over at least about over at least about 436 amino acids, over at least about 450 amino acids; over at least about 451 amino acids; over at least about 465 amino acids; over at least about 466 amino acids; over at least about 469 amino acids; over at least about 470 amino acids; or over at least about 566 amino acids contiguous when the amino acid is neuraminidase or a neuraminidase fragment.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv Appl Math 2:482 (1981), by the homology alignment algorithm of Needleman & Wunsch, J Mol Biol 48:443 (1970), by the search for similarity method of Pearson & Lipman, Proc Natl Acad Sci USA 85:2444 (1988), by computerized implementations of algorithms such as GAP, BESTFIT, FASTA, and TFASTA in the Wisconsin Genetics Software Package, Genetics Computer Group, 575 Science Dr., Madison, Wis., or by visual inspection (see generally, Ausubel et al., supra).

One example of an algorithm that is suitable for determining percent sequence identity and sequence similarity is the BLAST algorithm, which is described in Altschul et al., J Mol Biol 215:403-410 (1990). Software for performing BLAST analyses is publicly available through the web page of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (see, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) Proc Natl Acad Sci USA 89:10915).

In addition to calculating percent sequence identity, the BLAST algorithm also performs a statistical analysis of the similarity between two sequences (see, e.g., Karlin & Altschul, Proc Natl Acad Sci USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) CABIOS 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple nucleic acid, or amino acid, sequence alignments is the CLUSTALW program (Thompson, J. D. et al. (1994) Nucl. Acids. Res. 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) Proc. Natl. Acad. Sci. USA 89: 10915-10919.

Digital Systems

The present invention provides digital systems, e.g., computers, computer readable media and integrated systems comprising character strings corresponding to the sequence information herein for the nucleic acids and isolated or recombinant polypeptides herein, including, e.g., the sequences shown herein, and the various silent substitutions and conservative substitutions thereof. Integrated systems can further include, e.g., gene synthesis equipment for making genes corresponding to the character strings.

Various methods known in the art can be used to detect homology or similarity between different character strings, or can be used to perform other desirable functions such as to control output files, provide the basis for making presentations of information including the sequences and the like. Examples include BLAST, discussed supra. Computer systems of the invention can include such programs, e.g., in conjunction with one or more data file or data base comprising a sequence as noted herein.

Thus, different types of homology and similarity of various stringency and length between various HA or NA sequences or fragments, etc. can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among four principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.).

Thus, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™, Paradox™, GeneWorks™, or MacVector™ or other similar programs) can be adapted to the present invention by inputting a character string corresponding to one or more polynucleotides and polypeptides of the invention (either nucleic acids or proteins, or both). For example, a system of the invention can include the foregoing software having the appropriate character string information, e.g., used in conjunction with a user interface (e.g., a GUI in a standard operating system such as a Windows, Macintosh or LINUX system) to manipulate strings of characters corresponding to the sequences herein. As noted, specialized alignment programs such as BLAST can also be incorporated into the systems of the invention for alignment of nucleic acids or proteins (or corresponding character strings).

Systems in the present invention typically include a digital computer with data sets entered into the software system comprising any of the sequences herein. The computer can be, e.g., a PC (Intel x86 or Pentium chip-compatible DOS™, OS2™ WINDOWS™ WINDOWSNT™, WINDOWS95™, WINDOWS2000™, WINDOWS98™, LINUX based machine, a MACINTOSH™, Power PC, or a UNIX based (e.g., SUN™ work station) machine) or other commercially available computer that is known to one of skill. Software for aligning or otherwise manipulating sequences is available, or can easily be constructed by one of skill using a standard programming language such as Visualbasic, PERL, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation, e.g., of appropriate mechanisms or transport controllers to carry out the desired operation. The software can also include output elements for controlling nucleic acid synthesis (e.g., based upon a sequence or an alignment of sequences herein), comparisons of samples for differential acne expression, or other operations, Kits and Reagents The present invention is optionally provided to a user as a kit. For example, a kit of the invention contains one or more nucleic acid, polypeptide, antibody, or cell line described herein (e.g., comprising, or with, a HA and/or NA molecule of the invention). The kit can contain a diagnostic nucleic acid or polypeptide, e.g., antibody, probe set, e.g., as a cDNA microarray packaged in a suitable container, or other nucleic acid such as one or more expression vector. The kit typically further comprises, one or more additional reagents, e.g., substrates, labels, primers, for labeling expression products, tubes and/or other accessories, reagents for collecting samples, buffers, hybridization chambers, cover slips, etc. The kit optionally further comprises an instruction set or user manual detailing preferred methods of using the kit components for discovery or application of diagnostic sets, etc.

When used according to the instructions, the kit can be used, e.g., for evaluating a disease state or condition, for evaluating effects of a pharmaceutical agent or other treatment intervention on progression of a disease state or condition in a cell or organism, or for use as a vaccine, etc.

In an additional aspect, the present invention provides system kits embodying the methods, composition, systems and apparatus herein. System kits of the invention optionally comprise one or more of the following: (1) an apparatus, system, system component or apparatus component; (2) instructions for practicing methods described herein, and/or for operating the apparatus or apparatus components herein and/or for using the compositions herein. In a further aspect, the present invention provides for the use of any apparatus, apparatus component, composition or kit herein, for the practice of any method or assay herein, and/or for the use of any apparatus or kit to practice any assay or method herein.

Additionally, the kits can include one or more translation system as noted above (e.g., a cell) with appropriate packaging material, containers for holding the components of the kit, instructional materials for practicing the methods herein and/or the like. Similarly, products of the translation systems (e.g., proteins such as HA and/or NA molecules) can be provided in kit form, e.g., with containers for holding the components of the kit, instructional materials for practicing the methods herein and/or the like. Furthermore, the kits can comprise various vaccines (e.g., produced through plasmid rescue protocols) such as live attenuated vaccine (e.g., FluMist) comprising the HA and/or NA sequences herein.

To facilitate use of the methods and compositions of the invention, any of the vaccine components and/or compositions, e.g., reassorted virus in allantoic fluid, etc., and additional components, such as, buffer, cells, culture medium, useful for packaging and infection of influenza viruses for experimental or therapeutic vaccine purposes, can be packaged in the form of a kit. Typically, the kit contains, in addition to the above components, additional materials which can include, e.g., instructions for performing the methods of the invention, packaging material, and a container.

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Materials and Methods

Generation of recombinant viruses: Wild type (wt) influenza A H1N1 viruses, A/CA/4/09 isolated from MDCK cells and A/CA/7/09 isolated from eggs, were received from Centers for Disease Control and Prevention (CDC). A/CA/4/09 egg adapted viral RNA was provided by Dr. Ziping Ye of Food and Drug Administration (FDA). The HA and NA gene segments of A/CA/4/09 and A/CA/7/09 were amplified by RT-PCR using primers that are universal to the HA and NA gene end sequences and cloned into the plasmid vector pAD3000 (Hoffman (2000) PNAS 97:6108-6113). Site-directed mutagenesis was performed to introduce specific changes into the HA genes using the QuikChange® Site-Directed Mutagenesis kit (Stratagem) and the HA sequence was confirmed by sequencing analyses. The 6:2 reassortant vaccine strains were generated by co-transfecting 8 cDNA plasmids encoding the HA and NA of the H1N1 virus and the 6 internal gene segments of cold adapted (ca) A/Ann Arbor/6/60 (MDV-A, master donor virus for type A influenza virus) into co-cultured 293T and MDCK cells. The vaccine strains used for manufacture are produced in serum-free Vero/CEK cells by electroporation. Viruses were propagated in the allantoic cavities of 10- to 11-day-old embryonated chicken ears. The HA and NA sequences of the rescued viruses were verified by sequencing of RT-PCR cDNAs amplified from vRNA.

Virus Titration:

Virus titers were measured by the fluorescence focus assay and expressed as log 10FFU (fluorescence focus units Unit)/ml (Forrest et al. (2008) *Clin Vaccine Immunol* 15:1042-1053). Virus plaque morphology was examined by plaque assay as previously described (Jin et al., (2003) *Virology* 306, 18-24).

Receptor-Binding Assay:

Chicken red blood cells (cRBCs) (HEMA Resource and Supply, Inc.) were desialylated and re-sialylated as previously described ( ). 100 µl of 10% cRBCs was incubated with 50 mU *Vibrio cholerae* neuraminidase (Sigma, St. Louis, Mo.) at 37° C. for 1 h to remove sialic acid. After three washes with 1 ml PBS, cells were resuspended in 1 ml PBS containing 1% bovine serum albumin (BSA), incubated with mU of α2,3(N)-sialyltransferase (Calbiochem, La Jolla, Calif.) or 2 mU of α2,6(N) sialyltransferase (Calbiochem, La Jolla, Calif.) for 1.5 h at 37° C., plus 1.5 CMP-SA (Sigma, St. Louis, Mo.). The resialylated cRBCs were resuspended as 0.5% (v/v) in PBS after washing three times with PBS. Haemagglutination assays (HA) were carried out in V-bottomed 96 well microliter plates for the binding activity. 50 µl of twofold serially diluted viruses were incubated with 50 µl of 0.5% cRBC, α2,3, or α2,6 resialylated cRBC at room temperature for 60 min. The HA titer was defined as the highest dilution that hemagglutinate the RBCs.

Ferret Studies:

8-10 weeks old male and female ferrets from Simonson (Gilroy, Calif.) in groups of 3 were used to assess virus replication in the respiratory tracts and for vaccine immunogenicity. Ferrets were housed individually and inoculated intranasally with 7.0 log 10FFU of virus per 0.2 ml dose.

Serum Antibody Detection by HAI Assay:

H1N1-specific antibody level in post-infected ferret sera against homologous and heterologous viruses was determined by HAI assay. Prior to serologic analysis, ferret sera were treated with receptor-destroying enzyme (RDE) (Denka Seiken, Tokyo, Japan) that was reconstituted in 10 mL of 0.9% NaCl per vial. 0.1 mL serum was mixed with 0.15 mL RDE and incubated at 37° C. for 18 hr and adjusted to a final 1:4 dilution by adding 0.15 mL of 0.9% sodium citrate followed by incubation at 56° C. for 45 min. Strain-specific serum HAI titers were determined using 0.5% tRBC and the HAI titers are presented as the reciprocal value of the highest serum dilution that inhibited hemagglutination.

Results

Generation of Reassortant Candidate Vaccine Strains

The HA and NA gene segments from wt A/CA/4/09 were cloned from infected MDCK cell RNA following RT-PCR amplification. A total of 12 cDNA clones from each HA or NA were found to be identical by nucleotide sequence analysis. Plasmids representing this HA sequence and the NA sequence of wt A/CA/4/09 were transfected into 293/MDCK cells together with plasmids representing the six internal protein gene segments of MDV-A, however, no viable reassortant progeny could be recovered either on MDCK cells or eggs. The HA cDNAs cloned from the wt A/CA/4/09 egg isolate were heterogeneous at two amino acid positions (Table 3). From 12 clones analyzed, the following changes were observed: 42% L191I, 50% Q223R, one (8%) had both L191I and Q223 R. Plasmids representing these different HA sequences were combined and transfected into 293/MDCK cells with the MDV-A internal protein genes and reassortant viruses were readily rescued.

The HA plasmid cloned from A/CA/7/09 that did not have amino acid change at residues of 222 or 223 could be rescued to produce progeny virus. This indicated that T197A change in CA/7/09 was responsible for the efficient rescue of A/CA/7/09. Other A/CA/7/09 clones had changes of either D222G or Q223R, viruses containing D222G or Q223R, in HA were also rescued. Due to the high degree of similarity between the HAs of A/CA/4/09 and A/CA/7/09 and since the NA sequences were identical between these two strains, the variants derived from A/CA/7/09 were developed further.

TABLE 3

HA sequences and virus titers of novel H1N1 variants

| Virus | Passage History | wt virus H1# H3# | Amino acid at position | | | | % clones | Virus titer in eggs* ($\log_{10}$FFU/ml ± SE) |
|---|---|---|---|---|---|---|---|---|
| | | | 191 194 | 197 200 | 222 225 | 223 226 | | |
| A/CA/04/09 | MDCK 2x | swt | L | T | D | Q | NA | NA |
| | | variant 1 | L | T | D | Q | 100 | Not rescued |
| | Egg 2x | variant 2 | I | T | D | Q | 42 | 7.4 ± 0.09 |
| | | variant 3 | L | T | D | R | 50 | 7.8 ± 0.15 |
| | | variant 7 | I | T | D | R | 8 | 7.8 ± 0.40 |
| A/CA/07/09 | Egg 2x | swt | L | A | D/G | Q/R | NA | NA |
| | | variant 4 | L | A | D | Q | 45 | 7.8 ± 0.27 |
| | | variant 5 | L | A | G | Q | 34 | 7.4 ± 0.14 |
| | | variant 6 | L | A | D | R | 21 | 7.7 ± 0.14 |

*Virus titers are mean titers from at least three virus stocks;
NA: not applicable Three days after infection, ferrets were euthanized, and the lungs and nasal turbinates (NT) were harvested. Virus titers in the lung and NT were determined by the EID50 assay and expressed as 50% egg infectious dose per grain of tissue (log 10EID50/g). Ferrets that were assigned for immunogenicity studies were bled on days 14, 21 and 28 days postinfection and sera were assayed for antibody titers by HAI.

Selection of Vaccine Strains with Better Growth in Embryonated Chicken Eggs.

Figure 1B:
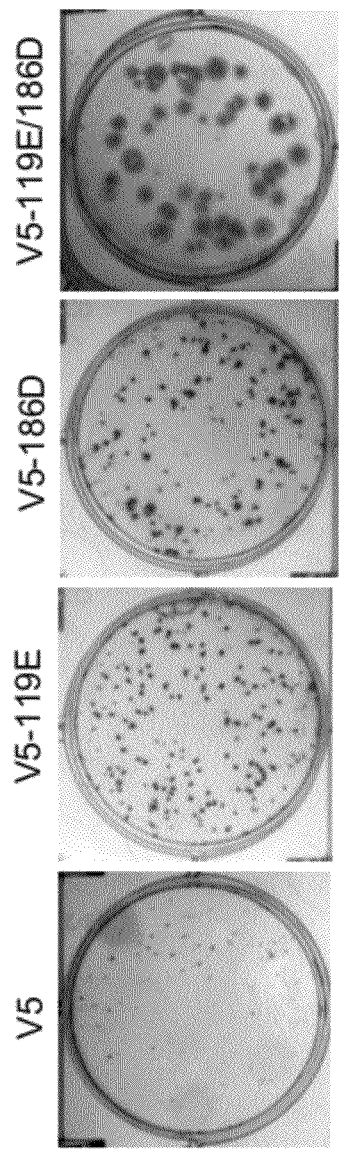

As shown in Table 3, the rescued A/CA/4/09 and A/CA/7/09 reassortant vaccine strains replicated in chicken embryonated eggs at titers of 7.4 to 7.8 $\log_{10}$ FFU/ml, which was lower than the seasonal H1N1 vaccine strains by at least 10-fold. Further, the recovered A/CA/7/09 reassortant vaccine candidates formed very small plaques in MDCK cells. To improve the vaccine virus growth MDCK cells and eggs, A/CA/7/09 candidates (V5 and V6) were passaged twice in MDCK cells at moi of 4.0, 0.4 and 0.04, then the viruses present in the supernatants were examined by plaque assay. All the MDCK-passaged viruses contained plaques that were much larger (2-4 mm) than the parental viruses (FIG. 1). The HA gene segment of twelve plaques from MDCK passaged V5 and V6 vaccine candidates were sequenced. The HA of each of the lame plaque morphology isolates had single amino acid changes at one of the following positions: K119N or K119E, K153E, K154E derived from V5 and A186D from V6.

The HA sequence of A/CA/7/09 was also compared with two earlier H1N1 viruses that were originated from swine, A/swine/Iowa/1/1976 and A/swine/1931, and a recent human H1N1 virus, A/South Dakota/6/07 (A/SD/07). As shown in FIG. 2, K119, K153 and K154 are highly conserved among the swine H1N1 viruses. A/SD/6/07 also contained K119 and K154 residues. The amino acids at 186 are more diverse among the four viruses shown in FIG. 2. A previous study (Both et al. (1983) *Proc Natl Acad Sci USA* 80:6996-7000) showed that the G155E change is responsible for the high growth of the virus in eggs. These data indicate that the negatively charged E residue in the 153-155 region is preferred for virus replication in MDCK cells and eggs. To examine if the G155E change previously reported for A/NJ/76 virus could also improve virus replication of A/CA/7/09 eggs, G155E was introduced into V5 and V6. In addition, to confirm that the amino acids identified in the large plaques conferred virus growth advantage in eggs, each of the identified mutation was introduced into the HA and reassortant vaccine candidate strains were rescued. Moreover, the A186D change identified in V6 was also introduced into V5 and V5-119E. Similarly, the 119N mutation found in V5 was also introduced into V6 and V6-186D to evaluate the influence of single and double amino acid change on virus replication in eggs. Similarly, the 119N mutation found in V5 was also introduced into V6 and V6-186D to evaluate the influence of single and double amino acid changes on virus replication in eggs. HA sequence analysis also showed that A/CA/09 strains contained a unique glycosylation site at residue 278 (FIG. 2). To evaluate if this additional glycosylation site affected virus growth, a T278K change was introduced into V5 and V6, respectively.

The rescued viruses were examined for their growth in eggs. As shown in Table 4, most of the variants containing the introduced HA mutations grew significantly better than V5 and V6. V5-278K and V6-278K had titers of 7.6 and 7.7 $\text{Log}_{10}$ FFU/ml that were similar to V5 and V6. Thus, removal of the 278 glycosylation site had minimal impact on virus titers in eggs. The changes at the 119, 186, 153, 154, 155 and 186 sites increased virus titers by 0.2 to 1.2 $\log_{10}$ FFU/ml. The combined 119E and 186D change in V5 resulted in a slightly higher titer than either 119E or 186D on their own.

TABLE 4

A/CA/07/09 HA variants identified from MDCK cells and introduced by reverse genetics.

| Virus | Amino acid at residue (H1# and H3#) | | | | | | | | Virus titer in eggs ($\log_{10}$FFU/ml ± SE) |
|---|---|---|---|---|---|---|---|---|---|
| | 119 / 122 | 153 / 156 | 154 / 157 | 155 / 158 | 186 / 189 | 222 / 225 | 223 / 226 | 278 / 280 | |
| V5 | K | K | K | G | A | G | Q | T | 7.4 ± 0.14 |
| V6 | | | | | | | R | | 7.7 ± 0.14 |
| V5-119N | N | | | | | G | | | 8.3 ± 0.06 |
| V5-119E | E | | | | | G | | | 8.3 ± 0.07 |
| V5-153E | | E | | | | G | | | 8.3 ± 0.05 |
| V5-154E | | | E | | | G | | | 8.6 ± 0.05 |
| V6-186D | | | | | D | | R | | 8.4 ± 0.06 |
| V5-186D | | | | | D | G | | | 8.3 ± 0.15 |
| V5-119E/186D | E | | | | D | G | | | 8.5 ± 0.06 |
| V6-119N | N | | | | | | R | | 7.9 ± 0.20 |
| V6-119N/186D | N | | | | D | | R | | 8.1 ± 0.09 |
| V5-155E | | | | E | | G | | | 8.4 ± 0.11 |
| V5-278K | | | | | | G | | K | 7.6 ± 0.19 |
| V6-155E | | | | E | | | R | | 8.4 ± 0.19 |
| V6-278K | | | | | | | R | K | 7.7 ± 0.27 |

Amino acid residue numbers of H1 HA are shown in row 2; corresponding amino acid residue numbers in H3 HA are shown in row 3.
*Virus titers are mean titers from at least three virus stocks Evaluation of Vaccine Variants for their Antigenicity To determine if any of the amino acid changes introduced into the H1 HA affected virus antigenicity, A/CA/7/09 variants were evaluated for their reactivity with different postinfection ferret sera using the HAI assay (Table 5). The cold adapted (ca) viruses, A/CA/4/07 with 223R residue (V3), A/CA/7/09 with 222G residue (V5) and A/CA/7/09 with 223R residue (V6), reacted similarly to the 4 reference sera from ferrets immunized with wt A/CA/4/09, ca A/CA/4/09 (V3), ea A/CA/7/09 (V5) and ca A/CA/07/09 (V6). The variants with amino acid changes introduced into V5 at positions 119 and 186 had antigenicity similar to V5. However, the viruses with the changes at 153, 154 and 155 positions had much lower reactivity with these sera, a titer reduction of greater than 4-fold was detected. Thus, these data demonstrate that the mutations at residues 153-154 should not be present in the vaccine strain. Changes at the 119 and 186 positions could be introduced into the vaccine strain without affecting virus antigenicity.

TABLE 5

Antigenicity of A/CA/7/09 HA variants.
HAI assay was performed with turkey RBC.

| | Post infection ferret serum | | | |
|---|---|---|---|---|
| Virus | A/CA/4/09 wt | A/CA/4/09 ca 223R (V3) | ACA/7/09 222G (V5) | A/CA/7/09 223R (V6) |
| CA04 V3 | 8192 | 1024 | 2048 | 1024 |
| CA07 V5 | 8192 | 1024 | 1024 | 1024 |
| CA07 V6 | 4096 | 1024 | 1024 | 512 |
| V5-119N | 8192 | 512 | 2048 | 1024 |
| V5-119E | 4096 | 512 | 1024 | 512 |
| V5-153E | 256 | <32 | 128 | 64 |
| V5-154E | 512 | <32 | 128 | 128 |
| V5-155E | 256 | <32 | 128 | 128 |
| V5-186D | 8192 | 1024 | 2048 | 1024 |
| V5-278K | 4096 | 512 | 1024 | 512 |
| V5-119E/186D | 8192 | 1024 | 2048 | 1024 |

A/CA/7109 Vaccine Candidates are Attenuated but Immunogenic in Ferrets

To evaluate A/CA/7/09 vaccine variants for their attenuated phenotype and their ability to induce antibody responses, ferrets were inoculated with 7.0 $\log_{10}$ FFU of virus intranasally in 0.2 ml of dose volume and virus replication in the upper and lower respiratory tracts of ferrets was determined by $EID_{50}$ assay. As shown in Table 6, all A/CA/7/09 variants replicated efficiently in the NT tissues, but no virus was detected in the lungs. These data confirmed that these viruses were attenuated in ferrets, a characteristic phenotype conferred by the six internal protein gene segments of MDV-A.

Ferret post-infection serum was collected on day 14 after intranasal inoculation and antibody titers were evaluated by HAI assay (Table 6). All V5 variants were very immunogenic and induced H1N1-specific antibody responses, with the HAI titers ranging from 256 to 1024. Several V6 variants were also evaluated for their immunogenicity and were found to be less immunogenic than V5 (data not shown). The variants with the mutations at residues 119 and 186 maintained antigenicity similar to wt virus and did not react well with 154E and 155E variants. Sera from ferrets infected with the 154E and 155E variants infected ferret sera also did not react well with wt virus, V5, and V5 variants with 119E and 186D changes; their titer differences were within 2-fold. V5-154E and 155E postinfected ferret sera had homologous HAI titers more than 4-fold higher than the other variants. Interestingly, the mutation at 186D resulted in a greater reduction in reactivity with 154E and 155E variants. These data demonstrate that the 119 and 186 HA variants of A/CA/07/09 (H1N1) conferred high growth in eggs without altering virus antigenicity or immunogenicity, making them potential vaccine candidates for the swine-origin H1N1 virus.

TABLE 6

Replication of A/CA/7/09 HA variants in the respiratory tracts of ferrets and their immunogenicity.

| | Virus titer | | GMT of HAI antibody to the indicated antigen | | | | | | |
|---|---|---|---|---|---|---|---|---|---|
| | ($\log_{10}EID_{50}/g \pm SE$) | | | | | | 119E | | |
| Virus | NT | lung | V5 | 119E | 119N | 186D | 186D | 154E | 155E |
| V5 | 4.0 ± 0.23 | <1.5 | <u>512</u> | 406 | 406 | 323 | 323 | 64 | 256 |
| V5-119E | 4.2 ± 0.33 | <1.5 | 813 | <u>645</u> | 645 | 323 | 406 | 64 | 256 |
| V5-119N | 4.5 ± 0.33 | <1.5 | 256 | 203 | <u>256</u> | 256 | 323 | 64 | 161 |
| V5-186D | 4.9 ± 0.20 | <1.5 | 813 | 645 | 645 | <u>645</u> | 645 | 128 | 256 |
| V5-119E/186D | 4.7 ± 0.29 | <1.5 | 512 | 406 | 512 | 512 | <u>645</u> | 64 | 256 |
| V5-154E | 5.7 ± 0.29 | <1.5 | 161 | 323 | 323 | 64 | 81 | <u>512</u> | 1024 |
| V5-155E | 5.0 ± 0.20 | <1.5 | 128 | 203 | 161 | 51 | 64 | 203 | <u>1024</u> |
| A/CA/7/09 wt | NA | NA | 512 | 512 | 645 | 645 | 406 | 102 | <u>323</u> |

Ferret serum was collected on day 14 of postinfection and HAI assay was performed with turkey RBC.

Receptor Binding Specificity of A/CA/7/09 Variants

Growth of wild type A/CA/4/09 and A/CA/7/09 viruses in eggs resulted in amino acid change in the HA receptor binding site, D222G and Q223R. These positions have been previously identified in other H1N1 strains following egg passages and are responsible for the HA receptor binding specificity. To determine whether the vaccine virus variants have different receptor binding specificity, V5, V6 and V5-119 and V5-186 variants were evaluated for their receptor binding specificity by the RBC binding assay (Table 7), V4 (without 222 and 223 change) preferred to bind to α2-6 SA than α2-3 SA. V5 (D222G) bound to α2-3 and α2-6 SA resialylated RBC equally well. However, V6 (Q223R) could only bind to α2-3 SA resialylated RBC, confirming that these two residues affected virus receptor binding specificity. The V5-119E/N and V5-186D viruses had similar binding specificity as V5. The double HA mutant V5-119E/186D preferred binding to α2-6 SA better than α2-3 SA. The 119E and 186D residues introduced into V6 could not restore their binding to α2-6 SA (data not shown). Thus, the change in the 119 and 186 residues do not significantly affect virus receptor binding specificity.

TABLE 7

Receptor binding specificity of A/CA/07/09 vaccine variants

| Virus | Untreated | α2,3-SA | α2,6-SA | desialylated |
|---|---|---|---|---|
| V4 | 128 | 16 | 128 | <2 |
| V5 | 512 | 64 | 64 | <2 |
| V6 | 512 | 512 | <2 | <2 |
| V5-119N | 512 | 64 | 64 | <2 |
| V5-119E | 512 | 128 | 128 | <2 |
| V5-186D | 512 | 32 | 64 | <2 |
| V5-119E/186D | 512 | 16 | 64 | <2 |

Figure 3A:
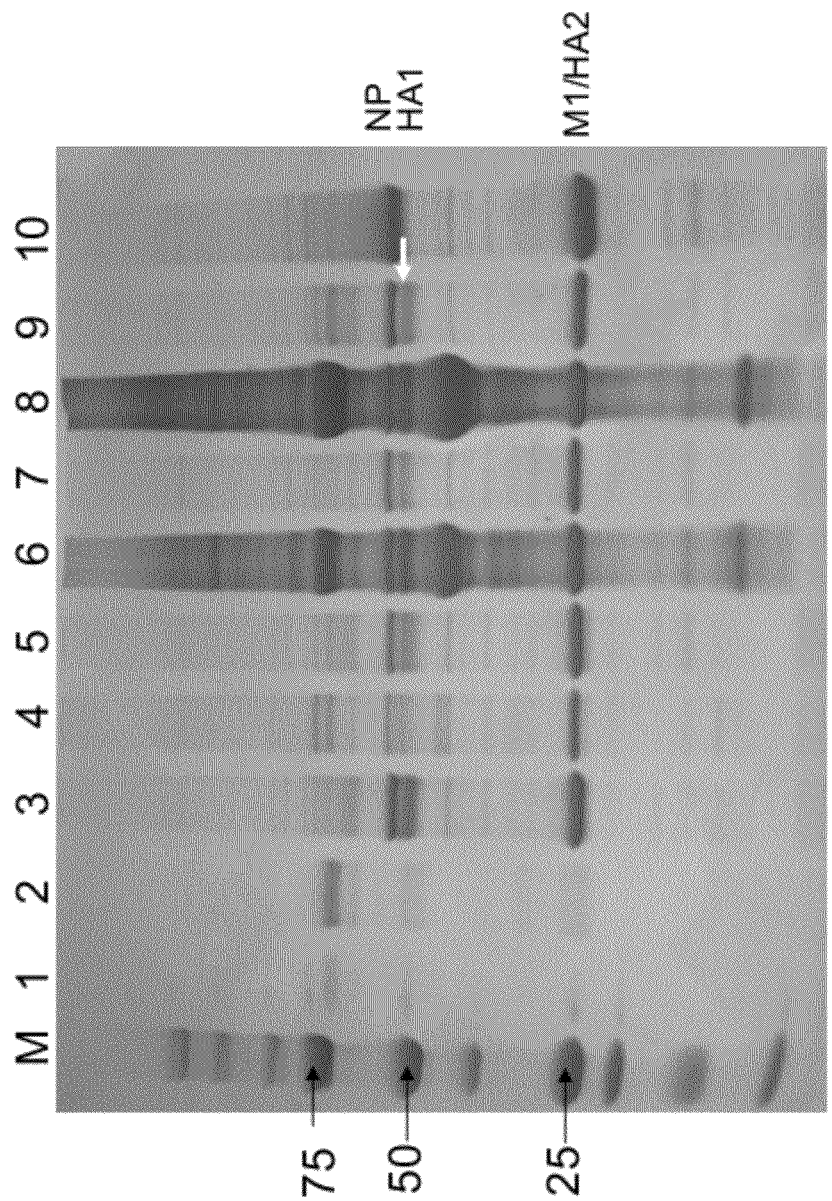
FIG. 3. Protein composition of virus preparations purified from embryonated eggs.

Protein Composition of A/CA/7/09 Reassortants 13 ml allantoic fluid harvested from infected eggs was pelleted through 2 ml of 30% sucrose cushion at 25 k rpm for 1 hr. Virus pellet was resuspended in 0.2 ml PBS. 5 ul virus suspension was loaded on 4-20% polyacrylamide gel and stained with Coomassie blue. The order of samples was as follows:
FIG. 3A
Lane 1. Recombinant HA A/NC/20/99 0.5 ug
Lane 2. Recombinant HA A/NC/20/99 2 ug
Lane 3. MDVA-V5-119E/186D (FFA 8.6)
Lane 4, MDVA-V6 (FFA 7.9)
Lane 5, MDVA-V6-186D (FFA 8.1)
Lane 6, PR8-V5-119E/186D (FFA 8.2)
Lane 7. PR8-V6 (FFA 7.8)
Lane 8. PR8-V6-186D (FFA 8.5)
Lane 9. NYMC X-179A (FFA 8.5)
Lane 10. PR8 South Dakota (FFA 8.7)
FIG. 3B
Lane 1, NYMC X-179A (FFA 8.5)
Lane 2, MDVA-V5-119E/186D (FFA 8.6)
Lane 3. MDVA-V5-119E/186D/PA-S395N (FFA8.9)
Lane 4. South Dakota (FFA 8.7)
FFA and peak titer values were determined using standard methods. Reassortant viruses with "MDVA" in their designation comprise 6 internal genome segment of A/Ann Arbor/6/60. Reassortant viruses with "PR8" in their designation comprise 6 internal genome segment of PR8.
Comparison of HA Protein Yield of A/California/7/09 Variants 6:2 reassortant influenza viruses comprising the 6 internal genome segments from PR8 and the HA and NA genome segments from A/CA/7/09 were generated. Additional 6:2 reassortant viruses comprising the 6 internal genome segments from PR8, the NA genome segment from A/CA/7/09, and an HA genome segment encoding an H1 HA variant polypeptide described herein were generated. The 6:2 reassortant viruses comprising different A/CA/7/09 HA variants, along with A/Texas/5/2009 RG15 (A/TX/7/09 RG15) and A/California/07/09 NYMC X179A, were expanded in chicken embryonated eggs and their peak titers were determined by FFA. Virus strains assayed are shown in Table 8. 6:2 PR8-South Dakota is a 6:2 reassortant virus comprising the 6 internal genome segments from PR8 and the HA and NA genome segments from A/South Dakota/6/07. 6:2 AA-V5-119E/186D is a 6:2 reassortant virus comprising the 6 internal genome segments from A/Ann Arbor/6/60, the NA genome segment from A/CA/7/09, and the V5-119E/186D variant HA genome segment. PR8 reassortant viruses comprising H1 HA variant genome segments described herein had comparable titers to X179A, the highest yield strain available for TIV manufacture.

TABLE 8

Peak titer of 6:2 reassortant H1N1 viruses in embryonated eggs.

| Virus | Peak titer ($\log_{10}$ FFU/ml) |
|---|---|
| 6:2 PR8-V6 | 8.1 |
| 6:2 PR8-V6-186D | 8.5 |
| 6:2 PR8-V5-119E/186D | 8.6 |
| A/CA/7/09 X179A. | 8.5 |
| A/TX/7/09 RG15 | 6.6 |
| 6:2AA-V5-119E/186D | 8.6 |
| 6:2 PR8-South Dakota | 9.2 |

In addition to measuring peak titers, we also determined the HA protein yield of some of the reassortant viruses listed in Table 8. Selected viruses were amplified by infecting 50 eggs each with an MOI of $10^3$ FFU/egg. Viruses were harvested after incubation at 33° C. for 62 hrs. Equal amount of allantoic fluid 250 ml) were then purified by sucrose gradient. Virus proteins were analyzed by SDS PAGE followed by Coomassie blue staining.

Figure 4:
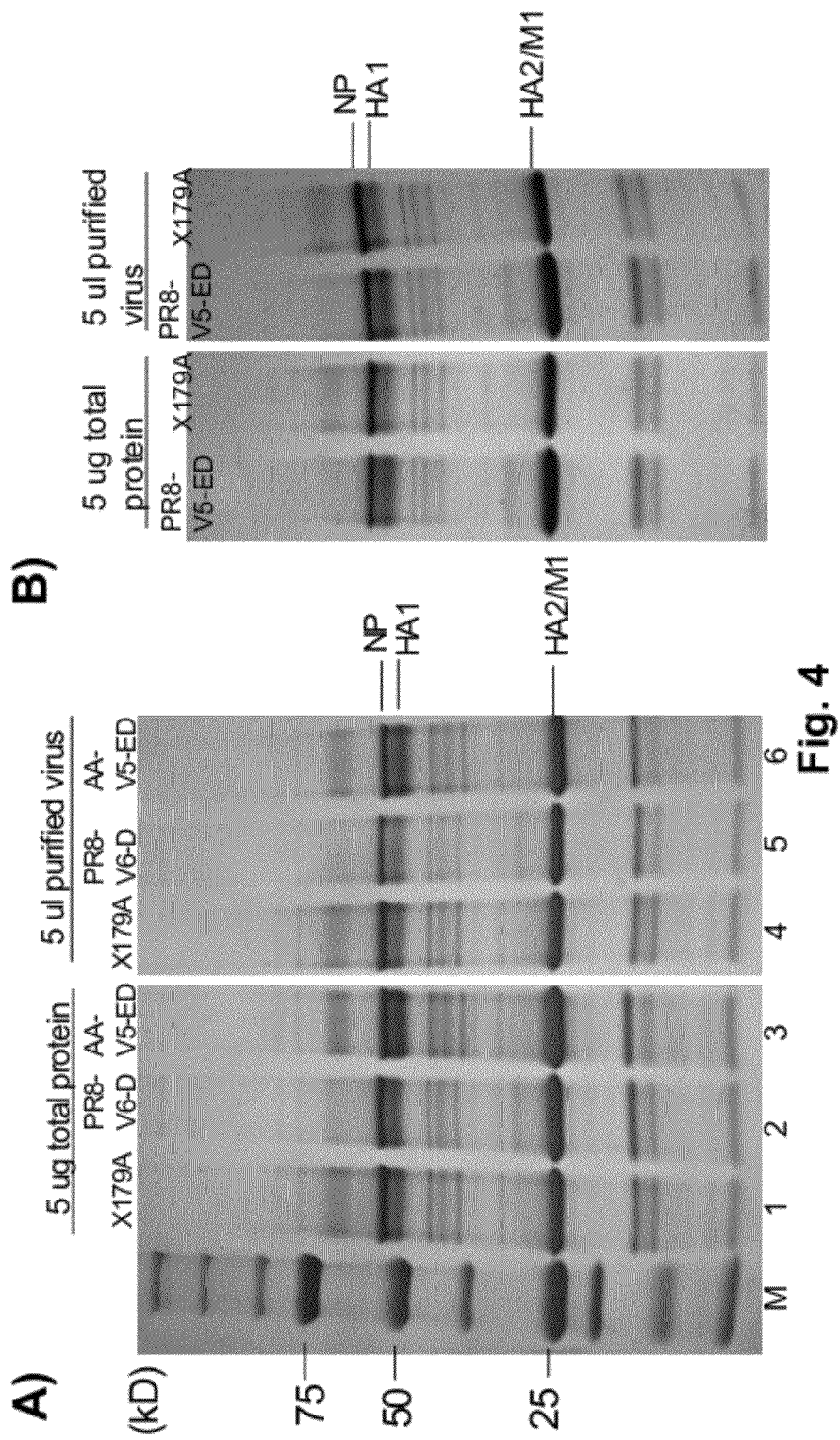
FIG. 4. Protein composition of virus preparations purified from embryonated eggs.

A representative sample of the results is shown in FIG. 4. As shown in FIG. 4A, the total protein yield of X179A, 6:2 PR8-V6-186D and 6:2AA-V5-119E/186D was 460, 300, and 350 ug respectively. 6:2 AA-V5-119E/186D had the highest HA protein yield, even though 6:2 AA-V5-119E/186D had a lower total protein yield than A/CA/7/09 X179A. The lower total protein yield observed for 6:2 AA-V5-119E/186D in this experiment was likely due to assay variation. As shown in FIG. 4B, the total protein yield of 6:2 PR8-V5-119E/186D and X179A was 780 and 720 ug respectively. The HA protein yield of 6:2 PR8-V5-119E/186D was also higher than that of A/CA/7/09 X179A.

Reassortant Viruses Comprising the PR8 Backbone and a Variant A/California/7/09 H1 Polypeptide Additional 6:2 reassortant influenza viruses comprising 6 internal genome segments from PR8, a variant of the A/CA/7/09 H1 HA genome segment, and the A/CA/7/09 NA genome segment were generated. The H1 HA amino acid variations are summarized in Table 9.

TABLE 9

Reassortant viruses comprising variant A/CA/7/09 H1 HA and the PR8 backbone.

| Virus (HA) | H1 HA residue # | | | | | Antigenicity |
|---|---|---|---|---|---|---|
| | 119 | 186 | 190 | 222 | 223 | 273 | |
| PR8-A (V6-186D) | K | D | R | D | R | H | no change |
| PR8-B (V5-119E/ 186D/190R) | E | D | S | G | Q | H | reduced |
| PR8-C (V6-186D/ 273Y) | K | D | R | D | R | Y | no change |
| PR8-D (V5-119E/ 186D) | E | D | R | G | Q | H | no change |

Figure 5A:
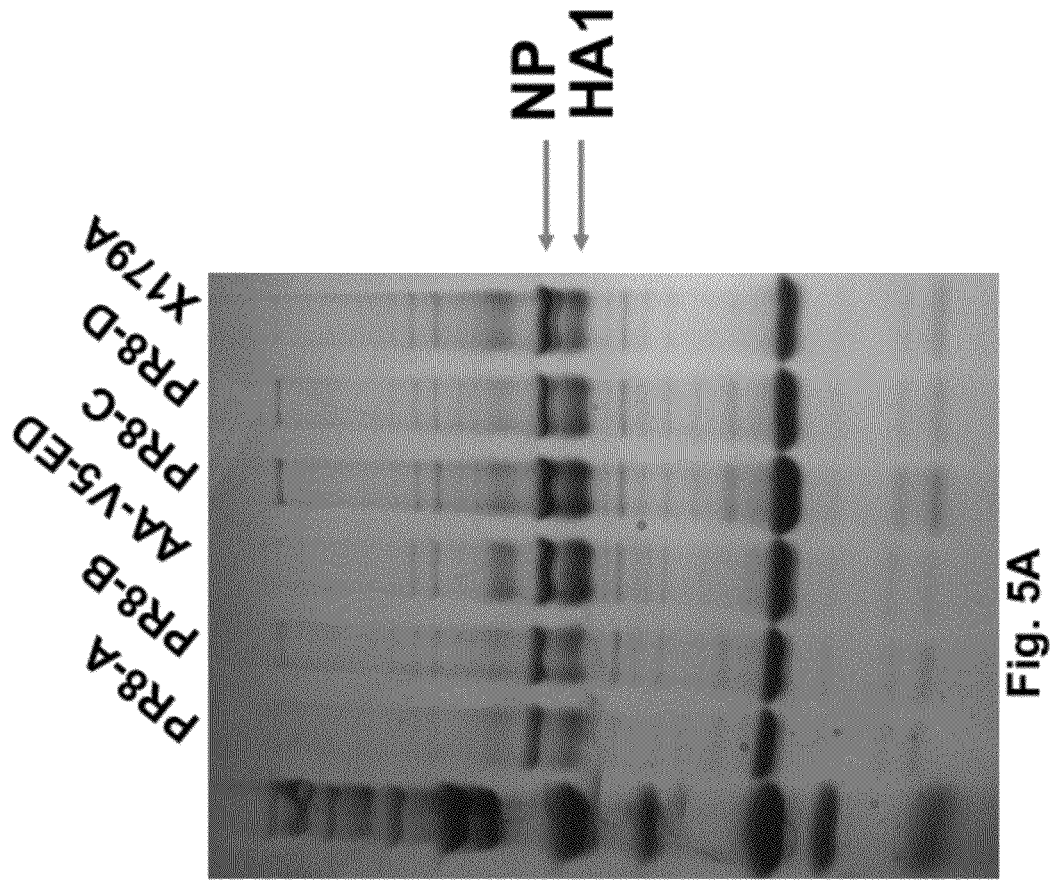
FIG. 5. Protein composition of purified virus preparations harvested from embryonated eggs at (A) 48 hrs and (B) 60 hrs.
Figure 5B:
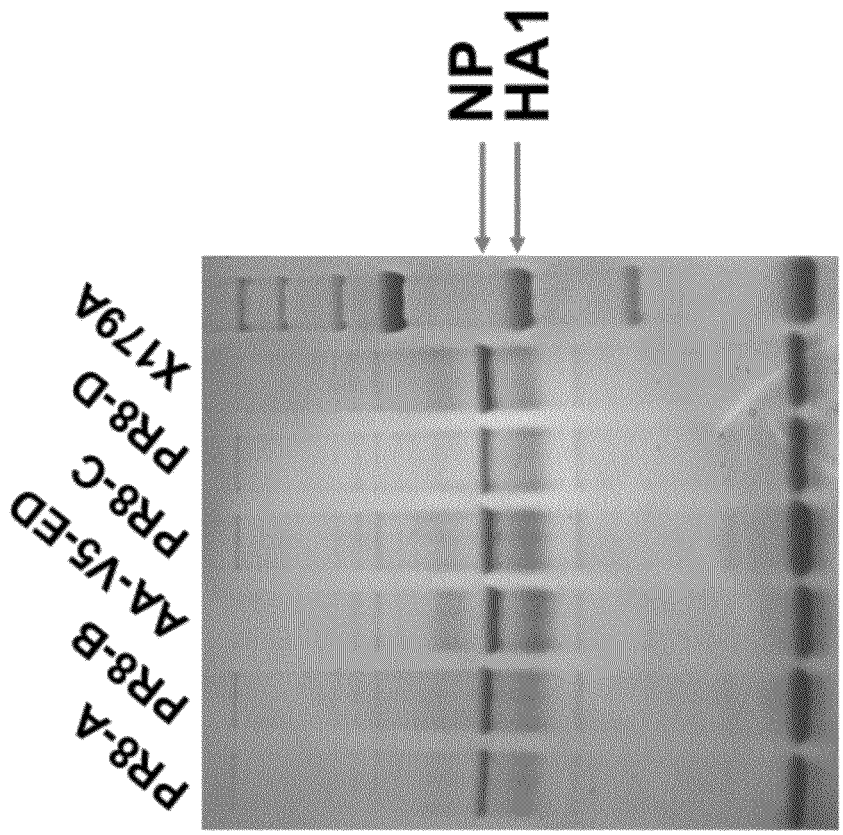

Out of the variant HAs tested, only changes in V5-119E/186D/190R reduced antigenicity (Table 9). The 6:2 reassortant viruses comprising different A/CA/7/09 HA variants were expanded in chicken embryonated eggs to determine the HA protein yield. Viruses were harvested after incubation at 33° C. for 48 hrs (FIG. 5A) or 60 hrs (FIG. 5B). Viruses were then purified by sucrose gradient sedimentation. Protein composition of the purified viruses was analyzed by SDS-PAGE followed by Coomassie blue staining. Individual lanes were loaded with samples comprising either an equal amount of purified virus (FIG. 5A) or the virus purified from an equal volume of harvested allantoic fluid (FIG. 5B). Samples prepared from AA-V5-ED (comprising the V5-119E/186D variant HA and the A/Ann Arbor/6/60 backbone) and X179A viruses were included as controls. The PR8-C virus produced higher yield of the HA polypeptide than X179A.

Figure 6:
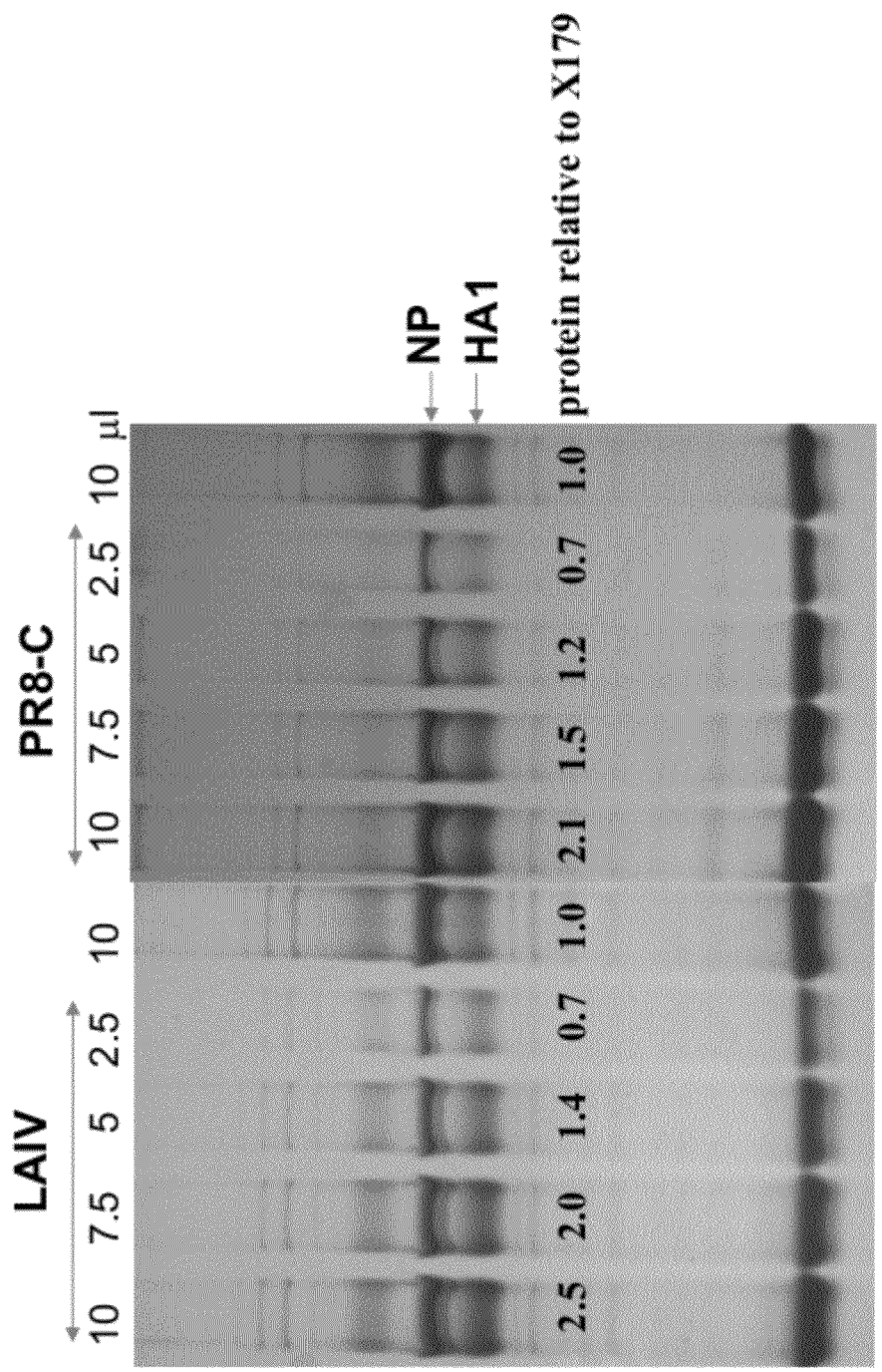
FIG. 6. Quantitative comparison of the HA1 protein produced by two reassortant H1N1 viruses in embryonated eggs.

The HA yield of PR8-C and AA-V5-ED relative to the HA yield of X179A was further measured using SDS-PAGE followed by Coomassie blue staining. Various volumes (10, 7.5, 5 and 2.5 microliter) of the PR8-C and AA-V5-ED samples and 10 microliter of the X179A sample were analyzed by SDS-PAGE. The relative amount of HA1 protein found in each sample was measured using image analysis software. The result of the measurement is shown in FIG. 6. The AA-V5-ED and PR8-C viruses produce 1-1.5 times more HA protein than X179A.

While the foregoing invention has been described in some detail thr purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes. In particular, the following patent applications are incorporated by reference in their entirety for all purposes: US Provisional Application Nos. 61/220,426 filed Jun. 25, 2009, 61/227,986 filed on Jul. 23, 2009, and 61/234,021 filed on Aug. 14, 2009.

```
Sequences:

SEQ ID NO 1 hemagglutinin A/CA/07/09 (V5) amino acid sequence
  dtl cigyhannst dtvdtvlekn vtvthsvnll
edkhngklck lrgvaplhlg kcniagwilg npeceslsta sswsyivetp
ssdngtcypg dfidyeelre qlssyssfer feifpktssw pnhdsnkgvt
aacphagaks fvknliwlvk kgnsypklsk syindkgkev lvlwgihhps
tsadqqslyq nadayvfvgs sryskkfkpe iairpkvrgq egrmnyywtl
vepgdkitfe atgnlvvpry afamernags giiisdtpvh dcnttcqtpk
gaintslpfq nihpitigkc pkyvkstklr latglrnips iqsrglfgai
agfieggwtg mvdgwygyhh qneqgsgyaa dlkstqnaid eitnkvnsvi
ekmntqftav gkefnhlekr ienlnkkvdd gfldiwtyna ellvllener
tldyhdsnvk nlyekvrsql knnakeigng cfefyhkcdn tcmesvkngt
ydypkyseea klnreeidgv klestriyqi laiystvass lvlvvslgai
sfwmcsngsl qcrici SEQ ID NO 2 hemagglutinin A/CA/07/09 (V5) nt sequence
    1   agcaaaagca ggggaaaaca aaagcaacaa aaatgaaggc aatactagta
   51   gttctgctat atacatttgc aaccgcaaat gcagacacat
        tatgtatagg
  101   ttatcatgcg aacaattcaa cagacactgt agacacagta
        ctagaaaaga
  151   atgtaacagt aacacactct gttaaccttc tagaagacaa
        gcataacggg
  201   aaactatgca aactaagagg ggtagcccca ttgcatttgg
        gtaaatgtaa
  251   cattgctggc tggatcctgg gaaatccaga gtgtgaatca
        ctctccacag
  301   caagctcatg gtcctacatt gtggaaacac ctagttcaga
        caatggaacg
  351   tgttacccag gagatttcat cgattatgag gagctaagag
        agcaattgag
  401   ctcagtgtca tcatttgaaa ggtttgagat attccccaag
        acaagttcat
  451   ggcccaatca tgactcgaac aaaggtgtaa cggcagcatg
        tcctcatgct
  501   ggagcaaaaa gattctacaa aaatttaata tggctagtta
        aaaaaggaaa
  551   ttcataccca aagctcagca aatcctacat taatgataaa
        gggaaagaag
  601   tcctcgtgct atggggcatt caccatccat ctactagtgc
        tgaccaacaa
```

-continued

| | Sequences: |
|---|---|
| 651 | agtctctatc agaatgcaga tgcatatgtt tttgtggggt catcaagata |
| 701 | cagcaagaag ttcaagccgg aaatagcaat aagacccaaa gtgagggggtc |
| 751 | aagaagggag aatgaactat tactggacac tagtagagcc gggagacaaa |
| 801 | ataacattcg aagcaactgg aaatctagtg gtaccgagat atgcattcgc |
| 851 | aatggaaaga aatgctggat ctggtattat catttcagat acaccagtcc |
| 901 | acgattgcaa tacaacttgt caaacaccca agggtgctat aaacaccagc |
| 951 | ctcccatttc agaatataca tccgatcaca attggaaaat gtccaaaata |
| 1001 | tgtaaaaagc acaaaattga gactggccac aggattgagg aatatcccgt |
| 1051 | ctattcaatc tagaggccta tttggggcca ttgccggttt cattgaaggg |
| 1101 | gggtggacag ggatggtaga tggatggtac ggttatcacc atcaaaatga |
| 1151 | gcagggtca ggatatgcag ccgacctgaa gagcacacag aatgccattg |
| 1201 | acgagattac taacaaagta aattctgtta ttgaaaagat gaatacacag |
| 1251 | ttcacagcag taggtaaaga gttcaaccac ctggaaaaaa gaatagagaa |
| 1301 | tttaaataaa aaagttgatg atggtttcct ggacatttgg acttacaatg |
| 1351 | ccgaactgtt ggttctattg gaaaatgaaa gaactttgga ctaccacgat |
| 1401 | tcaaatgtga agaacttata tgaaaaggta agaagccagc taaaaaacaa |
| 1451 | tgccaaggaa attggaaacg gctgctttga attttaccac aaatgcgata |
| 1501 | acacgtgcat ggaaagtgtc aaaaatggga cttatgacta cccaaaatac |
| 1551 | tcagaggaag caaaattaaa cagagaagaa atagatgggg taaagctgga |
| 1601 | atcaacaagg atttaccaga ttttggcgat ctattcaact gtcgccagtt |
| 1651 | cattggtact ggtagtctcc ctgggggcaa tcagtttctg gatgtgctct |
| 1701 | aatgggtctc tacagtgtag aatatgtatt taacattagg atttcagaag |
| 1751 | catgagaaaa acacccttgt ttctact |

SEQ ID NO 3 hemagglutinin A/CA/07/09 variant V5-186D nt sequence

| | |
|---|---|
| 1 | agcaaaagca ggggaaaaca aaagcaacaa aaatgaaggc aatactagta |
| 51 | gttctgctat atacatttgc aaccgcaaat gcagacacat tatgtatagg |
| 101 | ttatcatgcg aacaattcaa cagacactgt agacacagta ctagaaaaga |
| 151 | atgtaacagt aacacactct gttaaccttc tagaagacaa gcataacggg |
| 201 | aaactatgca aactaagagg ggtagcccca ttgcatttgg gtaaatgtaa |
| 251 | cattgctggc tggatcctgg gaaatccaga gtgtgaatca ctctccacag |
| 301 | caagctcatg gtcctacatt gtggaaacac ctagttcaga caatggaacg |
| 351 | tgttacccag gagatttcat cgattatgag gagctaagag agcaattgag |
| 401 | ctcagtgtca tcatttgaaa ggtttgagat attccccgag acaagttcat |
| 451 | ggcccaatca tgactcgaac aaaggtgtaa cggcagcatg tcctcatgct |
| 501 | ggagcaaaaa gcttctacaa aaatttaata tggctagtta aaaaaggaaa |
| 551 | ttcataccca aagctcagca atcctacat taatgataaa gggaaagaag |
| 601 | tcctcgtgct atggggcatt caccatccat ctactagtga tgaccaacaa |
| 651 | agtctctatc agaatgcaga tgcatatgtt tttgtggggt catcaagata |
| 701 | cagcaagaag ttcaagccgg aaatagcaat aagacccaaa gtgagggtc |

-continued

| | Sequences: |
|---|---|
| 751 | aagaagggag aatgaactat tactggacac tagtagagcc gggagacaaa |
| 801 | ataacattcg aagcaactgg aaatctagtg gtaccgagat atgcattcgc |
| 851 | aatggaaaga aatgctggat ctggtattat catttcagat acaccagtcc |
| 901 | acgattgcaa tacaacttgt caaacaccca agggtgctat aaacaccagc |
| 951 | ctcccatttc agaatataca tccgatcaca attggaaaat gtccaaaata |
| 1001 | tgtaaaaagc acaaaattga gactggccac aggattgagg aatatcccgt |
| 1051 | ctattcaatc tagaggccta tttggggcca ttgccggttt cattgaaggg |
| 1101 | gggtggacag ggatggtaga tggatggtac ggttatcacc atcaaaatga |
| 1151 | gcagggtca ggatatgcag ccgacctgaa gagcacacag aatgccattg |
| 1201 | acgagattac taacaaagta aattctgtta ttgaaaagat gaatacacag |
| 1251 | ttcacagcag taggtaaaga gttcaaccac ctggaaaaaa gaatagagaa |
| 1301 | tttaaataaa aaagttgatg atggtttcct ggacatttgg acttacaatg |
| 1351 | ccgaactgtt ggttctattg gaaaatgaaa gaactttgga ctaccacgat |
| 1401 | tcaaatgtga gaacttata tgaaaaggta agaagccagc taaaaaacaa |
| 1451 | tgccaaggaa attggaaacg gctgctttga attttaccac aaatgcgata |
| 1501 | acacgtgcat ggaaagtgtc aaaaatggga cttatgacta cccaaaatac |
| 1551 | tcagaggaag caaattaaa cagagaagaa atagatgggg taaagctgga |
| 1601 | atcaacaagg atttaccaga ttttggcgat ctattcaact gtcgccagtt |
| 1651 | cattggtact ggtagtctcc ctgggggcaa tcagtttctg gatgtgctct |
| 1701 | aatgggtctc tacagtgtag aatatgtatt taacattagg atttcagaag |
| 1751 | catgagaaaa acaccttgt ttctact |

SEQ ID NO 4 NA (neuraminidase) A/CA/07/09 amino acid sequence
| 1 | mnpnqkiiti gsvcmtigma nlilqignii siwishsiql gnqnqietcn |
|---|---|
| 51 | qsvityennt wvnqtyvnis ntnfaagqsv vsvklagnss lcpvsgwaiy |
| 101 | skdnsvrigs kgdvfvirep fiscsplecr tffltqgall ndkhsngtik |
| 151 | drspyrtlms cpigevpspy nsrfesvaws asachdginw ltigisgpdn |
| 201 | gavavlkyng iitdtikswr nnilrtqese cacvngscft vmtdgpsngq |
| 251 | asykifriek gkivksvemn apnyhyeecs cypdsseitc vcrdnwhgsn |
| 301 | rpwvsfnqnl eyqigyicsg ifgdnprpnd ktgscgpvss ngangvkgfs |
| 351 | fkygngvwig rtksissrng femiwdpngw tgtdnnfsik qdivginews |
| 401 | gysgsfvqhp eltgldcirp cfwvelirgr pkentiwtsg ssisfcgvns |
| 451 | dtvgwswpdg aelpftidk |

SEQ ID NO 5 NA (neuraminidase) A/CA/07/09 nt sequence
| 1 | agcaaaagca ggagtttaaa atgaatccaa accaaaagat aataaccaat |
|---|---|
| 51 | ggttcggtct gtatgacaat tggaatggct aacttaatat tacaaattgg |
| 101 | aaacataatc tcaatatgga ttagccactc aattcaactt gggaatcaaa |
| 151 | atcagattga acatgcaat caaagcgtca ttacttatga aaacaacact |
| 201 | tgggtaaatc agacatatgt taacatcagc aacaccaact tgctgctgg |
| 251 | acagtcagtg gtttccgtga aattagcggg caattcctct ctctgccctg |
| 301 | ttagtggatg ggctatatac agtaaagaca acagtgtaag aatcggttcc |

| | | | |
|---|---|---|---|
| 351 | aaggggatg | tgtttgtcat | aagggaacca ttcatatcat gctcccctt |
| 401 | ggaatgcaga | accttcttct | tgactcaagg ggccttgcta aatgacaaac |
| 451 | attccaatgg | aaccattaaa | gacaggagcc catatcgaac cctaatgagc |
| 501 | tgtcctattg | gtgaagttcc | ctctccatac aactcaagat ttgagtcagt |
| 551 | cgcttggtca | gcaagtgctt | gtcatgatgg catcaattgg ctaacaattg |
| 601 | gaatttctgg | cccagacaat | ggggcagtgg ctgtgttaaa gtacaacggc |
| 651 | ataataacag | acactatcaa | gagttggaga acaatatat tgagaacaca |
| 701 | agagtctgaa | tgtgcatgtg | taaatggttc ttgctttact gtaatgaccg |
| 751 | atggaccaag | taatggacag | gcctcataca agatcttcag aatagaaaag |
| 801 | ggaaagatag | tcaaatcagt | cgaaatgaat gcccctaatt atcactatga |
| 851 | ggaatgctcc | tgttatcctg | attctagtga atcacatgt gtgtgcaggg |
| 901 | ataactggca | tggctcgaat | cgaccgtggg tgtctttcaa ccagaatctg |
| 951 | gaatatcaga | taggatacat | atgcagtggg attttcggag acaatccacg |
| 1001 | ccctaatgat | aagacaggca | gttgtggtcc agtatcgtct aatggagcaa |
| 1051 | atggagtaaa | actgggacag | ttcaaatacg gcaatggtgt ttggataggg |
| 1101 | agaactaaaa | gcattagttc | aagaaacggt tttgagatga tttgggatcc |
| 1151 | gaacggatgg | actgggacag | acaataactt ctcaataaag caagatatcg |
| 1201 | taggaataaa | tgagtggtca | ggatatagcg ggagttttgt tcagcatcca |
| 1251 | gaactaacag | ggctggattg | tataagacct tgcttctggg ttgaactaat |
| 1301 | cagagggcga | cccaaagaga | cacaatctg gactagcggg agcagcatat |
| 1351 | ccttttgtgg | tgtaaacagt | gacactgtgg gttggtcttg gccagacggt |
| 1401 | gctgagttgc | catttaccat | tgacaagtaa tttgttcaaa aaaactccttg |
| 1451 | tttctact | | |

SEQ ID NO 6 V5-119E/186D HA AA

```
  1 DTLCIGYHAN NSTDTVDTVL EKNVTVTHSV NLLEDKHNGK LCKLRGVAPL
    HLGKCNIAGW
 61 ILGNPECESL STASSWSYIV ETPSSDNGTC YPGDFIDYEE LREQLSSVSS
    FERFEIFPET
121 SSWPNHDSNK GVTAACPHAG AKSFYKNLIW LVKKGNSYPK LSKSYINDKG
    KEVLVLWGIH
181 HPSTSDDQQS LYQNADAYVF VGSSRYSKKF KPEIAIRPKV RGQEGRMNYY
    WTLVEPGDKI
241 TFEATGNLVV PRYAFAMERN AGSGIIISDT PVHDCNTTCQ TPKGAINTSL
    PFQNIHPITI
301 GKCPKYVKST KLRLATGLRN IPSIQSRGLF GAIAGFIEGG WTGMVDGWYG
    YHHQNEQGSG
361 YAADLKSTQN AIDEITNKVN SVIEKMNTQF TAVGKEFNHL EKRIENLNKK
    VDDGFLDIWT
421 YNAELLVLLE NERTLDYHDS NVKNLYEKVR SQLKNNAKEI GNGCFEFYHK
    CDNTCMESVK
481 NGTYDYPKYS EEAKLNREEI DGVKLESTRI YQILAIYSTV ASSLVVVSL
    GAISFWMCSN
541 GSLQCRICI
```

SEQ ID NO 7 V5-119E/186D HA nucleotide

| | | | |
|---|---|---|---|
| 1 | agcaaaagca | ggggaaaaca | aaagcaacaa aaatgaaggc aatactagta gttctgctat |
| 61 | atacatttgc | aaccgcaaat | gcagacacat tatgtatagg ttatcatgcg aacaattcaa |
| 121 | cagacactgt | agacacagta | ctagaaaaga atgtaacagt aacacactct gttaaccttc |
| 181 | tagaagacaa | gcataacggg | aaactatgca aactaagagg ggtagcccca ttgcatttgg |
| 241 | gtaaatgtaa | cattgctggc | tggatcctgg gaaatccaga gtgtgaatca ctctccacag |

-continued

```
        Sequences:
 301    caagctcatg gtcctacatt gtggaaacac ctagttcaga caatggaacg
        tgttacccag
 361    gagatttcat cgattatgag gagctaagag agcaattgag ctcagtgtca
        tcatttgaaa
 421    ggtttgagat attccccgag acaagttcat ggcccaatca tgactcgaac
        aaaggtgtaa
 481    cggcagcatg tcctcatgct ggagcaaaaa gcttctacaa aaatttaata
        tggctagtta
 541    aaaaaggaaa ttcataccca aagctcagca atcctacatt aatgataaag
        ggaaagaag
 601    tcctcgtgct atggggcatt caccatccat ctactagtga tgaccaacaa
        agtctctatc
 661    agaatgcaga tgcatatgtt tttgtggggt catcaagata cagcaagaag
        ttcaagccgg
 721    aaatagcaat aagacccaaa gtgagggtc aagaagggag aatgaactat
        tactggacac
 781    tagtagagcc gggagacaaa ataacattcg aagcaactgg aaatctagtg
        gtaccgagat
 841    atgca tcgc aatggaaaga aatgctggat ctggtattat catttcagat
        acaccagtcc
 901    acgattgcaa taacttgt caaacaccca agggtgctat aaacaccagc
        ctcccatttc
 961    agaatataca tccgatcaca attggaaaat gtccaaaata tgtaaaagc
        acaaaattga
1021    gactggccac aggattgagg aatatcccgt ctattcaatc tagaggccta
        tttggggcca
1081    ttgccggttt cattgaaggg gggtggacag ggatggtaga tggatggtac
        ggttatcacc
1141    atcaaaatga gcaggggtca ggatatgcag ccgacctgaa gagcacacag
        aatgccattg
1201    acgagattac taacaaagta aattctgtta ttgaaaagat gaatacacag
        ttcacagcag
1261    taggtaaaga gttcaaccac ctggaaaaaa gaatagaaaa tttaaataaa
        aaagttgatg
1321    atggtttcct ggacatttgg acttacaatg ccgaactgtt ggttctattg
        gaaaatgaaa
1381    gaactttgga ctaccacgat tcaaatgtga agaacttata tgaaaaggta
        agaagccagc
1441    taaaaaacaa tgccaaggaa attggaaacg gctgctttga tttttaccac
        aaatgcgata
1501    acacgtgcat ggaaagtgtc aaaaatggga cttatgacta cccaaaatac
        tcagaggaag
1561    caaaattaaa cagagaagaa atagatgggg taaagctgga atcaacaagg
        atttaccaga
1621    ttttggcgat ctattcaact gtcgccagtt cattggtact ggtagtctcc
        ctgggggcaa
1681    tcagtttctg gatgtgctct aatgggtctc tacagtgtag aatatgtatt
        taacattagg
1741    atttcagaag catgagaaaa acacccttgt ttctact SEQ ID NO 8 V6-186D/273Y HA AA
   1    DTLCIGYHAN NSTDTVDTVL EKNVTVTHSV NLLEDKHNGK LCKLRGVAPL
        HLGKCNIAGW
  61    ILGNPECESL STASSWSYIV ETPSSDNGTC YPGDFIDYEE LREQLSSVSS
        FERFEIFPKT
 121    SSWPNHDSNK GVTAACPHAG AKSFYKNLIW LVKKGNSYPK LSKSYINDKG
        KEVLVLWGIH
 181    HPSTSDDQQS LYQNADAYVF VGSSRYSKKF KPEIAIRPKV RDEGRMNYY
        WTLVEPGDKI
 241    TFEATGNLVV PRYAFAMERN AGSGIIISDT PVYDCNTTCQ TPYKGAITSL
        PFQNIHPITI
 301    GKCPKYVKST KLRLATGLRN IPSIQSRGLF GAIAGFIEGG WTGMVDGWYG
        YHHQNEQGSG
 361    YAADLKSTQN AIDEITNKVN SVIEKMNTQF TAVGKEFNHL EKRIENLNKK
        VDDGFLDIWT
 421    YNAELLVLLE NERTLDYHDS NVKNLYEKVR SQLKNNAKEI GNGCFEFYHK
        CDNTCMESVK
 481    NGTYDYPKYS EEAKLNREEI DGVKLESTRI YQILAIYSTV ASSLVVVSL
        GAISFWMCSN
 541    GSLQCRICI SEQ. ID NO 9 V6-186D/273Y HA nucleotide
   1    agcaaaagca gggaaaaaca aaagcaacaa aaatgaaggc aatactagta
        gttctgctat
  61    atacatttgc aaccgcaaat gcagacacat tatgtatagg ttatcatgcg
        aacaattcaa
 121    cagacactgt agacacagta ctagaaaaga atgtaacagt aacacactct
        gttaaccttc
```

-continued

Sequences:

```
 181   tagaagacaa gcataacggg aaactatgca aactaagagg ggtagcccca
       ttgcatttgg
 241   gtaaatgtaa cattgctggc tggatcctgg gaaatccaga gtgtgaatca
       ctctccacag
 301   caagctcatg gtcctacatt gtggaaacac ctagttcaga caatggaacg
       tgttacccag
 361   gagatttcat cgattatgag gagctaagag agcaattgag ctcagtgtca
       tcatttgaaa
 421   ggtttgagat attccccaag acaagttcat ggcccaatca tgactcgaac
       aaaggtgtaa
 481   cggcagcatg tcctcatgct ggagcaaaaa gcttctacaa aaatttaata
       tggctagtta
 541   aaaaaggaaa ttcatacccca aagctcagca atcctacat taatgataaa
       gggaagaag
 601   tcctcgtgct atggggcatt caccatccat ctactagtga tgatcaacaa
       agtctctatc
 661   agaatgcaga tgcatatgtt tttgtggggt catcaagata cagcaagaag
       ttcaagccgg
 721   aaatagcaat aagacccaaa gtgagggatc gagaaggag aatgaactat
       tactggacac
 781   tagtagagcc gggagacaaa ataacattcg aagcaactgg aaatctagtg
       gtaccgagat
 841   atgcattcgc aatggaaaga aatgctggat ctggtattat catttcagat
       acaccagtct
 901   acgattgcaa tacaacttgt caaacaccca agggtgctat aaacaccagc
       ctcccatttc
 961   agaatataca tccgatcaca attggaaaat gtccaaaata tgtaaaaagc
       acaaaattga
1021   gactggccac aggattgagg aatatcccgt ctattcaatc tagaggccta
       tttggggcca
1081   ttgccggttt cattgaaggg gggtggacag ggatggtaga tggatggtac
       ggttatcacc
1141   atcaaaatga gcagggtca ggatatgcag ccgacctgaa gaatacacag
       aatgccattg
1201   acgagattac taacaaagta aattctgtta ttgaaaagat gaatacacag
       ttcacagcag
1261   taggtaaaga gttcaaccac ctggaaaaaa gaatagagaa tttaaataaa
       aaagttgatg
1321   atggtttcct ggacatttgg acttacaatg ccgaactgtt ggttctattg
       gaaaatgaaa
1381   gaactttgga ctaccacgat tcaaatgtga agaacttata taacaaagta
       agaagccagc
1441   taaaaaacaa tgccaaggaa attggaaacg gctgctttga atttttaccac
       aaaatgcgata
1501   acacgtgcat ggaaagtgtc aaaaatggga cttatgacta cccaaaatac
       tcagaggaag
1561   caaaattaaa cagagaagaa atagatgggg taaagctgga atcaacaagg
       atttaccaga
1621   ttttggcgat ctattcaact gtcgccagtt cattggtact ggtagtctcc
       ctggggggcaa
1681   tcagttttctg gatgtgctct aatgggtctc tacagtgtag aatatgtatt
       taacattagg
1741   atttcagaag catgagaaaa acaccattgt ttctact
```

---

What is claimed is:

1. An isolated or recombinant polypeptide, which polypeptide is selected from the group consisting of:

a) a polypeptide comprising the amino acid sequence of SEQ ID NO: 1;
   b) a polypeptide comprising the amino acid sequence of SEQ ID NO: 1 comprising at least one amino acid substitution selected from the group consisting of K119E, K119N and A186D;
   c) a polypeptide comprising the amino acid sequence of SEQ ID NO: 1 comprising the K119E and A186D amino acid substitutions;
   d) a polypeptide comprising the amino acid sequence of SEQ ID NO: 1 comprising the K119N and A186D amino acid substitutions;
   e) a polypeptide comprising an amino acid sequence of SEQ ID NO: 1 comprising a D222G and/or Q223R substitution;
   f) a polypeptide comprising an amino acid sequence of SEQ ID NO: 1 (i) comprising a D222G and/or Q223R substitution, and (ii) further comprising at least one amino acid substitution selected from the group consisting of K119E, K119N and A186D;
   g) a polypeptide comprising an amino acid sequence of SEQ ID NO: 1 (i) comprising a D222G and/or Q223R substitution, and (ii) further comprising the K119E and A186D amino acid substitutions;

h) a polypeptide comprising an amino acid sequence of SEQ ID NO: 1 (i) comprising a D222G and/or Q223R substitution, and (ii) further comprising the K119N and A186D amino acid substitutions;

i) a polypeptide comprising the amino acid sequence of residues 1-327 of SEQ ID NO:1;

j) a polypeptide comprising the amino acid sequence of residues 1-327 of SEQ ID NO: 1 comprising at least one amino acid substitution selected from the group consisting of K119E, K119N and A186D;

k) a polypeptide comprising the amino acid sequence of residues 1-327 of SEQ ID NO: 1 comprising the K119E and A186D amino acid substitutions;

l) a polypeptide comprising the amino acid sequence of residues 1-327 of SEQ ID NO: 1 comprising the K119N and A186D amino acid substitutions;

m) a polypeptide comprising an amino acid sequence of residues 1-327 of SEQ ID NO: 1 comprising a D222G and/or Q223R substitution;

n) a polypeptide comprising an amino acid sequence of residues 1-327 of SEQ ID NO: 1 (i) comprising a D222G and/or Q223R substitution, and (ii) further comprising at least one amino acid substitution selected from the group consisting of K119E, K119N and A186D;

o) a polypeptide comprising an amino acid sequence of residues 1-327 of SEQ ID NO: 1 (i) comprising a D222G and/or Q223R substitution, and (ii) further comprising the K119E and A186D amino acid substitutions;

p) a polypeptide comprising an amino acid sequence of residues 1-327 of SEQ ID NO: 1 (i) comprising a D222G and/or Q223R substitution, and (ii) further comprising the K119N and A186D amino acid substitutions;

q) a polypeptide comprising the amino acid sequence of SEQ ID NO:6;

r) a polypeptide comprising the amino acid sequence of residues 1-327 of SEQ IDNO:6;

s) a polypeptide comprising an amino acid sequence having at least 95%, at least 98%, at least 98.5%, at least 99%, at least 99.2%, at least 99.4%, at least 99.6%, at least 99.8% or at least 99.9% sequence identity to the amino acid sequence of the polypeptide of any one of (a) to (r);

t) a polypeptide comprising an amino acid sequence of the polypeptide of any one of (a) to (r) in which less than 3, less than 5, less than 10, less than 15, less than 20 amino acid residues were substituted, deleted or inserted;

u) a polypeptide comprising an amino acid sequence of the polypeptide of anyone of (a) to (r) and further comprising the H273Y substitution; and v) a polypeptide comprising the amino acid sequence of SEQ ID NO:8.

2. An isolated or recombinant nucleic acid comprising a polynucleotide encoding the polypeptide of claim 1.

3. The isolated or recombinant nucleic acid of claim 2 comprising the nucleotide sequence of SEQ ID NO 3 or SEQ ID NO:7.

4. The isolated or recombinant nucleic acid of claim 2, wherein the nucleic acid is DNA.

5. The isolated or recombinant nucleic acid of claim 2, wherein the nucleic acid is RNA.

6. The isolated or recombinant nucleic acid of claim 2, wherein the polynucleotide encodes an immunogenic polypeptide.

7. A composition comprising the isolated or recombinant nucleic acid of claim 2.

8. An immunogenic composition comprising an immunologically effective amount of the isolated or recombinant nucleic acid of claim 2.

9. A vector comprising the nucleic acid of claim 2.

10. The vector of claim 9 wherein the vector is a plasmid.

11. An isolated host cell comprising the vector of claim 9.

* * * * *

SEQUENCE LISTING

<160> NUMBER OF SEQ ID NOS: 9

<210> SEQ ID NO 1
<211> LENGTH: 549
<212> TYPE: PRT
<213> ORGANISM: H1N1 swine influenza virus

<400> SEQUENCE: 1

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala

-continued

```
                35                  40                  45
Pro Leu His Leu Gly Lys Cys Asn Ile Ala Gly Trp Ile Leu Gly Asn
50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                    85                  90                  95

Asp Tyr Glu Glu Leu Arg Glu Gln Leu Ser Ser Val Ser Ser Phe Glu
                100                 105                 110

Arg Phe Glu Ile Phe Pro Lys Thr Ser Ser Trp Pro Asn His Asp Ser
                115                 120                 125

Asn Lys Gly Val Thr Ala Ala Cys Pro His Ala Gly Ala Lys Ser Phe
130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
                180                 185                 190

Gln Asn Ala Asp Ala Tyr Val Phe Val Gly Ser Ser Arg Tyr Ser Lys
                195                 200                 205

Lys Phe Lys Pro Glu Ile Ala Ile Arg Pro Lys Val Arg Gly Gln Glu
210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
                260                 265                 270

His Asp Cys Asn Thr Thr Cys Gln Thr Pro Lys Gly Ala Ile Asn Thr
                275                 280                 285

Ser Leu Pro Phe Gln Asn Ile His Pro Ile Thr Ile Gly Lys Cys Pro
290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
                340                 345                 350

His Gln Asn Glu Gln Gly Ser Gly Tyr Ala Ala Asp Leu Lys Ser Thr
                355                 360                 365

Gln Asn Ala Ile Asp Glu Ile Thr Asn Lys Val Asn Ser Val Ile Glu
                370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
                420                 425                 430

Arg Thr Leu Asp Tyr His Asp Ser Asn Val Lys Asn Leu Tyr Glu Lys
                435                 440                 445

Val Arg Ser Gln Leu Lys Asn Asn Ala Lys Glu Ile Gly Asn Gly Cys
450                 455                 460
```

```
Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Glu Ile Asp Gly Val Lys Leu Glu Ser Thr Arg Ile Tyr Gln
            500                 505                 510

Ile Leu Ala Ile Tyr Ser Thr Val Ala Ser Ser Leu Val Leu Val Val
        515                 520                 525

Ser Leu Gly Ala Ile Ser Phe Trp Met Cys Ser Asn Gly Ser Leu Gln
    530                 535                 540

Cys Arg Ile Cys Ile
545

<210> SEQ ID NO 2
<211> LENGTH: 1777
<212> TYPE: DNA
<213> ORGANISM: H1N1 swine influenza virus

<400> SEQUENCE: 2
agcaaaagca ggggaaaaca aaagcaacaa aaatgaaggc aatactagta gttctgctat      60
atacatttgc aaccgcaaat gcagacacat tatgtatagg ttatcatgcg aacaattcaa     120
cagacactgt agacacagta ctagaaaaga atgtaacagt aacacactct gttaaccttc     180
tagaagacaa gcataacggg aaactatgca actaagaggg gtagccccca ttgcatttgg     240
gtaaatgtaa cattgctggc tggatcctgg gaaatccaga gtgtgaatca ctctccacag     300
caagctcatg gtcctacatt gtggaaacac ctagttcaga caatggaacg tgttacccag     360
gagatttcat cgattatgag gagctaagag agcaattgag ctcagtgtca tcatttgaaa     420
ggtttgagat attccccaag acaagttcat ggcccaatca tgactcgaac aaaggtgtaa     480
cggcagcatg tcctcatgct ggagcaaaaa gcttctacaa aaatttaata tggctagtta     540
aaaaaggaaa ttcataccca aagctcagca atcctacat taatgataaa gggaaagaag     600
tcctcgtgct atggggcatt caccatccat ctactagtgc tgaccaacaa agtctctatc     660
agaatgcaga tgcatatgtt tttgtggggt catcaagata cagcaagaag ttcaagccgg     720
aaatagcaat aagacccaaa gtgaggggtc aagaagggag aatgaactat tactggacac     780
tagtagagcc gggagacaaa ataacattcg agcaactgg aaatctagtg gtaccgagat     840
atgcattcgc aatggaaaga aatgctggat ctggtattat catttcagat acaccagtcc     900
acgattgcaa tacaacttgt caaacaccca agggtgctat aaacaccagc ctcccatttc     960
agaatataca tccgatcaca attggaaaat gtccaaaata tgtaaaaagc acaaaattga    1020
gactggccac aggattgagg aatatcccgt ctattcaatc tagaggccta tttgggggcca    1080 ttgccggttt cattgaaggg gggtggacag ggatggtaga tggatggtac ggttatcacc    1140
atcaaaatga gcagggtca ggatatgcag ccgacctgaa gagcacacag aatgccattg    1200
acgagattac taacaaagta aattctgtta ttgaaaagat gaatacacag ttcacagcag    1260
taggtaaaga gttcaaccac ctggaaaaaa gaatagagaa tttaaataaa aagttgatg    1320 atggtttcct ggacatttgg acttacaatg ccgaactgtt ggttctattg gaaaatgaaa    1380
gaactttgga ctaccacgat tcaaatgtga agaacttata tgaaaaggta gaagccagc    1440 taaaaacaa tgccaaggaa attggaaacg gctgctttga attttaccac aaatgcgata    1500
acacgtgcat ggaaagtgtc aaaaatggga cttatgacta cccaaaatac tcagaggaag    1560
caaaattaaa cagagaagaa atagatgggg taaagctgga atcaacaagg atttaccaga    1620
```

-continued

| | |
|---|---|
| ttttggcgat ctattcaact gtcgccagtt cattggtact ggtagtctcc ctgggggcaa | 1680 |
| tcagtttctg gatgtgctct aatgggtctc tacagtgtag aatatgtatt taacattagg | 1740 |
| atttcagaag catgagaaaa acaccccttgt ttctact | 1777 |

<210> SEQ ID NO 3
<211> LENGTH: 1777
<212> TYPE: DNA
<213> ORGANISM: H1N1 swine influenza virus

<400> SEQUENCE: 3

| | |
|---|---|
| agcaaaagca ggggaaaaca aaagcaacaa aaatgaaggc aatactagta gttctgctat | 60 |
| atacatttgc aaccgcaaat gcagacacat tatgtatagg ttatcatgcg aacaattcaa | 120 |
| cagacactgt agacacagta ctagaaaaga atgtaacagt aacacactct gttaaccttc | 180 |
| tagaagacaa gcataacggg aaactatgca actaagagg ggtagcccca ttgcatttgg | 240 |
| gtaaatgtaa cattgctggc tggatcctgg gaaatccaga gtgtgaatca ctctccacag | 300 |
| caagctcatg gtcctacatt gtggaaacac ctagttcaga caatggaacg tgttacccag | 360 |
| gagatttcat cgattatgag gagctaagag agcaattgag ctcagtgtca tcatttgaaa | 420 |
| ggtttgagat attccccgag acaagttcat ggcccaatca tgactcgaac aaaggtgtaa | 480 |
| cggcagcatg tcctcatgct ggagcaaaaa gcttctacaa aaatttaata tggctagtta | 540 |
| aaaaaggaaa ttcataccca aagctcagca atcctacat taatgataaa gggaaagaag | 600 |
| tcctcgtgct atggggcatt caccatccat ctactagtga tgaccaacaa agtctctatc | 660 |
| agaatgcaga tgcatatgtt tttgtggggt catcaagata cagcaagaag ttcaagccgg | 720 |
| aaatagcaat aagacccaaa gtgaggggtc aagaagggag aatgaactat tactggacac | 780 |
| tagtagagcc gggagacaaa ataacattcg aagcaactgg aaatctagtg gtaccgagat | 840 |
| atgcattcgc aatggaaaga aatgctggat ctggtattat catttcagat acaccagtcc | 900 |
| acgattgcaa tacaacttgt caaacaccca agggtgctat aaacaccagc ctcccatttc | 960 |
| agaatataca tccgatcaca attggaaaat gtccaaaata tgtaaaaagc acaaaattga | 1020 |
| gactggccac aggattgagg aatatcccgt ctattcaatc tagaggccta tttggggcca | 1080 |
| ttgccggttt cattgaaggg gggtggacag gcatggtaga tggatggtac ggttatcacc | 1140 |
| atcaaaatga gcagggtca ggatatgcag ccgacctgaa gagcacacag aatgccattg | 1200 |
| acgagattac taacaaagta aattctgtta ttgaaaagat gaatacacag ttcacagcag | 1260 |
| taggtaaaga gttcaaccac ctggaaaaaa gaatagagaa tttaaataaa aagttgatg | 1320 |
| atggtttcct ggacatttgg acttacaatg ccgaactgtt ggttctattg gaaaatgaaa | 1380 |
| gaactttgga ctaccacgat tcaaatgtga agaacttata tgaaaaggta gaagccagc | 1440 |
| taaaaaacaa tgccaaggaa attggaaacg gctgctttga attttaccac aaatgcgata | 1500 |
| acacgtgcat ggaaagtgtc aaaaatggga cttatgacta cccaaaatac tcagaggaag | 1560 |
| caaaattaaa cagagaagaa atagatgggg taaagctgga atcaacaagg atttaccaga | 1620 |
| ttttggcgat ctattcaact gtcgccagtt cattggtact ggtagtctcc ctgggggcaa | 1680 |
| tcagtttctg gatgtgctct aatgggtctc tacagtgtag aatatgtatt taacattagg | 1740 |
| atttcagaag catgagaaaa acaccccttgt ttctact | 1777 |

<210> SEQ ID NO 4
<211> LENGTH: 469
<212> TYPE: PRT
<213> ORGANISM: H1N1 swine influenza virus

<400> SEQUENCE: 4

```
Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415
```

```
Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 5
<211> LENGTH: 1458
<212> TYPE: DNA
<213> ORGANISM: H1N1 swine influenza virus

<400> SEQUENCE: 5
agcaaaagca ggagtttaaa atgaatccaa accaaaagat aataaccatt ggttcggtct      60
gtatgacaat tggaatggct aacttaatat tacaaattgg aaacataatc tcaatatgga     120
ttagccactc aattcaactt gggaatcaaa atcagattga acatgcaat caaagcgtca      180 ttacttatga aaacaacact tgggtaaatc agacatatgt taacatcagc aacaccaact     240 tgctgctgg acagtcagtg gtttccgtga aattagcggg caattcctct ctctgccctg      300
ttagtggatg ggctatatac agtaaagaca acagtgtaag aatcggttcc aaggggatg      360 tgtttgtcat aagggaacca ttcatatcat gctccccctt ggaatgcaga accttcttct     420
tgactcaagg ggccttgcta aatgacaaac attccaatgg aaccattaaa gacaggagcc     480
catatcgaac cctaatgagc tgtcctattg gtgaagttcc ctctccatac aactcaagat     540
ttgagtcagt cgcttggtca gcaagtgctt gtcatgatgg catcaattgg ctaacaattg     600
gaatttctgg cccagacaat ggggcagtgg ctgtgttaaa gtacaacggc ataataacag     660
acactatcaa gagttggaga aacaatatat tgagaacaca agagtctgaa tgtgcatgtg     720
taaatggttc ttgctttact gtaatgaccg atggaccaag taatggacag gcctcataca     780
agatcttcag aatagaaaag ggaaagatag tcaaatcagt cgaaatgaat gcccctaatt     840
atcactatga ggaatgctcc tgttatcctg attctagtga atcacatgt gtgtgcaggg      900 ataactggca tggctcgaat cgaccgtggg tgtctttcaa ccagaatctg aatatcaga     960 taggatacat atgcagtggg attttcggag acaatccacg ccctaatgat aagacaggca    1020
gttgtggtcc agtatcgtct aatggagcaa atggagtaaa agggttttca ttcaaatacg    1080
gcaatggtgt ttggataggg agaactaaaa gcattagttc aagaaacggt ttgagatga    1140 tttgggatcc gaacggatgg actgggacag acaataactt ctcaataaag caagatatcg    1200
taggaataaa tgagtggtca ggatatagcg ggagttttgt tcagcatcca gaactaacag    1260
ggctggattg tataagacct tgcttctggg ttgaactaat cagagggcga cccaaagaga    1320
acacaatctg gactagcggg agcagcatat cctttgtgg tgtaaacagt gacactgtgg    1380
gttggtcttg gccagacggt gctgagttgc catttaccat tgacaagtaa tttgttcaaa    1440
aaactccttg tttctact                                                  1458

<210> SEQ ID NO 6
<211> LENGTH: 549
<212> TYPE: PRT
<213> ORGANISM: H1N1 swine influenza virus

<400> SEQUENCE: 6

Asp Thr Leu Cys Ile Gly Tyr His Ala Asn Asn Ser Thr Asp Thr Val
1               5                   10                  15
```

-continued

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
            35                  40                  45

Pro Leu His Leu Gly Lys Cys Asn Ile Ala Gly Trp Ile Leu Gly Asn
 50                  55                  60

Pro Glu Cys Glu Ser Leu Ser Thr Ala Ser Ser Trp Ser Tyr Ile Val
 65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
                100                 105                 110

Arg Phe Glu Ile Phe Pro Glu Thr Ser Ser Trp Pro Asn His Asp Ser
                115                 120                 125

Asn Lys Gly Val Thr Ala Ala Cys Pro His Ala Gly Ala Lys Ser Phe
 130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Asp Asp Gln Gln Ser Leu Tyr
                180                 185                 190

Gln Asn Ala Asp Ala Tyr Val Phe Val Gly Ser Ser Arg Tyr Ser Lys
                195                 200                 205

Lys Phe Lys Pro Glu Ile Ala Ile Arg Pro Lys Val Arg Gly Gln Glu
210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
                260                 265                 270

His Asp Cys Asn Thr Thr Cys Gln Thr Pro Lys Gly Ala Ile Asn Thr
                275                 280                 285

Ser Leu Pro Phe Gln Asn Ile His Pro Ile Thr Ile Gly Lys Cys Pro
 290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
                340                 345                 350

His Gln Asn Glu Gln Gly Ser Gly Tyr Ala Ala Asp Leu Lys Ser Thr
                355                 360                 365

Gln Asn Ala Ile Asp Glu Ile Thr Asn Lys Val Asn Ser Val Ile Glu
 370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
                420                 425                 430

Arg Thr Leu Asp Tyr His Asp Ser Asn Val Lys Asn Leu Tyr Glu Lys

```
                    435               440                445
Val Arg Ser Gln Leu Lys Asn Asn Ala Lys Glu Ile Gly Asn Gly Cys
    450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Glu Ile Asp Gly Val Lys Leu Glu Ser Thr Arg Ile Tyr Gln
                500                 505                 510

Ile Leu Ala Ile Tyr Ser Thr Val Ala Ser Ser Leu Val Leu Val Val
            515                 520                 525

Ser Leu Gly Ala Ile Ser Phe Trp Met Cys Ser Asn Gly Ser Leu Gln
        530                 535                 540

Cys Arg Ile Cys Ile
545

<210> SEQ ID NO 7
<211> LENGTH: 1777
<212> TYPE: DNA
<213> ORGANISM: H1N1 swine influenza virus

<400> SEQUENCE: 7
```

| | | | | | |
|---|---|---|---|---|---|
| agcaaaagca | ggggaaaaca | aaagcaacaa | aaatgaaggc | aatactagta | gttctgctat | 60 |
| atacatttgc | aaccgcaaat | gcagacacat | tatgtatagg | ttatcatgcg | aacaattcaa | 120 |
| cagacactgt | agacacagta | ctagaaaaga | atgtaacagt | aacacactct | gttaaccttc | 180 |
| tagaagacaa | gcataacggg | aaactatgca | aactaagagg | ggtagcccca | ttgcatttgg | 240 |
| gtaaatgtaa | cattgctggc | tggatcctgg | gaaatccaga | gtgtgaatca | ctctccacag | 300 |
| caagctcatg | gtcctacatt | gtggaaacac | ctagttcaga | caatggaacg | tgttacccag | 360 |
| gagatttcat | cgattatgag | gagctaagag | agcaattgag | ctcagtgtca | tcatttgaaa | 420 |
| ggtttgagat | attccccgag | acaagttcat | ggcccaatca | tgactcgaac | aaaggtgtaa | 480 |
| cggcagcatg | tcctcatgct | ggagcaaaaa | gcttctacaa | aaatttaata | tggctagtta | 540 |
| aaaaaggaaa | ttcatacccc | aagctcagca | atcctacatt | taatgataaa | gggaaagaag | 600 |
| tcctcgtgct | atggggcatt | caccatccat | ctactagtga | tgaccaacaa | agtctctatc | 660 |
| agaatgcaga | tgcatatgtt | tttgtggggt | catcaagata | cagcaagaag | ttcaagccgg | 720 |
| aaatagcaat | aagacccaaa | gtgagggggtc | aagaagggag | aatgaactat | tactggacac | 780 |
| tagtagagcc | gggagacaaa | ataacattcg | aagcaactgg | aaatctagtg | gtaccgagat | 840 |
| atgcattcgc | aatggaaaga | aatgctggat | ctggtattat | catttcagat | acaccagtcc | 900 |
| acgattgcaa | tacaacttgt | caaacaccca | agggtgctat | aaacaccagc | ctcccatttc | 960 |
| agaatataca | tccgatcaca | attggaaaat | gtccaaaata | tgtaaaaagc | acaaaattga | 1020 |
| gactggccac | aggattgagg | aatatcccgt | ctattcaatc | tagaggccta | tttggggcca | 1080 |
| ttgccggttt | cattgaaggg | gggtggacag | ggatggtaga | tggatggtac | ggttatcacc | 1140 |
| atcaaaatga | gcagggtca | ggatatgcag | ccgacctgaa | gagcacacag | aatgccattg | 1200 |
| acgagattac | taacaaagta | aattctgtta | ttgaaaagat | gaatacacag | ttcacagcag | 1260 |
| taggtaaaga | gttcaaccac | ctggaaaaaa | gaatagagaa | tttaaataaa | aaagttgatg | 1320 |
| atggtttcct | ggacatttgg | acttacaatg | ccgaactgtt | ggttctattg | gaaaatgaaa | 1380 |
| gaactttgga | ctaccacgat | tcaaatgtga | agaacttata | tgaaaaggta | agaagccagc | 1440 |
| taaaaaacaa | tgccaaggaa | attggaaacg | gctgctttga | attttaccac | aaatgcgata | 1500 |

```
acacgtgcat ggaaagtgtc aaaaatggga cttatgacta cccaaaatac tcagaggaag    1560
caaaattaaa cagagaagaa atagatgggg taaagctgga atcaacaagg atttaccaga    1620
ttttggcgat ctattcaact gtcgccagtt cattggtact ggtagtctcc ctggggggcaa   1680 tcagtttctg gatgtgctct aatgggtctc tacagtgtag aatatgtatt taacattagg    1740
atttcagaag catgagaaaa acacccttgt ttctact                             1777
```

<210> SEQ ID NO 8
<211> LENGTH: 549
<212> TYPE: PRT
<213> ORGANISM: Haemophilus influenzae

<400> SEQUENCE: 8

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Asp Asp Gln Gln Ser Leu Tyr
            180                 185                 190

Gln Asn Ala Asp Ala Tyr Val Phe Val Gly Ser Ser Arg Tyr Ser Lys
        195                 200                 205

Lys Phe Lys Pro Glu Ile Ala Ile Arg Pro Lys Val Arg Asp Arg Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

Tyr Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
```

```
              325                 330                 335
Ile Glu Gly Gly Trp Thr Gly Met Val Asp Gly Trp Tyr Gly Tyr His
            340                 345                 350
His Gln Asn Glu Gln Gly Ser Gly Tyr Ala Ala Asp Leu Lys Ser Thr
        355                 360                 365
Gln Asn Ala Ile Asp Glu Ile Thr Asn Lys Val Asn Ser Val Ile Glu
    370                 375                 380
Lys Met Asn Thr Gln Phe Thr Ala Val Gly Lys Glu Phe Asn His Leu
385                 390                 395                 400
Glu Lys Arg Ile Glu Asn Leu Asn Lys Lys Val Asp Asp Gly Phe Leu
                405                 410                 415
Asp Ile Trp Thr Tyr Asn Ala Glu Leu Leu Val Leu Leu Glu Asn Glu
            420                 425                 430
Arg Thr Leu Asp Tyr His Asp Ser Asn Val Lys Asn Leu Tyr Glu Lys
        435                 440                 445
Val Arg Ser Gln Leu Lys Asn Asn Ala Lys Glu Ile Gly Asn Gly Cys
    450                 455                 460
Phe Glu Phe Tyr His Lys Cys Asp Asn Thr Cys Met Glu Ser Val Lys
465                 470                 475                 480
Asn Gly Thr Tyr Asp Tyr Pro Lys Tyr Ser Glu Glu Ala Lys Leu Asn
                485                 490                 495
Arg Glu Glu Ile Asp Gly Val Lys Leu Glu Ser Thr Arg Ile Tyr Gln
            500                 505                 510
Ile Leu Ala Ile Tyr Ser Thr Val Ala Ser Ser Leu Val Leu Val Val
        515                 520                 525
Ser Leu Gly Ala Ile Ser Phe Trp Met Cys Ser Asn Gly Ser Leu Gln
    530                 535                 540
Cys Arg Ile Cys Ile
545

<210> SEQ ID NO 9
<211> LENGTH: 1777
<212> TYPE: DNA
<213> ORGANISM: Haemophilus influenzae

<400> SEQUENCE: 9
agcaaaagca ggggaaaaca aaagcaacaa aaatgaaggc aatactagta gttctgctat    60
atacatttgc aaccgcaaat gcagacacat tatgtatagg ttatcatgcg aacaattcaa   120
cagacactgt agacacagta ctagaaaaga atgtaacagt aacacactct gttaaccttc   180
tagaagacaa gcataacggg aaactatgca actaagaggg gtagccccat tgcatttgg    240 gtaaatgtaa cattgctggc tggatcctgg gaaatccaga gtgtgaatca ctctccacag   300
caagctcatg gtcctacatt gtggaaacac ctagttcaga caatggaacg tgttacccag   360
gagatttcat cgattatgag gagctaagag agcaattgag ctcagtgtca tcatttgaaa   420
ggtttgagat attccccaag acaagttcat ggcccaatca tgactcgaac aaaggtgtaa   480
cggcagcatg tcctcatgct ggagcaaaaa gcttctacaa aaatttaata tggctagtta   540
aaaaaggaaa ttcatacccc aagctcagca atcctacat taatgataaa gggaagaag    600 tcctcgtgct atggggcatt caccatccat ctactagtga tgatcaacaa gtctctatc    660 agaatgcaga tgcatatgtt tttgtggggt catcaagata cagcaagaag ttcaagccgg   720
aaatagcaat aagacccaaa gtgagggatc gagaagggag aatgaactat tactggacac   780
tagtagagcc gggagacaaa ataacattcg aagcaactgg aaatctagtg gtaccgagat   840
```

```
atgcattcgc aatggaaaga aatgctggat ctggtattat catttcagat acaccagtct      900
acgattgcaa tacaacttgt caaacaccca agggtgctat aaacaccagc ctcccatttc      960
agaatataca tccgatcaca attggaaaat gtccaaaata tgtaaaaagc acaaaattga     1020
gactggccac aggattgagg aatatcccgt ctattcaatc tagaggccta tttggggcca     1080
ttgccggttt cattgaaggg gggtggacag ggatggtaga tggatggtac ggttatcacc     1140
atcaaaatga gcaggggtca ggatatgcag ccgacctgaa gagcacacag aatgccattg     1200
acgagattac taacaaagta aattctgtta ttgaaaagat gaatacacag ttcacagcag     1260
taggtaaaga gttcaaccac ctggaaaaaa gaatagagaa tttaaataaa aaagttgatg     1320
atggtttcct ggacatttgg acttacaatg ccgaactgtt ggttctattg gaaaatgaaa     1380
gaactttgga ctaccacgat tcaaatgtga agaacttata tgaaaaggta agaagccagc     1440
taaaaaacaa tgccaaggaa attggaaacg gctgctttga attttaccac aaatgcgata     1500
acacgtgcat ggaaagtgtc aaaaatggga cttatgacta cccaaaatac tcagaggaag     1560
caaaattaaa cagagaagaa atagatgggg taaagctgga atcaacaagg atttaccaga     1620
ttttggcgat ctattcaact gtcgccagtt cattggtact ggtagtctcc ctgggggcaa     1680
tcagtttctg gatgtgctct aatgggtctc tacagtgtag aatatgtatt taacattagg     1740
atttcagaag catgagaaaa acacccttgt ttctact                              1777
```